United States Patent

Whittaker et al.

[11] Patent Number: 5,276,153
[45] Date of Patent: Jan. 4, 1994

[54] PRODUCTION OF CERTAIN IMIDAZOPYRIDINYL-METHYL-BENZENE SULFONAMIDES

[75] Inventors: Mark Whittaker; Andrew Miller, both of Oxfordshire, England

[73] Assignee: British Bio-Technology Limited, Oxford, England

[21] Appl. No.: 990,273

[22] Filed: Dec. 14, 1992

Related U.S. Application Data

[63] Continuation of Ser. No. 746,246, Aug. 15, 1991, Pat. No. 5,180,723.

[30] Foreign Application Priority Data

Aug. 15, 1990 [GB] United Kingdom ................. 9017878
Aug. 16, 1990 [GB] United Kingdom ................. 9018040
Jun. 14, 1991 [GB] United Kingdom ................. 9112857

[51] Int. Cl.$^5$ .......................................... C07D 471/04
[52] U.S. Cl. ........................................ 546/82; 546/118
[58] Field of Search ................................ 546/82, 118

[56] References Cited

U.S. PATENT DOCUMENTS 4,804,658 2/1989 Manley et al. .................. 514/234
4,914,108 4/1990 Khanna et al. .................. 514/303
5,157,026 10/1992 Chakravarty et al. ............ 544/270

FOREIGN PATENT DOCUMENTS

0144804A2 6/1985 European Pat. Off. .
0238202A2 9/1987 European Pat. Off. .
0260613A2 3/1988 European Pat. Off. .

8908653 9/1989 PCT Int'l Appl. .

Primary Examiner—Bernard Dentz
Attorney, Agent, or Firm—Allegretti & Witcoff, Ltd.

[57] ABSTRACT

Compounds of general formula I;

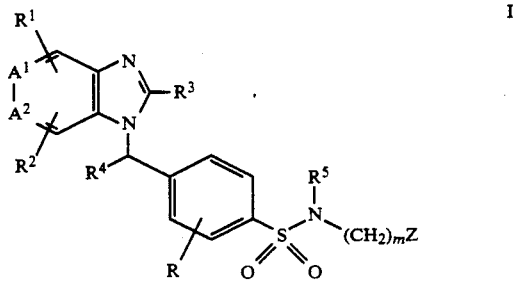

wherein:

$A^1$ is =N—, =CH— or =CR$^1$—;

$A^2$ is =N—, =CH— or =CR$^2$—;

provided that, when one of $A^1$ and $A^2$ is a nitrogen atom, the other of $A^1$ and $A^2$ is other than a nitrogen atom; wherein the rest of the variables are defined in the specification;

and their pharmaceutically and veterinarily acceptable acid addition salts and hydrates are antagonists of platelet activating factor (PAF) and as such are useful in the treatment or amelioration of various diseases or disorders mediated by PAF.

1 Claim, No Drawings

PRODUCTION OF CERTAIN IMIDAZOPYRIDINYL-METHYL-BENZENE SULFONAMIDES

This is a continuation of application Ser. No. 07/746,246, filed Aug. 15, 1991 now U.S. Pat. No. 5,180,723.

This invention relates primarily to compounds which are antagonists of Platelet Activating Factor (PAF).

Platelet Activating Factor (PAF) is a bioactive phospholipid which has been identified as 1-0-hexadecyl/octadecyl-2-acetyl-sn-glyceryl-3-phosphoryl choline. PAF is released directly from cell membranes and mediates a range of potent and specific effects on target cells resulting -in a variety of physiological responses which include hypotension, thrombocytopenia, bronchoconstriction, circulatory shock, and increased vascular permeability (oedema/erythema) . It is known that these physiological effects occur in many inflammatory and allergic diseases and PAF has been found to be involved in a number of such disorders including asthma, endotoxin shock, adult respiratory distress syndrome, glomerulonephritis, immune regulation, transplant rejection, gastric ulceration, psoriasis, cerebral, myocardial and renal ischemia. Thus the compounds of the invention, by virtue of their ability to antagonise the actions of PAF, should be of value in the treatment of any of the above conditions and any other conditions in which PAF is implicated (e.g. embryo implantation).

Compounds which have been disclosed as possessing activity as PAF antagonists include compounds which are structurally related to the PAF molecule such as glycerol derivatives (EP-A-0238202), and heterocyclic compounds such as 2,5-diaryl tetrahydrofurans (EP-A-0144804) and imidazopyridine derivatives (EP-A-0260613 and WO-A-8908653). Other imidazopyridine derivatives have also been disclosed (U.S. Pat. No. 4,914,108).

The present invention provides a range of novel and useful alkyl-, arylalkyl-, and in particular alkoxyalkyl-, benzimidazolylmethyl benzenesulphonamide and imidazopyridylmethylbenzenesulphonamide derivatives and their pharmaceutically acceptable acid addition salts, and pharmaceutical uses thereof as PAF antagonists. These derivatives, and in particular the alkoxyalkyl derivatives, in contrast to the compounds disclosed in the references above, display very high PAF antagonist activity.

According to a first aspect of the invention there is provided a compound of general formula I;

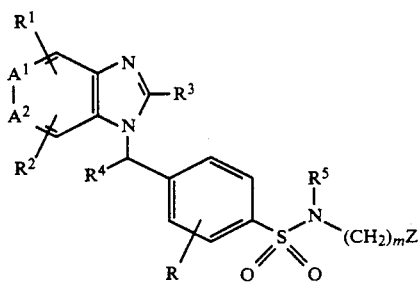

wherein:
$A^1$ is =N—, =CH— or =CR$^1$—;
$A^2$ is =N—, =CH— or =CR$^2$—;

provided that, when one of $A^1$ and $A^2$ is a nitrogen atom, the other of $A^1$ and $A^2$ is other than a nitrogen atom;

R represents hydrogen, —$C_1$—$C_6$ alkyl, —$C_2$—$C_6$ alkenyl, —$C_2$—$C_6$ alkynyl, halogen or —$OC_1$—$C_6$ alkyl;

$R^1$ and $R^2$ each independently represents hydrogen, —$C_1$—$C_6$ alkyl, —$C_2$—$C_6$ alkenyl, —$C_2$—$C_6$ alkynyl, halogen, —CN, —$CO_2H$, —$CO_2C_1$—$C_6$ alkyl, —$CONH_2$, —CHO, —$CH_2OH$, —$CF_3$, —$OC_1$—$C_6$ alkyl, —$SC_1$—$C_6$ alkyl, —$SOC_1$—$C_6$ alkyl, —$SO_2C_1$—$C_6$ alkyl, —$NH_2$, —NHCOMe or —$NO_2$, or $R^1$ and $R^2$ together with the carbon atoms to which they are attached form a fused phenyl ring;

$R^3$ represents hydrogen, —$C_1$—$C_6$ alkyl, —$C_2$—$C_6$ alkenyl, —$C_2$—$C_6$ alkynyl, —$OC_1$—$C_6$ alkyl, —$SC_1$—$C_6$ alkyl, —($C_1$—$C_6$ alkyl)$OC_1$—$C_6$ alkyl, —($C_1$—$C_6$ alkyl)$SC_1$—$C_6$ alkyl, —$CF_3$, —($C_1$—$C_6$ alkyl)phenyl, —$C_3$—$C_8$ cycloalkyl, —$C_4$—$C_8$ cycloalkenyl, —($C_1$—$C_6$ alkyl)$C_3$—$C_8$ cycloalkyl, —($C_1$—$C_6$ alkyl)$C_4$—$C_8$ cycloalkenyl or thiophenyl;

$R^4$ represents hydrogen, —$C_1$—$C_6$ alkyl, —$C_2$—$C_6$ alkenyl, —$C_2$—$C_6$ alkynyl, —$CO_2C_1$—$C_6$ alkyl, —$SC_1$—$C_6$ alkyl, —($C_1$—$C_6$ alkyl)$SC_1$—$C_6$ alkyl, —($C_1$—$C_6$ alkyl)$OC_1$—$C_6$ alkyl, —($C_1$—$C_6$ alkyl)phenyl or thiophenyl;

$R^5$ represents hydrogen, —$C_1$—$C_6$ alkyl, —$C_2$—$C_6$ alkenyl, —$C_2$—$C_6$ alkynyl, —$COC_1$—$C_6$ alkyl, —$CO_2C_1$—$C_6$ alkyl, —($CO_2C_1$—$C_6$ alkyl)phenyl, —($C_1$—$C_6$ alkyl)$CO_2C_1$—$C_6$ alkyl, —($C_1$—$C_6$ alkyl)phenyl, —$C_3$—$C_8$ cycloalkyl, —$C_4$—$C_8$ cycloalkenyl or phenyl optionally substituted by one or more substituents selected from —$C_1$—$C_6$ alkyl, —$OC_1$—$C_6$ alkyl, halogen, —$CF_3$, —CN;

m is an integer from 0 to 3;

Z is either a —$CR^6R^7R^8$ or —$CR^6$=$CR^7R^8$ group; wherein each of $R^6$, $R^7$, and $R^8$ independently represents hydrogen, halogen, —$C_1$—$C_{18}$ alkyl optionally substituted by one or more halogen atoms, —$C_2$—$C_{18}$ alkenyl, —$C_2$—$C_{18}$ alkynyl, —($C_1$—$C_6$ alkyl)$OC_1$—$C_{18}$ alkyl, —($C_1$—$C_6$ alkyl)$SC_1$—$C_{18}$ alkyl, —($C_1$—$C_6$ alkyl)$O(C_1$—$C_6$ alkyl)$OC_1$—$C_6$ alkyl, —($C_1$—$C_6$ alkyl)$S(C_1$—$C_6$ alkyl)$OC_1$—$C_6$ alkyl, —($C_1$—$C_6$ alkyl)$O(C_1$—$C_6$ alkyl)$SC_1$—$C_6$ alkyl, —($C_1$—$C_6$ alkyl)$S(C_1$—$C_6$ alkyl)$SC_1$—$C_6$ alkyl, —($C_1$—$C_6$ alkyl)$OC_2$—$C_6$ alkenyl, —$C_3$—$C_8$ cycloalkyl, —$C_4$—$C_8$ cycloalkenyl, —($C_1$—$C_6$ alkyl)$C_3$—$C_8$ cycloalkyl, —($C_1$—$C_6$ alkyl)$C_4$—$C_8$ cycloalkenyl, —($C_1$—$C_6$ alkyl)$OC_3$—$C_8$ cycloalkyl, —($C_1$—$C_6$ alkyl)$OC_4$—$C_8$ cycloalkenyl, —($C_1$—$C_6$ alkyl)$SC_3$—$C_8$ cycloalkyl, —($C_1$—$C_6$ alkyl)$SC_4$—$C_8$ cycloalkenyl, —($C_1$—$C_6$ alkyl)$N(C_1$—$C_6$ alkyl)$_2$, —($C_1$—$C_6$ alkyl)morpholino, —($C_1$—$C_6$ alkyl)$OCH_2Ph$, —$CH_2OSi(C_1$—$C_6$ alkyl)$_3$, —$CH_2OSiPh_2$-$C_1$—$C_6$ alkyl or a group —D wherein D represents a group;

$$-(CH_2)_n\text{—Ar}(R^9)(R^{10})(R^{11})$$

wherein n is an integer from 0 to 3, and each of $R^9$, $R^{10}$ and $R^{11}$ is independently hydrogen, —$C_1$—$C_6$ alkyl, —$OC_1$—$C_6$ alkyl, —$SC_1$—$C_6$ alkyl, —$N(C_1$—$C_6$ alkyl)$_2$, —$C_2$—$C_6$ alkenyl, —$C_2$—$C_6$ alkynyl, —$OCH_2Ph$, halogen, —CN, —$CF_3$, —$CO_2H$, —$CO_2C_1$—$C_6$ alkyl, —CONH$_2$, —CONHC$_1$—C$_6$ alkyl, —CONH(C$_1$—C$_6$ alkyl)$_2$, —CHO, —CH$_2$OH, —NH$_2$, —NHCOC$_1$—C$_6$ alkyl, —SOC$_1$—C$_6$ alkyl, or —SO$_2$C$_1$—C$_6$ alkyl;

or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "C$_1$—C$_6$ alkyl" refers to straight chain or branched chain hydrocarbon groups having from one to six carbon atoms. Illustrative of such alkyl groups are methyl, ethyl, propyl, isopgopyl, butyl, isobutyl, sec-butyl, tert-butyl, pentyl, neopentyl and hexyl.

As used herein the term "C$_2$—C$_6$ alkenyl" refers to straight chain or branched chain hydrocarbon groups having from two to six carbon atoms and having in addition one or more double bonds, each of either E or Z stereochemistry where applicable. This term would include for example, vinyl, 1-propenyl, 1- and 2-butenyl and 2-methyl-2-propenyl.

As used herein the term "C$_2$—C$_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "OC$_1$—C$_6$ alkyl" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "SC$_1$—C$_6$ alkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio.

As used herein, the term "C$_3$—C$_8$ cycloalkyl" refers to an alicyclic group having from 3 to 8 carbon atoms. Illustrative of such cycloalkyl groups are cyclopropyl, cyclobutyl, cyclopentyl, cyclohexyl, cycloheptyl and cyclooctyl.

As used herein, the term "C$_4$—C$_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein the term "N(C$_1$—C$_6$ alkyl)$_2$" refers to an amino group substituted with two straight chain or branched hydrocarbon groups each having from one to six carbon atoms. Illustrative of such dialkyl amino groups are N,N-dimethyl amino, N,N-diethyl amino, N,N-dipropyl amino, N,N-diisopropyl amino, N,N-dibutyl amino, N,N-diisobutyl amino, N,N-di-sec-butyl amino, N,N-di-tert-butyl amino, N,N-dipentyl amino, N,N-dineopentyl amino and N,N-dihexyl amino.

As used herein the term "C$_1$—C$_{18}$ alkyl" refers to straight chain or branched chain hydrocarbon groups having from one to eighteen carbon atoms. Illustrative of such alkyl groups are methyl, ethyl, propyl, isopropyl, butyl, isobutyl, sec-butyl, tert-butyl, pentyl, neopentyl, hexyl, decyl, dodecyl, tridecyl, tetradecyl, pentadecyl, hexadecyl, heptadecyl, and octadecyl. From one to six carbon atoms may be preferred.

As used herein the term "C$_2$—C$_{18}$ alkenyl" refers to straight chain or branched chain hydrocarbon groups having from two to eighteen carbon atoms and having in addition one or more double bonds, of either E or Z stereochemistry where applicable. This term would include for example, vinyl, 1-propenyl, 1- and 2-butenyl, 2-methyl-2-propenyl, geranyl, and farnesyl. From two to six carbon atoms may be preferred.

As used herein the term "C$_2$—C$_{18}$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl and 3-octadecynyl. From two to six carbon atoms may be preferred.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination:

A$^1$ represents —N=, —CH= or —CR$^1$=;

A$^2$ represents =N—, =CH— or =CR$^2$—;

R represents a hydrogen atom or a halogen (for example chlorine) atom;

R$^1$ represents a halogen (for example fluorine) atom or a hydrogen atom;

R$^2$ represents a halogen (for example fluorine) atom or a hydrogen atom;

R$^3$ represents a hydrogen atom or a —C$_1$—C$_6$ alkyl (for example methyl, ethyl or n-pentyl) group;

R$^4$ represents a hydrogen atom;

R$^5$ represents a hydrogen atom, a —C$_1$—C$_6$ alkyl (for example methyl, ethyl or isopropyl) group, a —C$_2$—C$_6$ alkenyl (for example allyl) group, a —COC$_1$—C$_6$ alkyl (for example acetyl) group, a —CO$_2$C$_1$—C$_6$ alkyl (for example ethoxycarbonyl or isobutoxycarbonyl) group, a —(CO$_2$C$_1$—C$_6$ alkyl)phenyl (for example benzyloxycarbonyl) group, a —(C$_1$—C$_6$ alkyl)phenyl (for example benzyl) group or a —C$_3$—C$_8$ cycloalkyl (for example cyclopentyl or cyclohexyl) group;

m represents an integer of 0, 1 or 2;

R$^6$ represents a hydrogen atom, a —C$_1$—C$_6$ alkyl (for example n-propyl, isopropyl, sec-butyl, isobutyl, n-pentyl, 3-methylbutyl) group, a —C$_2$—C$_6$ alkenyl (for example allyl) group or a group -D;

R$^7$ represents a —C$_1$—C$_6$ alkyl (for example methyl or isobutyl) group, a —(C$_1$—C$_6$ alkyl)OC$_1$—C$_{18}$ alkyl (for example methoxytpethyl, ethoxymethyl, butoxymethyl, pentoxymethyl or decyloxymethyl) group, —($C_1$—$C_6$ alkyl)O($C_1$—$C_6$ alkyl)O$C_1$—$C_6$ alkyl (for example ethoxymethoxymethyl or 2-methoxyethoxymethyl) group, a —($C_1$—$C_6$ alkyl)O$C_2$—$C_6$ alkenyl (for example allyloxymethyl) group, a —($C_1$—$C_6$ alkyl)morpholino (for example morpholino methyl) group, a —$CH_2OSiPh_2C_1$—$C_6$ alkyl (for example t-butyldiphenylsilyloxymethyl) group or a group —D;

$R^8$ represents a hydrogen atom;

D represents a

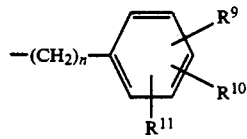

group;

wherein n represents an integer of 0, 1 or 2;

$R^9$ represents a hydrogen atom or a —O$C_1$—$C_6$ alkyl (for example methoxy) group;

$R^{10}$ represents a hydrogen atom or a —O$C_1$—$C_6$ alkyl (for example methoxy) group;

$R^{11}$ represents a hydrogen atom.

Particularly preferred compounds include those in which, independently or in any compatible combination:

$A^1$ represents —N=;

$A^2$ represents =CH—;

R represents a hydrogen atom or a halogen (for example chlorine) atom;

$R^1$ represents a hydrogen atom;

$R^2$ represents a hydrogen atom;

$R^3$ represents a —$C_1$—$C_6$ alkyl (for example methyl, ethyl or n-pentyl) group;

$R^4$ represents a hydrogen atom;

$R^5$ represents a hydrogen atom, a —$C_1$—$C_6$ alkyl (for example methyl or ethyl) group, a —CO$C_1$—$C_6$ alkyl (for example acetyl) group or a —$CO_2C_1$—$C_6$ alkyl (for example ethoxycarbonyl or isobutoxycarbonyl) group;

m represents an integer of 0;

Z represents a —$CR^6R^7R^8$ group;

$R^6$ represents a —$C_1$—$C_6$ alkyl (for example n-propyl, isopropyl, sec-butyl or isobutyl) group, a —$C_2$—$C_6$ alkenyl (for example allyl) group or a group —D;

$R^7$ represents a —($C_1$—$C_6$ alkyl)O$C_1$—$C_{18}$ alkyl (for example methoxymethyl, ethoxymethyl, butoxymethyl, pentoxymethyl or decyloxymethyl) group, a —($C_1$—$C_6$ alkyl)O($C_1$—$C_6$ alkyl)O$C_1$—$C_6$ alkyl (for example ethoxymethoxymethyl or 2-methoxyethoxymethyl) group or a —($C_1$—$C_6$ alkyl)O$C_2$—$C_6$ alkenyl (for example allyloxymethyl) group;

$R^8$ represents a hydrogen atom;

D represents a

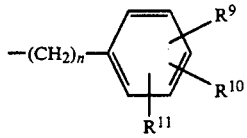

group;

wherein n represents an integer of 1;

$R^9$ represents a hydrogen atom;

$R^{10}$ represents a hydrogen atom;

$R^{11}$ represents a hydrogen atom.

The stereochemistry at the carbon atom to which $R^6$, $R^7$ and $R^8$ are attached is S.

Exemplary compounds include:

1. N-1-Methylhexyl 4—(1 H-2-methylbenzimidazolylmethyl)benzenesulphonamide,
2. N-1,4-Dimethylpentyl 4—(1 H-2-methylbenzimidazolylmethyl)benzenesulphonamide,
3. N-1-Methyl-3-phenylpropyl 4—(1 H-2-methylbenzimidazolyl-methyl)benzenesulphonamide,
4. N-Diphenylmethyl 4—(1 H-2-methylbenzimidazolylmethyl)benzenesulphonamide,
5. N-Diphenylmethyl-N-methyl 4—(1 H-2-methylbenzimidazolyl-methyl)benzenesulphonamide,
6. N-1,2-Diphenylethyl 4—(1 H-2-methylbenzimidazolylmethyl)benzenesulphonamide,
7. N—(S)-l-Benzyl-2-methoxyethyl 4—(1 H-2-methylbenzimidazolylmethyl)benzenesulphonamide,
8. N-1,2-Diphenylethyl-N-methyl 4—(1 H-2-methylbenzimidazolylmethyl)benzenesulphonamide,
9. N-1-Benzyl-2-phenylethyl 4—(19-2-methylbenzimidazolylmethyl)benzenesulphonamide,
10. N-2,2-Diphenylethyl 4—(1 H-2-methylbenzimidazolylmetfyl)benzenesulphonamide,
11. N-3,3-Diphenylpropyl 4—(1 H-2-methylbenzimidazolylmethyl)benzenesulphonamide,
12. N-Isopropyl-N-3,3-di(4-methoxy)phenyl-2-propenyl 4—(1 H-2-methylbenzimidazolylmethyl) benzenesulphonamide,
13. N-2—(3,4-Dimethoxy)phenylethyl 4—(1 H-2-methylbenzimidazolylmethyl) benzenesulphonamide,
14. N—Cyclopentyl-N-2—(3,4-dimethoxy)phenylethyl 4—(1 H-2-methylbenzimidazolylmethyl) benzenesulphonamide,
15. (A) N—Cyclopentyl-N-2—(3,4-dimethoxy)-phenylethyl 4—(3H-imidazo[4,5-c]pyridylmethyl)-benzenesulphonamide, (B) N—Cyclopentyl-N-2—(3,4-dimethoxy)-phenylethyl 4—(1 H-imidazo[4,5-c]pyridylmethyl)benzenesulphonamide, 16. N—Cyclohexyl-N-2—(3,4-dimethoxy)phenylethyl 4—(1 H-2-methylbenzimidazolylmethyl) benzenesulphonamide,
17. (A) N-1,2-Diphenylethyl 4—(3H-2-methylimidazo[4,5-c]pyridylmethyl) benzenesulphonamide, (B) N-1,2-Diphenylethyl 4—(1 H-2-methylimidazo(4,5-c]pyridylmethyl) benzenesulphonamide, 18. (A) N-1,2-Diphenylethyl-N-methyl 4—(3H-2-methylimidazo[4,5-c]pyridylmethyl) benzenesulphonamide, (B) N-1,2-Diphenylethyl-N-methyl 4—(1 H-2-methylimidazo[4,5-c]pyridylmethyl) benzenesulphonamide, 19. (A) N—(S)-l-Isobutyl-2-methoxyethyl 4—(3H-2-methylimidazo-(4,5-c]pyridylmethyl) benzenesulphonamide, (B) N—(S)-1-Isobutyl-2-methoxyethyl 4—(1 H-2-methylimidazo-[4,5-c]pyridylmethyl) benzenesulphonamide, 20. (A) N—(S)-1-Isobutyl-2-ethoxyethyl 4—(3H-2-methylimidazo-[4,5-c]pyridylmethyl) benzenesulphonamide, (B) N—(S)-1-Isobutyl-2-ethoxyethyl 4—(1 H-2-methylimidazo-[4,5-c]pyridylmethyl) benzenesulphonamide, 21. (A) N—(S)-1-Isobutyl-2-allyloxyethyl 4—(3H-2-methylimidazo-[4,5-c]pyridylmethyl) benzenesulphonamide,
(B) N—(S)-1-Isobutyl-2-allyloxyethyl 4—(1 H-2-methylimidazo-(4,5-c]pyridylmethyl) benzenesulphonamide,
22. (A) N—(S)-1-Isobutyl-2-n-butoxyethyl 4—(3H-2-methylimidazo-(4,5-c]pyridylmethyl) benzenesulphonamide,
(B) N—(S)-1-Isobutyl-2-n-butoxyethyl 4—(1 H-2-methylimidazo-[4,5-c]pyridylmethyl) benzenesulphonamide,
23. (A) N—(S)-1-Isobutyl-2-n-pentoxyethyl 4—(3H-2-methylimidazo-(4,5-c]pyridylmethyl) benzenesulphonamide,
(B) N—(S)-1-Isobutyl-2-n-pentoxyethyl 4—(1 H-2-methylimidazo-(4,5-c]pyridylmethyl) benzenesulphonamide,
24. (A) N—(S)-1-Isobutyl-2-ethoxymethoxyethyl 4—(3H-2-methyl-imidazo[4,5-c]pyridylmethyl) benzenesulphonamide,
(B) N—(S)-1-Isobutyl-2-ethoxymethoxyethyl 4—(1 H-2-methyl-imidazo[4,5-c]pyridylmethyl) benzenesulphonamide,
25. (A) N—(S)-1-Isobutyl-2—(2-methoxyethoxy)ethyl 4—(3H-2-methylimidazo (4,5-c]pyridylmethyl)benzenesulphonamide,
(B) N—(S)-1-Isobutyl-2—(2-methoxyethoxy)ethyl 4—(1 H-2-methylimidazo [4,5-c]pyridylmethyl)benzenesulphonamide,
26. (A) N—(S)-1-Isobutyl-2-decyloxyethyl 4—(3H-2-methylimidazo-(4,5-c]pyridylmethyl) benzenesulphonamide,
(B) N—(S)-1-Isobutyl-2-decyloxyethyl 4—(1 H-2-methylimidazo-[4,5-c]pyridylmethyl) benzenesulphonamide,
27. (A) N—(R)-1-Isobutyl-2-ethoxyethyl 4—(3H-2-methylimidazo-(4,5-c]pyridylmethyl)benzenesulphonamide,
(B) N—(R)-1-Isobutyl-2-ethoxyethyl 4—(1 H-2-methylimidazo-[4,5-c]pyridylmethyl)benzenesulphonamide,
28. (A) N—(R)-1-Isobutyl-2-allyloxyethyl 4—(3H-2-methylimidazo-(4,5-c]pyridylmethyl)benzenesulphonamide,
(B) N—(R)-1-Isobutyl-2-allyloxyethyl 4—(1 H-2-methylimidazo-[4,5-c]pyridylmethyl)benzenesulphonamide,
29. (A) N-1-n-Propyl-2-ethoxyethyl 4—(3H-2-methylimidazo[4,5-c]-pyridylmethyl) benzenesulphonamide,
(B) N-1-n-Propyl-2-ethoxyethyl 4—(1 H-2-methylimidazo[4,5-c]-pyridylmethyl) benzenesulphonamide,
30. (A) N—(S)-1-sec-Butyl-2-ethoxyethyl 4—(3H-2-methylimidazo-(4,5-c]pyridylmethyl) benzenesulphonamide,
(B) N—(S)-1-sec-Butyl-2-ethoxyethyl 4—(1 H-2-methylimidazo-(4,5-c]pyridylmethyl) benzenesulphonamide,
31. (A) N—(S)-1-Benzyl-2-ethoxyethyl 4—(3H-2-methylimidazo[4,5-c]-pyridylmethyl) benzenesulphonamide,
(B) N—(S)-1-Benzyl-2-ethoxyethyl 4—(1 H-2-methylimidazo(4 5-c]pyridylmethyl) benzenesulphonamide,
32. (A) N-1-Allyl-2-ethoxyethyl 4—(3H-2-methylimidazo(4,5-c]-pyridylmethyl) benzenesulphonamide,
(B) N-1-Allyl-2-ethoxyethyl 4—(1 H-2-methylimidazo(4,5-c]-pyridylmethyl)benzenesulphonamide,
33. N—(S)-1-Isobutyl-2-morpholinoethyl 4—(2-methyl-benzimidazolylmethyl) benzenesulphonamide,
34. (A) N—(S)-1-Isobutyl-2-morpholinoethyl 4—(3H-2-methylimidazo (4,5-c]pyridylmethyl)benzenesulphonamide,
(B) N—(S)-1-Isobutyl-2-morpholinoethyl 4—(1 H-2-methylimidazo [4,5-c]pyridylmethyl)benzenesulphonamide,
35. (A) N-Methyl-N—(S)-1-isobutyl-2-ethoxyethyl 4—(3H-2-methylimidazo [4,5-c]pyridylmethyl)benzenesulphonamide,
(B) N-Methyl-N—(S)-1-isobutyl-2-ethoxyethyl 4—(1 H-2-methylimidazo (4,5-c]pyridylmethyl)benzenesulphonamide,
36. (A) N-Methyl-N—(S)-1-isobutyl-2-allyloxyethyl 4—(3H-2-methylimidazo (4,5-c]pyridylmethyl)benzenesulphonamide,
(B) N-Methyl-N—(S)-1-isobutyl-2-allyloxyethyl 4—(1 H-2-methylimidazo [4,5-c]pyridylmethyl)benzenesulphonamide,
37. (A) N-Methyl-N—(S)-1-isobutyl-2-n-butoxyethyl 4—(3H-2-methylimidazo [4,5-c]pyridylmethyl)benzenesulphonamide,
(B) N-Methyl-N—(S)-1-isobutyl-2-n-butoxyethyl 4—(1 H-2-methylimidazo [4,5-c]pyridylmethyl)benzenesulphonamide,
38. (A) N-Methyl-N—(S)-1-isobutyl-2-n-pentoxyethyl 4—(3H-2-methylimidazo [4,5-c]pyridylmethyl)benzenesulphonamide,
(B) N-Methyl-N—(S)-1-isobutyl-2-n-pentoxyethyl 4—(1H-2-methylimidazo [4,5-c]pyridylmethyl)benzenesulphonamide,
39. (A) N-Methyl-N—(R)-1-isobutyl-2-allyloxyethyl 4—(3H-2-methylimidazo [4,5-clpyridylmethyl)benzenesulphonamide,
(B) N-Methyl-N—(R)-1-isobutyl-2-allyloxyethyl 4—(1 H-2-methylimidazo [4,5-clpyridylmethyl)benzenesulphonamide,
40. (A) N-Methyl-N—(S)-1-sec-butyl-2-methoxyethyl 4—(3H-2-methylimidazo (4,5-clpyridylmethyl)benzenesulphonamide,
(B) N-Methyl-N—(S)-1-sec-butyl-2-methoxyethyl 4—(1 H-2-methylimidazo [4,5-clpyridylmethyl)benzenesulphonamide,
41. N-Methyl-N—(S)-1-isobutyl-2-ethoxyethyl 4—(1H-2-methyl-benzimidazoylmethyl) benzenesulphonamide,
42. (A) N-Methyl-N—(S)-1-isobutyl-2-ethoxyethyl 4—(1 H-2-methyl -5-fluorobenzimidazoylmethyl) benzenesulphonamide,
(B) N-Methyl-N—(S)-1-isobutyl-2-ethoxyethyl 4—(1 H-2-methyl -6-fluorobenzimidazoylmethyl)benzenesulphonamide,
43. N-Allyl-N—(S)-1-isobutyl-2-ethoxyethyl 4—(1 H-2-methyl-benzimidazoylmethyl)benzenesulphonamide,
44 .(A) N-Ethyl-N-1-allyl-2-ethoxyethyl 4—(3H-2-methylimidazo-(4,5-c]pyridylmethyl)benzenesulphonamide,
(B) N-Ethyl-N-1-allyl-2-ethoxyethyl 4—(1 H-2-methylimidazo-(4,5-c]pyridylmethyl)benzenesulphonamide, 45. N-Isobutoxycarbonyl-N—(S)-1-isobutyl-2-ethoxyethyl 4—(1 H-2-methylbenzimidazoylmethyl) benzenesulphonamide, 46. (A) N-Isobutoxycarbonyl-N—(S)-1-isobutyl-2-ethoxyethyl 4—(3H-2-methylimidazo [4,5-c]pyridylmethyl)benzenesulphonamide, (B) N-Isobutoxycarbonyl-N—(S)-1-isobutyl-2-ethoxyethyl 4—(1 H-2-methylimidazo [4,5-c]pyridylmethyl)benzenesulphonamide, 47. N-Benzyloxycarbonyl-N—(S)-1-isobutyl-2-ethoxyethyl 4—(1 H-2-methylbenzimidazoylmethyl) benzenesulphonamide, 48. (A) N-Ethoxycarbonyl-N—(S)-1-isobutyl-2-ethoxyethyl 4—(3H-2-methylimidazo [4,5-clpyridylmethyl)benzenesulphonamide, (B) N-Ethoxycarbonyl-N—(S)-1-isobutyl-2-ethoxyethyl 4—(1 H-2-methyl -imidazo(4,5-c]pyridylmethyl)benzenesulphonamide, 49. N-Acetyl-N—(S)-1-isobutyl-2-ethoxyethyl 4—(1 H-2-methyl-imidazo [4,5-clpyridylmethyl)benzenesulphonamide, 50. N-Methyl-N—(S)-1-isobutyl-2-ethoxyethyl 4—(1 H-2-ethyl-imidazo [4,5-c]pyridylmethyl)benzenesulphonamide, 51. N-Methyl-N—(S)-1-isobutyl-2-ethoxyethyl 4—(1 H-2-n-pentyl-imidazo [4,5-clpyridylmethyl)benzenesulphonamide, 52. (A) N-Methyl-N—(S)-1-isobutyl-2-t-butyldiphenylsilyloxyethyl 4-(3H-2-methylimidazo[4,5-c]pyridylmethyl)benzenesulphonamide, (B) N-Methyl-N—(S)-I-isobutyl-2-t-butyldiphenylsilyloxyethyl 4-(1 H-2-methylimidazo[4,5-c]pyridylmethyl)benzenesulphonamide, 53. (A) N-1-Isobutylpentyl 4—(3H-2-methylimidazo[4,5-c]pyridyl-methyl) benzenesulphonamide, (B) N-1-Isobutylpentyl 4—(1 H-2-methylimidazo[4,5-c]pyridyl-methyl) benzenesulphonamide, 54. (A) N-Benzyl-N-I-isobutylpentyl 4—(3H-2-methylimidazo(4,5-c]pyridylmethyl) benzenesulphonamide, (B) N-Benzyl-N-1-isobutylpentyl 4—(1 H-2-methylimidazo(4,5-c]pyridylmethyl) benzenesulphonamide, 55. (A) N-Ethyl-N—(S)-1-isobutyl-2-ethoxyethyl 3-chloro-4—(3H-2-methylimidazo [4,5-clpyridylmethyl)benzenesulphonamide, (B) N-Ethyl-N—(S)-1-isobutyl-2-ethoxyethyl 3-chloro-4—(1 H-2-methylimidazo [4,5-clpyridylmethyl)benzenesulphonamide.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) treating an imidazole derivative represented by general formula II

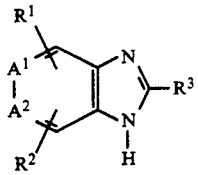

wherein $A^1$, $A^2$, $R^1$, $R^2$ and $R^3$ are as defined in general formula I, with a suitable base (e.g. sodium hydride, potassium hydride, sodium bis(trimethylsilyl)amide or potassium hydroxide), followed by a compound of general formula III

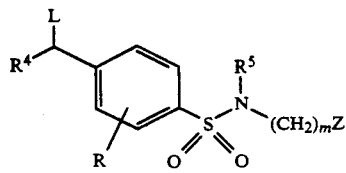

wherein R, $R^4$, $R^5$, m and Z are as defined in general formula I, and L is chloro, bromo, iodo, methanesulphonyloxy, p-toluenesulphonyloxy or trifluoromethanesulphonyloxy; or (b) treating a substituted diamino compound of general formula IV

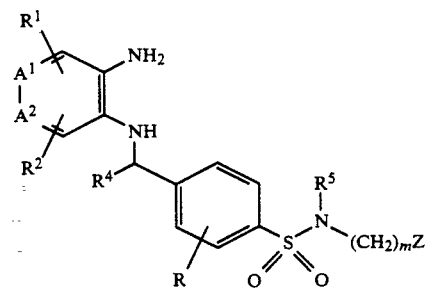

wherein $A^1$, $A^2$, R, $R^1$, $R^2$, $R^4$, $R^5$, m and Z are as defined in general formula I, with a carboxylic acid of general formula V $R^3CO_2H$      V wherein $R^3$ is as defined in general formula I, or a suitable derivative thereof; and (c) optionally after step (a) or step (b) converting, in one or a plurality of steps, a compound of general formula I into another compound of general formula I.

The reaction of step (a) can for preference be conducted in an aprotic solvent (e.g. tetrahydrofuran, N,N-dimethylformamide or acetonitrile) to yield compounds of general formula I. In the case where an unsymmetrically substituted imidazole derivative is used the reaction can yield an isomeric mixture, which is separated by chromatography to yield compounds of general formula I.

In step (b), derivatives of carboxylic acids of general formula V, which are suitable substrates for the reaction include acid halides of general formula VI $R^3CO_2X$      VI wherein R³ is as defined in general formula I and X is fluoride, chloride, bromide or iodide, acid anhydrides of general formula VII (R³CO)₂O    VII wherein R³ is as defined in general formula I, trialkylorthoesters of general formula VIII

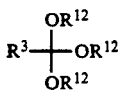    VIII wherein R³ is as defined in general formula I and R¹² is —C₁—C₆ alkyl, or imino ether salts of general formula IX

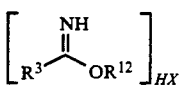    IX wherein R³ is as defined in general formula I, R¹² is —C₁—C₆ alkyl and X is fluoride, chloride, bromide, or iodide. Carboxylic acids of general formula V, acid halides of general formula VI, acid anhydrites of general formula VII, trialkylorthoesters of general formula VIII and imino ether salts of general formula IX are available in the art or can be prepared by methods analogous to those known in the art.

By means of step (c) compounds of general formula I may be prepared by the treatment of a compound of general formula I wherein R⁵ is hydrogen with base followed by an electrophile of general formula X

LR⁵    X wherein R⁵ is as defined in general formula I but is not a hydrogen atom, a phenyl or a substituted phenyl group, and L is as defined in III. Electrophiles of general formula X are available in the art or can be prepared by procedures known to those skilled in the art.

Also by means of step (c) certain compounds of general formula I wherein R⁵ is as defined in general formula I but is not a hydrogen atom, can be prepared by treatment of a compound of general formula. I wherein R⁴ is a hydrogen atom with a suitable base (e.g. sodium bis(trimethylsilyl)amide) in an aprotic solvent (e.g. tetrahydrofuran) followed by an electrophile of the general formula LR⁴ wherein R⁴ is —C₁—C₆ alkyl, —C₃—C₆ alkenyl, —C₃—C₆ alkynyl, —CO₂C₁—C₆ alkyl, —C₁—C₆ alkyl)SC₁—C₆ alkyl, —(C₁—C₆ alkyl)OC₁—C₆ alkyl or —(C₁—C₆ alkyl)phenyl and L is chloro, bromo, iodo, methanesulphonyloxy, p-toluenesulphonyloxy or trifluoromethanesulphonyloxy or by a C₁—C₆ alkyl disulphide or phenyl disulphide electrophile. Electrophiles of the general formula LR⁴ and disulphide electrophiles are available in the art or can be prepared by methods analogous to those known in the art.

Imidazole derivatives of general formula II may be prepared by a number of methods. The first method involves treatment of a 1,2-diamine of general formula XI

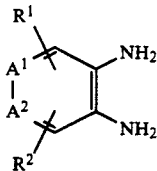    XI wherein A¹, A², R¹ and R² are as defined in general formula I, with a carboxylic acid of general formula V, an acid halide of general formula VI, an acid anhydride of general formula VII, a trialkylorthoester of general formula VIII or an imino ether salt of general formula IX.

1,2-Diamines of general formula XI are available in the art or may be prepared by the reduction of a 1,2-nitroamine of general formula XII

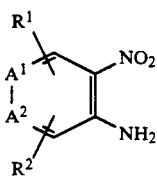    XII wherein A¹, A², R¹ and R² are as in general formula I, for example in the presence of hydrogen and a catalyst such as palladium or platinum.

1,2-Nitroamines of general formula XII are available in the art or can be prepared by methods analogous to those known in the art.

In a second method imidazole derivatives of general formula II may be prepared by the treatment of an 1,2-nitroamide of general formula XIII

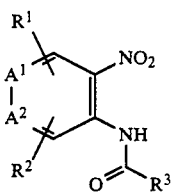    XIII wherein A¹, A², R¹, R² and R³ are as defined in general formula I, with a suitable reducing agent (e.g. tin in acetic acid).

1,2-Nitroamides of general formula XIII may be prepared by the treatment of a 1,2-nitroamine of general formula XII with an acid chloride of general formula VI wherein R³ is as defined in general formula I, in an aprotic solvent and in the presence of a suitable base such as, for example, triethylamine. Alternatively, the reaction may be conducted utilising an acid anhydride of general formula VII wherein R³ is as defined in general formula I.

Another procedure for preparing 1,2-nitroamides of general formula XIII involves reaction of a 1,2-nitroamine of general formula XII with a carboxylic acid of general formula V, wherein R³ is as defined in general formula I, in the presence of a coupling reagent (e.g. 1,3-dicyclohexylcarbodiimide).

Compounds of general formula III may be prepared by treatment of an amine of general formula XIV

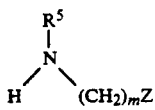

wherein $R^5$, m and Z are as defined in general formula I, with a sulphonyl halide of general formula XV

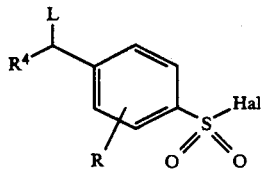

wherein R and $R^4$ is as defined in general formula I, L is as defined in general formula III and Hal is a halide (e.g. fluoro, chloro or bromo), in the presence of a suitable base (e.g. triethylamine). Amines of general formula XIV and sulphonyl halides of general formula XV are known in the art or may be prepared by methods known in the art.

Substituted 1,2-diamines of general formula IV may be prepared by the reduction of a substituted 1,2-nitroamine of general formula XVI

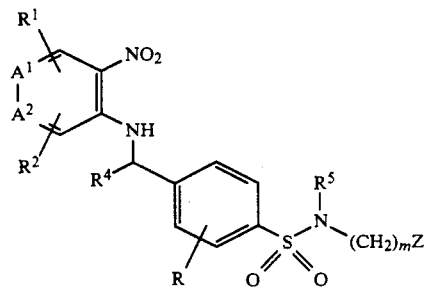

wherein $A^1$, $A^2$, R, $R^1$, $R^2$, $R^4$, $R^5$, m and Z are as in general formula I, for example in the presence of hydrogen and a catalyst such as palladium or platinum.

Substituted 1,2-nitroamines of general formula XVI may be prepared by a number of methods. The first of these methods involves the treatment of a nitro compound of general formula XVII

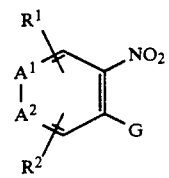

wherein $A^1$, $A^2$, $R^1$ and $R^2$ are as defined in general formula I and G is halo or $-OC_1-C_6$ alkyl; is treated with an amino compound of general formula XVIII

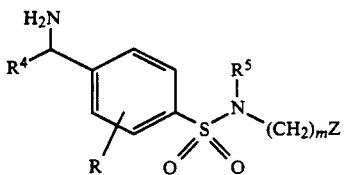

wherein R, $R^4$, $R^5$, m and Z are as defined in general formula I. Nitro compounds of general formula XVII are available in the art or can be prepared by methods analogous to those known in the art. Amino compounds of general formula XVIII can be prepared by treatment of a compound of general formula III with hexamethylenetetramine followed by treatment with ethanolic hydrochloric acid or by sequential treatment of a compound of general formula III with sodium azide followed by triphenylphosphine or by hydrogenation over a suitable catalyst.

A second procedure for the preparation of amino nitrobenzenes Of general formula XVI involves the reduction of an imino nitro compound of general formula XIX

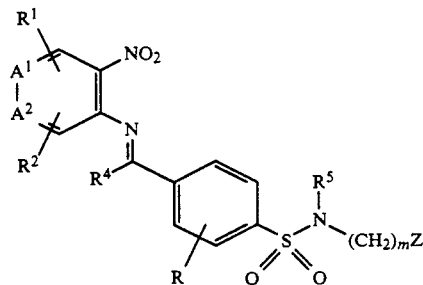

wherein $A^1$, $A^2$, R, $R^1$, $R^2$, $R^4$, $R^5$, m and Z are as defined in general formula I, for example by the action sodium cyanoborohydride.

The imino nitro compounds Of general formula XIX may be prepared by treating a 1,2-nitroamine general formula XII with a substituted carbonyl derivative of general formula XX

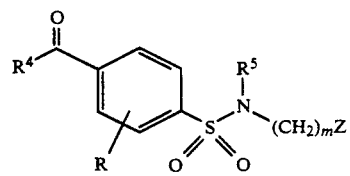

wherein R, $R^5$, m and Z are as defined in general formula I and $R^4$ is as defined in general formula I but is not a $-SC_1-C_6$ alkyl group. Substituted carbonyl derivatives of general formula XX may be prepared by treatment of a compound of general formula III with an oxidising agent (e.g. dimethyl sulphoxide).

Alternatively nitro amino compounds of general formula XIV in which $R^4$ is hydrogen may be prepared by the reduction of a 1,2-nitroamide of general formula XXI

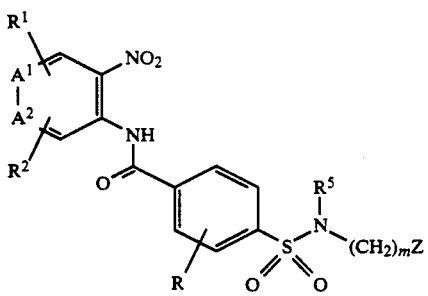

XXI wherein $A^1$, $A^2$, R, $R^1$, $R^2$, $R^5$, m and Z are as defined in general formula I, with a suitable metal hydride reducing agent such as for example lithium aluminium hydride.

The 1,2-nitroamides of general formula XXI may be prepared by the coupling of a 1,2-nitroamine of general formula XII with an acid chloride of general formula XXII

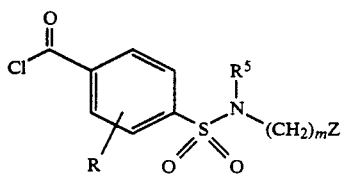

XXII wherein R, $R^5$, m and Z are as defined in general formula I, in an aprotic solvent and in the presence of a suitable base such as, for example, triethylamine. Alternatively, the reaction may be conducted utilising an acid anhydride of general formula XXIII

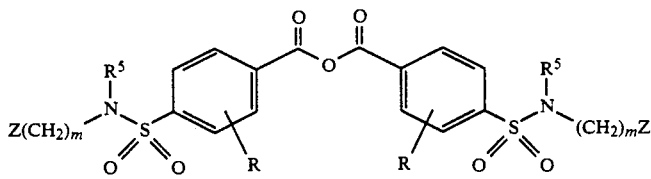

XXIII wherein R, $R^5$, m and Z are as defined in general formula I. Another procedure for preparing 1,2-nitroamides of general formula XXI involves reaction of a 1,2-nitroamine of general formula XII with a carboxylic acid of general formula XXIV

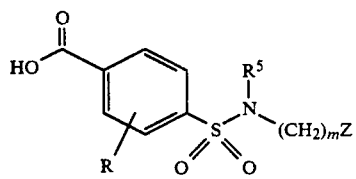

XXIV wherein R, $R^5$, m and Z are as defined in general formula I, in the presence of a coupling reagent (e.g. 1,3-dicyclohexylcarbodiimide). Acid chlorides of general formula XXII, acid anhydrides of general formula XXIII and carboxylic acids of general formula XXIV may be prepared-from carbonyl derivatives of general formula XX wherein $R^4$ is hydrogen by procedures known to those skilled in the art.

The appropriate solvents employed in the above reactions are solvents wherein the reactants are soluble b-ut do not react with the reactants. The preferred solvents vary from reaction to reaction and are readily ascertained by one of ordinary skill in the art.

Compounds of general formulae II, III, IV and XVI are valuable intermediates in the preparation of compounds of general formula I, as are other novel compounds specifically or generically disclosed herein. According to a third aspect of the invention, there is therefore provided a compound of general formula II. According to a fourth aspect of the invention, there is provided a compound of general formula III. According to a fifth aspect of the invention, there is provided a compound of general formula IV. According to a sixth aspect of the invention there is provided a compound of general formula XVI.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient.

In addition to the treatment of warm blooded animals such as mice, rats, horses, cattle, pigs, sheep, dogs, cats, etc., the compounds of the invention are effective in the treatment of humans.

According to a seventh aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an eighth aspect of the invention there is provided the use of a compound of general formula I in the preparation of an agent for the treatment of PAF-mediated diseases, and/or the treatment of inflammatory disorders; such as rheumatoid arthritis, osteoarthritis and eye inflammation, cardiovascular disorder, thrombocytopenia, asthma, endotoxin shock, adult respiratory distress syndrome, glomerulonephritis, immune regulation, gastric ulceration, transplant rejection, psoriasis, allergic dermatitis, urticaria, multiple sclerosis, cerebral, myocardial and renal ischemia and any other condition in which PAF is implicated.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrilsternal injection or infusion techniques.

According to a ninth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hemitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipcents, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or bucal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacologifal active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compounds of general formula, I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to the pharmacological example 1.

The following examples illustrate the invention, but are not intended to limit the scope in any way.

The following abbreviations have been used in the Examples:
DCM - Dichloromethane
DIPE - Diisopropylether
NBS - N-Bromosuccinimide
THF - Tetrahydrofuran
DMF - N,N-Dimethylformamide Unless otherwise stated $^1$H NMR and $^{13}$C NMR spectra were recorded on a Bruker AC-250 spectrometer at 250 MHz and 62.9 MHz respectively using CDCl$_3$ as a solvent and internal reference and are reported as delta ppm from TMS.

EXAMPLE 1

N-1-Methylhexyl 4—(1 H-2-methylbenzimidazolylmethyl)benzenesulphonamide

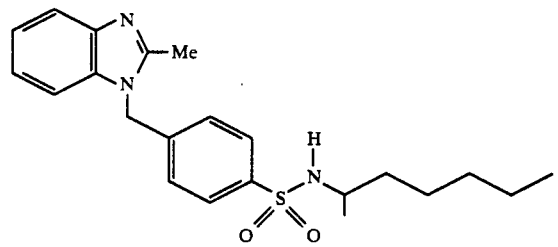

(A) 4-Bromomethylbenzenesulphonyl Chloride

To a solution of p-toluenegulphonyl chloride (50.0 g, 0.26 mol) in benzene (150 ml) and NBS (46.7 g, 0.26 mol) heated at reflux was added 2,2'-azobis (2-methylpropionitrile) (100 mg). The mixture was heated at reflux for 12 h and allowed to cool to room temperature. The white precipitate of succinimide that formed was separated and discarded. The filtrate was taken up in DCM (200 ml) and washed with water (3×100 ml) followed by brine (100 ml) and dried over anhydrous sodium sulphate. Filtration, concentration and subsequent crystallisation (from DIPE) gave in two crops 4-bromomethylbenzenesulphonyl chloride (46.3 g, 66%) as a white crystalline solid.

m.p. 75°–76° C.

delta$_H$ 8.02 (2 H, d, J 8.5 Hz), 7.64 (2 H, d, J 8.5 Hz), 4.52 (2 H, s).

(b) N-1-Methylhexyl 4-bromomethylbenzenesulphonamide

To a solution of 2-aminoheptane (1.67 ml, 0.011 mol) and triethylamine (1.55 ml, 0.011 mol) in dry THF (100 ml) was added powdered 4-bromomethylbenzenesulphonyl chloride (3.0 g, 0.011 mol) in one portion. The mixture was stirred for 3 h at room temperature. The reaction mixture was treated with saturated ammonium chloride (60 ml), extracted with ethyl acetate (3×80 ml), the organics combined and washed with water (50 ml) and brine (50 ml), dried over anhydrous sodium sulphate, filtered and evaporated. The resulting oil was purified by chromatography (silica: 1:2 hexane:ethyl acetate) to give N-1-methylhexyl 4-bromomethylbenzenesulphonamide (1.45 g, 39%) as a pale yellow oil.

delta$_h$ 7.85 (2 H, d, J 8.3 Hz), 7.53 (2 H, d, J 8.3 Hz), 4.50 (2 H, s), 4.27 (1 H, d, i 8.0 Hz), 3.40-3.24 (1 H, m), 1.40-1.08 (8 H, m), 1.06 (3 H, d, J 6.6 Hz), 0.83 (3 H, t, J 6.6 Hz).

(c) N-1-Methylhexyl-4—(1 H-2-methylbenzimidazolylmethyl)benzene sulphonamide Sodium hydride (60% dispersion in oil: 176 mg, 4.4 mmol) was added to a stirred solution of 2-methylbenzimidazole (581 mg, 4.4 mmol) in dry THF (150 ml) under argon at room temperature. After 0.5 h a solution of N-1-methylhexyl 4-bromomethylbenzenesulphonamide (1.45 g, 4.3 mmol) in dry THF (8 ml) was added. The mixture wag stirred for 8 h, water (60 ml) was added and the product extracted with ethyl acetate (3×60 ml). The combined organic layers were washed with water (2×50 ml), dried over anhydrous sodium sulphate, filtered and the solvent removed. Chromatography (silica: 5% methanol in chloroform) gave N-1-methylhexyl 4—(1 H-2-methylbenzimidazolylmethyl) benzenesulphonamide (1.06 g, 60%) as a white crystalline solid.

i.r. (KBr) 2990-2800, 1325, 1160 cm$^{-1}$.

delta$_H$ 7.80-7.70 (3 H, m), 7.30-7.04 (5 H, m), 5.35 (2 H, s), 4.94 (1 H, d, J 8.2 Hz), 3.34-3.20 (1 H, m), 2.54 (3H, s), 1.39-1.02 (8 H, m), 1.00 (3 H, d, J 6.5 Hz), 0.80 (3H, t, J 6.5 Hz).

delta$_C$ 151.59, 142.57 141.23, 140.24, 135.09, 127.64, 122.48, 122.26, 119.25, 109.00, 50.11, 46.54, 37.27, 31.26, 25.09, 22.34, 21,71, 13.83.

EXAMPLES 2-4

The compounds of Examples 2 to 4 were prepared by the method of Example 1 starting from the appropriate amine.

2. N-1,4-Dimethylpentyl 4—(1 H-2-methylbenzimidazolylmethyl)benzenesulphonamide

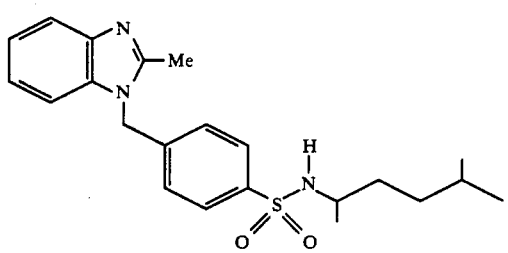

White Crystalline solid (11% yield for last step after chromatography (silica: 5% methanol in chloroform)): m.p. 146° C.

Analysis Calculated For $C_{22}H_{29}N_3SO_2.0.4H_2O$

Requires C 64.96 H 7.38 N 10.33.
Found C 65.05 H 7.22 N 10.32.

delta$_H$ 7.83-7.71 (3 H, m), 7.30-7.07 (5H, M), 5.36 (2H, s), 4.87 (1 H, d, J 8.3 Hz), 3.32-3.20 (1 H, m, H), 2.55 (3H, s), 1.42-1.22 (3H, m), 1.14-0.90 (2H, m), 1.00 (3H, d, i 6.5 Hz), 0.80-0.70 (6H, m).

delta$_C$ 151.59, 142.59, 141.26, 140.47, 135.13, 127.68, 126.67, 122.53, 122.29, 119.29, 109.03, 50.39, 46.56, 35.11, 34.49, 27.60, 22.34, 21.74.

3. N-1-Methyl-3-phenylpropyl 4—(1 H-2-methylbenzimidazolylmethyl)benzenesulphonamide

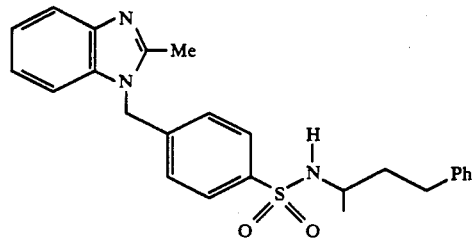

White crystalline solid (14% yield for last step after chromatography (silica: 5% methanol in chloroform) m.p. 165°-166° C.

Analysis Calculated For $C_{25}H_{27}N_3SO_2$

Requires C 69.26 H 6.28 N 9.69.
Found C 69.01 H 6.29 N 9.65.

i.r. (KBr) 1320, 1160 cm$^{-1}$.

delta$_H$ 7.83-7.74 (3 H, m), 7.33-7 00 (10 H, m), 5.37 (2H, s), 4.87-4.80 (1 H, m), 3.44-3.28 (1 H, m), 2.63-2.40 (2 H, m), 2.54 (3 H, s), 1.67 (2H, q, J 7.5 Hz), 1.05 (3 H, d, J 6.6 Hz).

4. N-Diphenylmethyl 4—(1H-2-methylbenzimidazolylmethyl)benzenesulphonamide

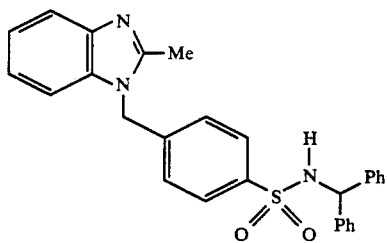

Pale brown crystalline solid (6% yield for last step after chromatography (silica: 5% methanol in chloroform)): m.p. 248°-250° C.

Analysis Calculated for $C_{28}H_{25}N_3SO_2$.

Requires C 71.92 H 5.39 N 8.99 S 6.89.
Found C 71.83 H 5.47 N 8.85 S 6.85.

delta$_H$ (d6-DMSO) 8.78 (1 H, br d), 7.60-6.98 (18 H, m), 5.51 (1 H, br d), 5.45 (2 H, s), (2.46 (3H, s).

EXAMPLE 5

N-Diphenylmethyl-N-methyl 4-(1 H-2-methylbenzimidazolylmethyl)benzenesulphonamide

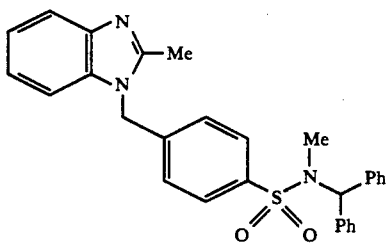

A suspension of sodium hydride (60% dispersion in oil: 13 mg, 0.33 mmol) in dry THF (20 ml) under argon at 0° C. was treated with a solution of N-diphenylmethyl 4-(1 H-2-methylbenzimidazolylmethyl) benzenesulphonamide (137 mg, 0.29 mmol) in dry THF (3 ml). The resulting solution was quenched with excess methyl iodide (2 ml) at 0° C. The stirred mixture was allowed to warm up to room temperature over 1 h. The reaction mixture was partitioned between ethyl acetate and ammonium chloride, the organic layer washed with brine, dried over anhydrous magnesium sulphate, filtered and the solvent removed. The crude product was purified by preparative thin layer chromatography (2 Mm silica plate; 1% methanol in DCM) to yield N-diphenylmethyl-N-methyl, 4-(1 H-2-methylbenzimidazolylmethyl) benzenesulphonamide (64 mg, 46%) as a colourless oil. delta$_H$ 7.80-7.78 (1 H, m), 7.65 (2 H, d, J 8.3 Hz), 7.38-7.00 (15 H, m), 6.42 (1 H, s), 5.36 (2 H, s), 2.70 (3H, s), 2.58 (3H, s)

EXAMPLE 6

N-1,2-Diphenylethyl 4-(1 H-2-methylbenzimidazolylmethyl)benzenesulphonamide

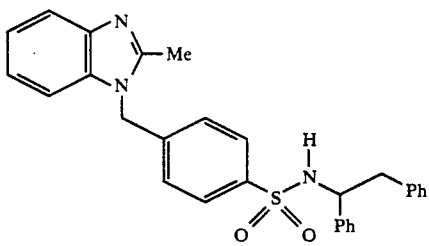

(a) N-1,2-Diphenylethyl 4-bromomethylbenzenesulphonamide

A solution of 4-bromomethylbenzenesulponyl chloride (6.82 g, 25 mmol) in dry THF (30 ml) was added to a stirred mixture of 1,2-diphenylethylamine (4.9 ml, 25 mmol) and triethylamine (3.8 ml, 25 mmol) in dry THF (20 ml) at room temperature under argon. The mixture was stirred overnight and the solvent removed under reduced pressure. The residue was extracted with ethyl acetate (100 ml), the organics washed with water (100 ml) and brine (100 ml), dried over anhydrous magnesium sulphate, filtered and concentrated. Chromatography (silica: 10% methanol in DCM) followed by crystallisation from ethyl acetate/hexane gave N-1,2-diphenylethyl 4-bromomethylbenzenesulphonamide (7.6 g, 69%) as a white crystalline solid.

delta$_H$ 7.55-6.90 (14 H, m), 5.45 (1 H, d, J 6.1 Hz), 4.54 (2 H, s), 3.91-3.89 (1 H, m), 3.03-2.98 (2 H, m).

(b) N-1,2-Diphenylethyl 4-(1 H-2-methylbenzimidazolylmethyl)benzenesulphonamide

N-1,2-Diphenylethyl 4-(1 H-2-methylbenzimidazolylmethyl)benzenesulphonamide was prepared by the method of Example 1 Step (c) starting from N-1,2-diphenylethyl 4-bromomethylbenzenesulphonamide.

White crystalline solid (26% yield for last step after chromatography (silica: 1% methanol in DCM)): m.p. 168°-169.5° C.

Analysis Calculated For $C_{29}H_{27}N_3SO_2.0.8H_2O$
Requires C 70.22 H 5.81 N 8.47.
Found C 70.34 H 5.68 N 8.25.
delta$_H$ 7.85-7.80 (1 H, m), 7.52-6.85 (17 H, m), 5.33 (2 H, s), 4.94 (1 H, d, J 6.5 Hz), 4.57 (1 H, dt, J 7.0, 6.5 Hz), 3.97 (2 H, dd, J 7.5, 6.2 Hz), 2. 68 (3H, s)

EXAMPLE 7

N-(S)-1-Benzyl-2-methoxyethyl 4-(1 H-2-methylbenzimidazolylmethyl)benzenesulphonamide

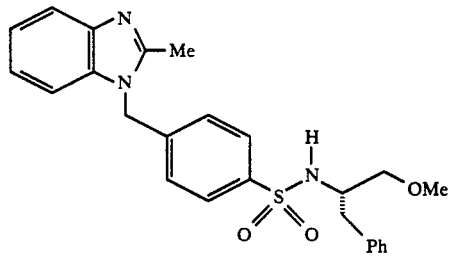

(a) (S)-1-Benzyl-2-methoxyethylamine

Sodium hydride (60% dispersion in oil: 322 mg, 8.1 mmol) was added to a stirred solution of N-tert-butoxycarbonyl-(S)-1-benzyl-1-aminoethan-2-ol (2.02 g, 8.1 mmol) in dry THF (50 ml) at 0° C. under argon. The mixture was stirred for 10 min. and methyl iodide (3 ml) added. The reaction mixture was allowed to warm to room temperature and stirred for 1 h. Saturated ammonium chloride (80 ml) was added and the mixture extracted with ethyl acetate (2×100 ml). The combined organic extracts were dried over anhydrous sodium sulphate, filtered and concentrated to give a clear oil. The oil was dissolved in DCM (40 ml) and treated with excess trifluoroacetic acid.(6.2 ml) at 0° C. The mixture was allowed to warm up to room temperature and was stirred for 2 h. The mixture was washed with aqueous sodium hydrogen carbonate and brine, and dried over anhydrous sodium sulphate. Filtration and evaporation gave (S)-1-benzyl-2-methoxyethylamine (620 mg, 47%) as a colourless oil.

delta$_H$ 7.21-7.14 (5 H, m), 3.42-2.47 (7 H, m), 3.34 (3 H, s).

(b) N-(S)-1-Benzyl-2-methoxyethyl 4-bromomethylbenzenesulphonamide

N-(S)-1-Benzyl-2-methoxyethyl 4-bromomethylbenzenesulphonamide was prepared by the method of Example 1 Step (b) employing (S)-1-benzyl-2-methoxyethylamine in lieu of 2-aminoheptane.

delta$_H$ 7.74 (2 H, d), 7.42 (2 H, d), 7.24–7.20 (3H, m), 7.08–7.01 (2 H, m), 5.11 (1 H, d), 4.47 (2 H, s), 3.55 (1 H, m), 3.34–3.17 (2 H, m), 3.28 (3H, s), 2.91–2.71 (2 H, m).

(c) N-(S)-1-Benzyl-2-methoxyethyl 4-(1 H-2-methylbenzimidazolylmethyl)benzenesulphonamide 1-N-(S)-1-Benzyl-2-methoxyethyl-4-(1 H-2-methylbenzimidazolylmethyl) benzenesulphonamide was prepared by the method of Example 1 Step (c) employing N-(S)-1-benzyl-2-methoxyethyl 4-bromomethylbenzenesulphonamide in lieu of N-1-methylhexyl 4-bromomethylbenzenesulphonamide.

White crystalline solid (34% yield for last step after chromatography (silica: 5% methanol in chloroform)): m.p. 134° C.

i.r. (KBr) 1330, 1150 cm$^{-1}$.

delta$_H$ 7.74 (1 H, d, J 7.1 Hz), 7.63 (2 H, d, J 8.3 Hz), 7.30–6.93 (10 H, m), 5.33 (2 H, s), 5.17 (1 H, d, J 7.9 Hz), 3.58–3.40 (1 H, m), 3.23 (1 H, dd, i 9.5, 3.9 Hz), 3.20 (3H, s), 3.16 (1 H, dd, J 9.5, 4.6 Hz), 3.84–3.64 (2 H, m), 2.55 (3H, s).

delta$_C$ 151.54, 142.61, 140.44, 137.07, 135.07, 129.21, 128.43, 127.60, 126.61, 126.50, 122.49, 122.30, 119.32, 72.65, 58.79, 54.84, 46.53, 38.23.

EXAMPLE 8

N-1,2-Diphenylethyl-N-methyl 4-(1 H-2-methylbenzimidazolylmethyl)benzenesulphonamide

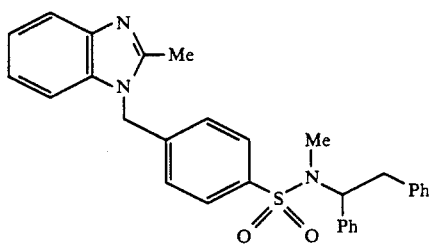

N-1,2-Diphenylethyl-N-methyl 4-(1 H-2-methylbenzimidazolylmethyl)benzenesulphonamide was prepared by the method of Example 5 starting from N-1,2-Diphenylethyl 4-(1 H-2-methylbenzimidazolylmethyl)-benzenesulphonamide Colourless oil (13% yield after chromatography (silica: 1% methanol in DCM)).

delta$_H$ 7.80–7.76 (1 H, m), 7.40–7.00 (15 H, m), 6.92 (2 H, d, J 8.4 Hz), 5.53 (1 H, dd, J 9.0, 6.8 Hz), 5.27 (2 H, s), 3.22 (1 H, dd, J 14.1, 6.8 Hz), 3.01 (1 H, dd, J 14.1, 9.0 Hz), 2.62 (3H, s), 2.54 (3H, s).

EXAMPLES 9–11

The compounds of Examples 8 to 10 were prepared by the method of Example 1 starting from the appropriate amine.

9. N-1-Benzyl-2-phenylethyl 4-(1 H-2-methylbenzimidazolylmethyl)benzenesulphonamide

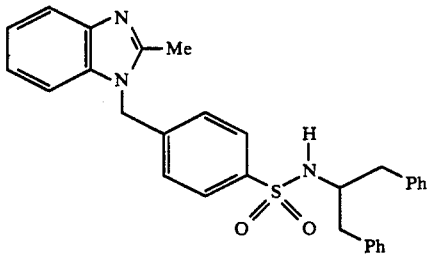

White crystalline solid (5% for last step after chromatography (silica: 2% methanol in DCM)): m.p. 90° C.

delta$_H$ 7.80–7.78 (1 H, m), 7.38 (2 H, d, J 8.4 Hz), 7.36–6.98 (13H, m), 6.93 (2 H, d, J 8.4 Hz), 5.31 (2 H, s), 4.57 (1 H, d, i 7.4 Hz), 3.64–3.50 (1 H, m), 2.82 (2 H, dd, J 10.7, 6.2 Hz), 2.70 (2 H, dd, i 13.8, 6.9 Hz), 2.57 (3H, s).

delta$_C$ 151.57, 144.0, 143.0, 140.11, 139.80, 137.04, 129.40, 128.50, 127.52, 126.62, 126.51, 122.61, 122.45, 119.41, 109.06, 56.66, 46.55, 41.02.

10. N-2,2-Diphenylethyl 4-(1 H-2-methylbenzimidazolylmethyl)benzenesulphonamide

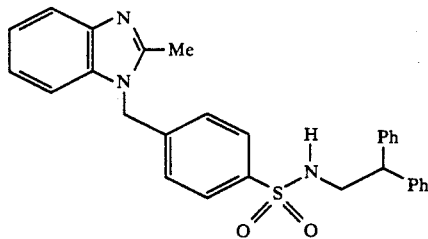

White crystalline solid (13% yield for last step after chromatography (silica: 3% methanol in DCM) and crystallisation from ethyl acetate/hexane): m.p. 137°–140° C.

Analysis Calculated For C$_{29}$H$_{27}$N$_3$SO$_2$.0.3H$_{20}$

Requires C 71.52 H 5.71 N 8.63.

Found C 71.60 H 5.72 N 8.35.

i.r. (CHCl$_3$) 3300, 1340, 1160 (cm$^{-1}$.

delta$_H$ 7.74 (2 H, m), 7.21 (16 H, m), 5.41 (2 H, s), 4.39 (1 H, t, J 6.1 Hz), 4.05 (1 H, t, J 7.9 Hz), 3.36 (2 H, dd, J 6.2, 1.8 Hz), 2.60 (3H, s).

11. N-3,3-Diphenylpropyl 4-(1 H-2-methylbenzimidazolylmethyl)benzenesulphonamide

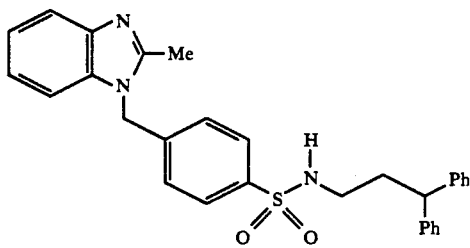

White crystalline solid (19% yield for last step after chromatography (silica: 1% methanol in DCM)): m.p. 178° C.

delta$_H$ 7.74–7.60 (3H, m), 7.28–7.06 (13H, m), 7.03 (2 H, d, J 8.3 Hz), 6.01 (1 H, t, J 5.9 Hz), 5.26 (2 H, s), 3.94 (1 H, t, J 7.8 Hz), 2.97–2.82 (2 H, m), 2.49 (3H, s), 2.30–2.18 (2 H, m).

EXAMPLE 12

N-Isopropyl-N-3,3-di(4-methoxy)phenyl-2-propenyl 4-(1 H-2-methylbenzimidazolylmethyl) benzenesulphonamide

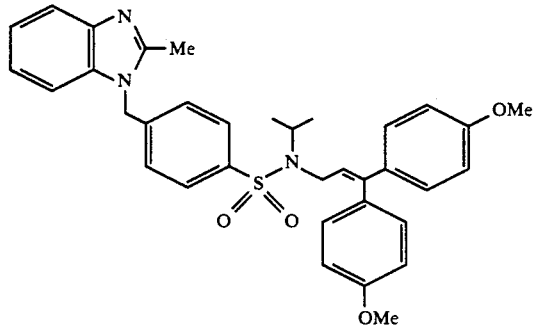

(a) 3-Hydroxy-3,3-di(4-methoxyphenyl)propanenitrile

Acetonitrile (3.2 ml, 0.058 mol) was added dropwise to a solution of lithium diisopropylamide (1.5 M in THF, 36.7 ml, 0.055 mol) stirred at −78° C. under argon. After 5 min. a solution of 4,4'-dimethoxybenzophenone (10.0 g, 0.048 mol) in dry THF (130 ml) was added slowly. The mixture was allowed to warm up to −35° C. and after 20 min. was quenched by the cautious dropwise addition of a solution of acetic acid (3.0 g) in water (6 ml). Brine (50 ml) was added, the organic layer separated washed with brine (50 ml) and the combined aqueous phases were extracted with DCM (2×50 ml). The combined organics were dried over anhydrous magnesium sulphate, filtered and concentrated. The residue was crystalised from ethyl acetate to give 3-hydroxy-3,3-di(4-methoxyphenyl)propanenitrile (10.12 g, 85%) as a white crystalline solid.
m.p. 101.5° C.

delta$_H$ 7.30 (4H, m), 6.88 (4H, m), 3.80 (6H, s), 3.21 (2 H, s), 2.84,( 1H, s).

(b) 3,3-Di(4-methoxyphenyl)-2-propenenitrile

Thionyl chloride (2.18 g, 0.018 mol) was slowly added to a stirred solution of 3-hydroxy-3,3-di(4-methoxyphenyl)propanenitrile (4.0 g, 0.014 mol) in pyridine (30 ml) cooled in an ice-salt bath. After the addition was complete the mixture was allowed to warm up to room temperature and stirred for 2 h. ice cold water (100 ml) was added and the mixture extracted with DCM (2×100 ml) The combined organics were washed with 3M hydrochloric acid (1×50 ml, 1×5 ml), brine (50 ml), dried over anhydrous sodium sulphate, filtered and evaporated to yield crude 3,3-di(4-methoxyphenyl)-2-propenenitrile (2.95 g, 79%) which was used directly in the next step.

delta$_H$ 7.40 (2 H, d, J 8.8 Hz), 7.26 (2 H, d, J 8.7 Hz), 6.96 (2 H, d, J 8.8 Hz), 6.89 (2 H, d, J 8.8 Hz), 5.55 (1 H, s), 3.87 (3H, s), 3.85 (39, s).

(c) 3,3-Di(4-methoxyphenyl)-2-propenal

Diisobutyldluminiumhydride (1 M solution in toluene; 14.42 ml, 0.014 mol) was added dropwise to a stirred solution of crude 3,3-di(4-methoxyphenyl)-2-propanenitrile (2.91 g, 0.011 mol) in dry toluene (30 ml) at −40° C. under argon. After stirring for 1 h at −40° C. the reaction was allowed to warm to −12° C. over 45 min and 0.5M sulphuric acid (46 ml) was added slowly. This mixture was stirred at room temperature for 48 h. The aqueous phase was separated and extracted with toluene (2×60 ml) The combined organic phases were washed with water (50 ml), brine (50 ml) and dried over anhydrous sodium sulphate. Filtration and evaporation gave 3,3-di(4-methoxyphenyl)-2-propenal (2.8 g, 9 6% as a colourless oil which was used directly in the next step.

delta$_H$ 9.48 (1 H, d, i 8.2 Hz), 7.31 (2 H, d, J 8.9 Hz), 7.23 (2 H, d, J 8.7 Hz), 6.95 (2 H, d, J 8.7 Hz), 6.89 (2 H, d, i 9.0 Hz), 6.50 (1 H, d, J 8.0 Hz), 3.87 (6 H, s).

(d) N-Isopropyl 3,3-di(4-Methoxyphenyl)-2-Propenyl Amine

Isopropylamine was added to a solution of 3,3-di(4-methoxyphenyl)-2-propenal (1.0 g, 3.7 mmol) in dry ethyl acetate (30 ml). Activated 4-A molecular sieves were added and the mixture stirred overnight. The mixture was filtered, washed with water (10 ml), brine (10 ml), dried over anhydrous sodium sulphate, and filtered through a pad of silica. Concentration gave N-isopropyl 3,3-di(4-methoxyphenyl)-2-propenyl imine (0.90 g, 78%) as a yellow oil which was used directly in the next step.

Sodium cyanoborohydride (0.19 g, 3.0 mmol) was added to a solution of N-isopropyl 3,3-di(4-methoxyphenyl)-2-propenyl imine (0.90 g, 2.8 mmol) in methanol (30 ml). The mixture was stirred and 1M hydrochloric acid was added until a PH of 5 was attained. After 6 h water (50 ml) was added and the mixture extracted with DCM (3×70 ml). The combined organic extracts were dried over anhydrous sodium sulphate, filtered and evaporated to give crude N-isopropyl 3,3-di(4-methoxyphenyl)-2-propenyl amine (0.64 g, 70%) as a yellow oil which was used directly in the next step.

delta$_H$ 7.16 (2 H, d, J 8.8 Hz), 7.08 (2 H, d, J 8.7 Hz), 6.88 (2 H, d, 8.7 Hz), 6.78 (2 H, d, J 8.8 Hz), 6.02 (1 H, t, J 6.8 Hz), 3.82 (3 H, s), 3.77 (3 H, s), 3.31 (2 H, d, J 6.9 Hz), 2.81 (1 H, m), 1.01 (3 H, s), 0.99 (3 H, s).

(e) N-Isopropyl-N-3,3-di(4-methoxy)phenyl-2-propenyl 4-(1 H-2-methylbenzimidazolylmethyl) benzenesulphonamide N-Isopropyl-N-3,3-di-(4-methoxy)phenyl-2-propenyl 4-(1 H-2-methyl-benzimidazolylmethyl) benzenesulphonamide was prepared following the method of Example 1 starting from crude N-isopropyl 3,3-di(4-methoxyphenyl)-2-propenyl amine.

Amorphous solid (chromatography (silica: 2% methanol in DCM)):

delta$_H$ 7.80–7.66 (3H, m), 7.30–7.00 (9 H, m), 6.90 (2 H, d), 6.79 (2 H, d), 5.91 (1 H, t, J 6.4 Hz), 5.34 (2 H, S), 4.18–4.03 (1 H, m), 3.90–3.76 (2 H, m), 3.81 (3 H, s), 3.78 (3H, s), 2.52 (3 H, s), 0.93 (6H, d, J 6.8 Hz).

delta$_C$ 159.06, 158.87, 151.0, 142.0, 141.50, 141.28, 140.13, 135.0, 134.38, 131.15, 130.84, 128.45, 127.63, 126.61, 124.95, 122.50, 122.28, 119.28, 113.59, 113.42, 108.98, 55.22, 55.17, 49.59, 46.53, 41.76, 21.21.

EXAMPLE 13

N-2-(3,4-Dimethoxy)phenylethyl 4-(1 H-2-methylbenzimidazolylmethyl)benzenesulphonamide

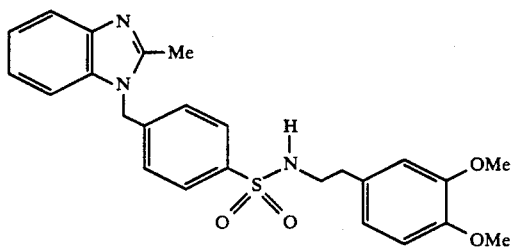

N-2-(3,4-Dimethoxy)phenylethyl 4-(1 H-2-methylbenzimidazolylmethyl) benzenesulphonamide was prepared following the method of Example 1 starting from 2-(3,4-Dimethoxy)phenylethylamine.

White crystalline solid (6% yield for last step after chromatography (silica: 5% methanol in DCM) and crystallisation from ethyl acetate/hexane): m.p. 193° C.

Analysis Calculated For C$_{25}$H$_{27}$N$_3$SO$_4$.

Requires C 63.27 H 5.95 N 8.85.
Found C 63.31 H 5.71 N 8.62.
i.r. (CHCl$_3$) 3075, 1600, 1330, 1160 cm$^{-1}$.

delta$_H$ 7.75 (3H, m), 7.22 (5H, m), 6.75 (1 H, d, J 8.2 Hz), 6.61 (1 H, d, J 1.9 Hz), 6.58 (1 H, s), 5.39 (2 H, 5), 4.43 (1 H, t, i 6.2 Hz), 3.84 (3H, s), 3.80 (3H, s), 3.19 (2 H, dt, J 6.7, 6.4 Hz), 2.71 (2 H, t, J 6. 8 Hz), 2. 5 8 (3H, s)

EXAMPLE 14

N-Cyclopentyl-N-2-(3,4-dimethoxy)phenylethyl 4-(1 H-2-methylbenzimidazolylmethyl)benzenesulphonamide

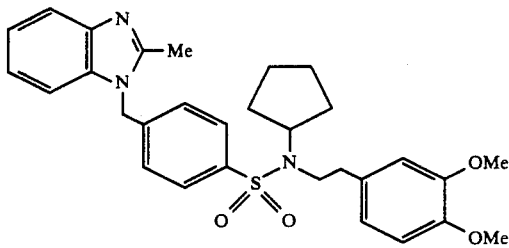

N-Cyclopentyl-N-2-(3,4-dimethoxy)phenylethyl 4-(1 H-2-methylbenzimidazolylmethyl) benzenesulphonamide was prepared starting from 2-(3,4-dimethoxy)phenylethylamine and cyclopentanone following the method of Example 12 Steps (d) and (e).

Amorphous solid (9% yield for last step after chromatography (silica: 1% methanol in DCM)):

delta$_H$ 7.81–7.71 (3H, m), 7.30–7.09 (5H, m), 6.80–6.69 (3H, m), 5.35 (2 H, s), 4.22–4.04 (1 H, m), 3.86 (3H, s), 3.83 (3H, s), 3.23–3.11 (2 H, m), 3.00–2.86 (2 H, m), 2.53 (3H, s), 1.70–1.18 (8 H, m).

delta$_C$ 151.53, 148.87, 147.65, 142.52, 140.41, 140.29, 135.07, 131.28, 127.78, 126.70, 122.45, 122.23, 120.58, 119.23, 112.12, 111.28, 109.00, 59.16, 55.84, 46.51, 46.13, 38.15, 29.23, 23.28.

EXAMPLE 15

(A) N-Cyclopentyl-N-2-(3,4-dimethoxy)phenylethyl 4-(3H-imidazo-[4,5-c]pyridylmethyl) benzenesulphonamide and (B) N-cyclopentyl-N-2-(3,4-dimethoxy)phenylethyl 4-(1 H-imidazo[4,5-c]pyridylmethyl)benzenesulphonamide

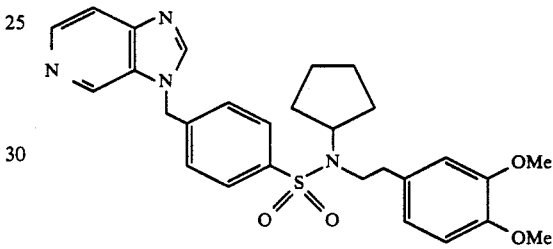

A

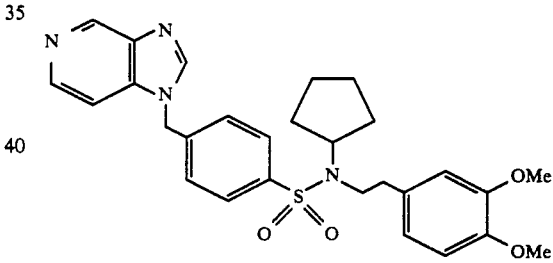

B

N-Cyclopentyl-N-2-(3,4-dimethoxy)phenylethyl 4-(1 H-imidazo[4,5c]-pyridylmethyl)benzenesulphonamide was prepared by the method of Example 14 utilising imidazo[4,5c]pyridine in the final step in lieu of 2-methylbenzimidazole.

Regioisomer (A): Amorphous solid (3% yield after chromatography (silica: 2% methanol in DCM)):
i.r. (CDCl$_3$) 1335, 1140 cm$^{-1}$.

delta$_H$ 8.68 (1 H, d, J 0.9 Hz), 8.47 (1 H, d, J 5.7 Hz), 8.10 (1 H, s), 7.83 (2 H, d, J 8.4 Hz), 7.75 (1 H, dd, J 5.5, 0.9 Hz), 7.29 (2 H, d, J 8.5 Hz), 6.84–6.70 (3H, m), 5.52 (2 H, S), 4.20–4.06 (1 H, m), 3.88 (3H, s), 3.85 (3H, s), 3.25–3.14 (2 H, m), 2.99–2.89 (2 H, m), 1.73–1.20 (8 H, m).

Regioisomer (B): Amorphous solid (3% yield):

delta$_H$ 9.16 (1 H, s), 8.39 (1 H, d, J 5.6 Hz), 8.03 (1 H, s), 7.83 (2 H, d, J 8.3 Hz), 7.24 (2 H, d, J 8.3 Hz), 7.17 (1 H, d, J 5.6 Hz), 6.83–6.68 (3H, m), 5.45 (2 H, s), 4.21–4.04 (1 H, m), 3.87 (3H, s), 3.85 (3H, s), 3.23–3.13 (2 H, m), 3.00–2.88 (2 H, m), 1.72–1.20 (8 H, m).

EXAMPLE 16

N-Cyclohexyl-N-2-(3,4-dimethoxy)phenylethyl 4-(1 H-2-meth 1-benzimidazolylmethyl) benzenesulphonamide

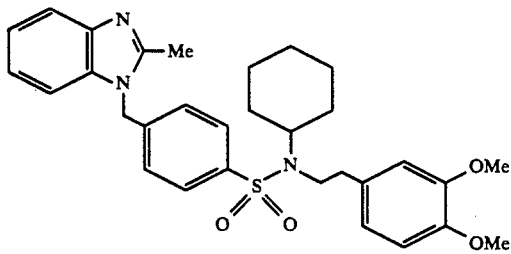

N-Cyclohexyl-N-2-(3,4-dimethoxy)phenylethyl 4-(1 H-2-methylbenzimidazolylmethyl) benzenesulphonamide was prepared by the method of Example 15 starting from cyclohexanone in lieu of cyclopentanone.

Amorphous solid (chromatography (silica: 1% methanol in DCM)):

delta$_H$ 7.81–7.72 (3H, m), 7.30–7.10 (5H, M), 6.81–6.68 (3H, m), 5.37 (2 H, s), 3.87 (3H, s), 3.85 (3H, s), 3.70–3.53 (1 H, m), 3.30–3.20 (2 H, m), 2.94–2.82 (2 H, m), 2.55 (3H, s), 1.80–0.90 (10H, m).

delta$_C$ 151.56, 148.94, 147.72, 142.62, 141.39, 140.30, 135.13, 131.38, 127.62, 126.77, 122.52, 122.33, 120.61, 119.35, 112.12, 111.34, 109.02, 58.12, 55.92, 46.62, 45.80, 35.40, 31.74, 25.98, 25.23.

EXAMPLE 17

(A) N-1,2-Diphenylethyl 4-(3H-2-methylimidazo[4,5-c]pyridylmethyl) benzenesulphonamide and (B) N-1,2-diphenylethyl 4-(1 H-2-methyliniidazo [4,5-c]pyridylmethyl)benzenesulphonamide

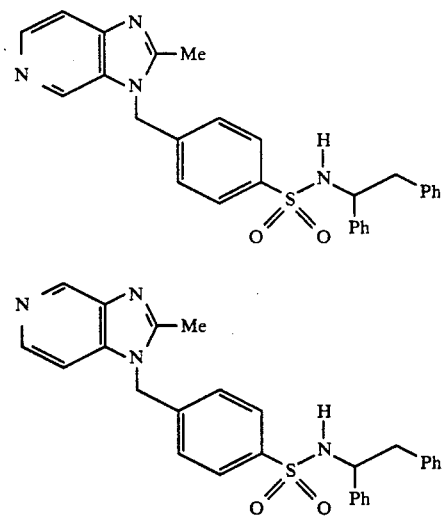

Sodium hydride (60% dispersion in oil: 0.77 g, 19.4 mmol) was added to a stirred solution of 2-methylimidazo(4,5-c]pyridine (2.35 g, 17.7 mmol) in dry DMF (25 ml) under argon. The mixture was stirred for 1 h at room temperature and a solution of N-1,2-diphenylethyl 4-bromomethylbenzenesulphonamide (7. 6 g, 17.7 mmol) in dry THF (100 ml) was added. The reaction mixture was stirred for 48 h and the solvent removed under reduced pressure. The residue was extracted with ethyl ether (100 ml) and the organic extracts washed with water (100 ml) and brine (100 ml), dried over anhydrous magnesium sulphate, filtered and evaporated. Chromatography (silica: 4% methanol in DCM) gave regioisomer (A) N-1,2-diphenylethyl 4-(3H-2-methylimidazo[4,5-c]pyridylmethyl)benzenesulphonamide followed by regioisomer (B) N-1,2-diphenylethyl 4-(1 H-2-methylimidazo[4,5-c]pyridylmethyl)benzenesulphonamide.

Regioisomer (B): Colourless oil (45 mg, 0.5%).

delta$_H$ .9.04 (1 H, s), 8.41 (1 H, s), 7.44 (2 H, d, J 8.3 Hz), 7.14–6.84 (13H, m) , 5.73 (1 H, d, J 6.8 Hz) , 5.27 (2 H, s) , 4.57 (1 H, q, J 7.0 Hz), 2.99 (2 H, d, J 7.2 Hz), 2.56 (3H, s).

delta$_C$ 153.35, 141.99, 141.89, 140.70, 140.17, 139.98, 139.04, 136.23, 129.24, 128.43, 128.18, 127.80, 127.38, 126.80, 126.65, 126.27, 104.69, 59.31, 46.70, 44.06, 13.95.

EXAMPLE 18

(A) N-1,2-Diphenylethyl-N-methyl 4-(3H-2-methylimidazo[4,5-cl-pyridylmethyl) benzenesulphonamide and (B) N-1,2-diphenylethyl-N-methyl 4-(1 H-2-methylimidazo[4,5-c]pyridylmethyl)benzenesulphonamide

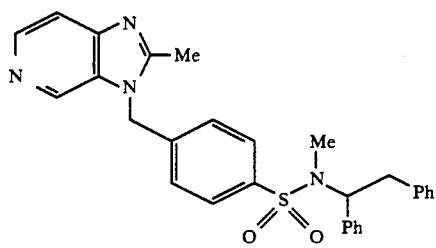

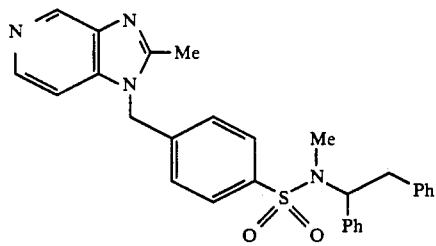

(a) N-Methyl-N-1,2-diphenylethyl 4-bromomethylbenzenesulphonamide

Sodium hydride (60% dispersion in oil: 190 mg, 4.7 mmol) was added to a stirred solution of N-1,2-diphenylethyl 4-bromomethylbenzenesulphonamide (2.00 g, 4.7 mmol) in dry THF (50 ml) at 0° C. under argon. Methyl iodide (0.6 ml, 9.3 mmol) was added immediately to the reaction mixture. The mixture was stirred for 48 h at ambient temperature. Saturated aqueous ammonium chloride (50 mi) was added and the mixture extracted with ethyl acetate (2×80 ml). The combined organics were washed with brine (50 ml), dried over anhydrous sodium sulphate, filtered and concentrated to give N-methyl-N-1,2-diphenylethyl 4-bromomethylbenzenesulphonamide as an orange oil which was used directly in the next step.

delta$_H$ 7.45–7.10 (14 H, m), 5.57 (1 H, dd, J 8.9, 6.9 Hz), 4.39 (2 H, s), 3.29 (1 H, dd, J 14.1, 6.8 Hz), 3.08 (1 H., dd, i 14.1, 9.0 Hz), 2.69 (3H, s).

(b) (A) N-1,2-Diphenylethyl-N-methyl 4-(3H-2-methylimidazo[4,5-c]-pyridylmethyl)benzenesulphonamide and (B) N-1,2-diphenylethyl-N-methyl 4-(1 H-2-methylimidazo[4,5-c]pyridylmethyl)benzenesulphonamide were prepared by the procedure of Example 17 employing N-methyl-N-1,2-diphenylethyl 4-bromomethylbenzenesulphonamide in lieu of N-1,2-diphenylethyl 4-bromomethylbenzenesulphonamide.

Regioisomer (A): Amorphous solid (9% yield for last step after chromatography (silica: 4–7% methanol in DCM)).

i.r. (CDCl$_3$) 2205, 1325, 1150 cm$^{-1}$.

delta$_H$ 8-54 (1 H, s), 8.41 (1 H, d, i 5.6 Hz), 7.61 (1 H, d, J 5.2 Hz), 7.29–7.15 (7H, m), 7.04 (4H, m), 6.98 (1 H, m), 6.87 (2 H, d, J 8.3 Hz), 5.48 (1 H, dd, J 9.2, 6.6 Hz), 5.30 (2 H, s), 3.17 (1 H, dd, J 14.0, 6.5 Hz), 2.97 (1 H, dd, J 14.1, 9.2 Hz), 2.57 (3H, s), 2.53 (3H, s).

delta$_C$ 154.87, 147.62, 142.14, 139.67, 138.94, 137.87, 137.60, 32.75, 132.21, 128.771, 128.26, 127.65, 126.36, 126.22, 113.84, 1.28, 46.72, 36.87, 28.64.

Regioisomer (B) : White crystalline solid from ethyl acetate (11% yield): m.p. 173° C.

Analysis Calculated For C$_{29}$H$_{28}$N$_4$O$_2$S

Requires C 70.14 H 5.68 N 11.28.
Found C 69.96 H 5.73 N 11.18.
i.r. (CDCl$_3$) 2205, 1725, 1330 cm$^{-1}$.

delta$_H$ 9.01 (1 H, s), 8.33 (1 H, d, J 5.6 Hz), 7.30–7.00 (14 H, m), 6.88 (1 H, d, J 9.3 Hz), 5.50 (1 H, dd, J 8.9, 6.9 Hz), 5.27 (2 H, s), 3.20 (1 H, dd, J 14.1, 6.8 Hz), 2.98 (1 H, dd, J 14.1, 9.0 Hz), 2.59 (3H, s), 2.52 (3H, s).

EXAMPLE 19

(A) N-(S)-1-Isobutyl-2-methoxyethyl 4-(3H-2-methylimidazo[4,5-c]pyridylmethyl)benzenesulphonamide and (B) N-(S)-1-Isobutyl-2-methoxyethyl 4-(1 H-2-methylimidazo[4,5-c]pyridylmethyl)benzenesulphonamide

A

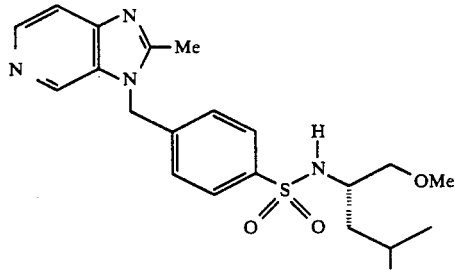

B

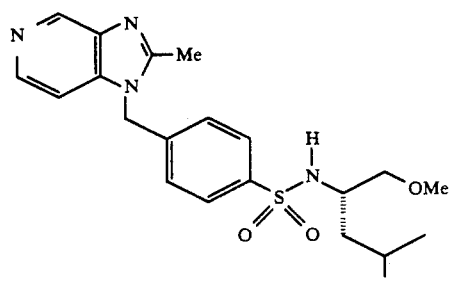

(a) (S)-1-Isobutyl-2-methoxyethylamine

Sodium hydride (60% dispersion in oil: 9.39 g, 0.24 mol) was added to a stirred solution of L-leucinol (25 ml, 0.20 mol) in a mixture of dry acetonitrile (12 ml) and dry THF (60 ml) at room temperature under argon. The mixture was heated at reflux for 2 h, cooled to 55° C. and methyl iodide (12.8 ml, 2.1 mol) carefully added. The reaction mixture was heated at reflux overnight and allowed to cool to room temperature. Ice cold brine (100 ml) was added carefully and the mixture extracted with ethyl acetate (3×100 ml) The combined organic extracts were dried over anhydrous sodium sulphate, filtered and evaporated. The residue was distilled under reduced pressure to give (S)-1-isobutyl-2-methoxyethylamine as a colourless oil which was used directly in the next step.

(b) N-(S)-1-Isobutyl-2-methoxyethyl 4-bromomethylbenzenesulphonamide

N-(S)-1-Isobutyl-2-methoxyethyl 4-bromomethylbenzenesulphonamide was prepared following the procedure of Example 1 Step (b) utilising (S)-1-isobutyl-2-methoxyethylamine in lieu of 2-aminoheptane.

Colourless oil (37% yield over Steps (a) and (b)).

delta $_H$ 7.92–7.83 (2 H, m), 7.58–7.50 (2 H, m), 4.74 (1 H, br d, J 9.4 Hz), 4.62, 4.50 (2 H, 2s), 3.50–3.38 (1 H, m), 3.10 (1 H, dd, J 9.4, 3.0 Hz), 3.17 (3H, s), 3.14 (1 H, dd, J 9.4, 3.8 Hz), 1.60–1.48 (1 H, m), 1.46–1.20 (2 H, m), 0.85 (3H, d, J 7.5 Hz), 0.75 (3H, d, J 7.3 Hz).

(c) (A) N-(S)-1-isobutyl-2-methoxyethyl 4-(3H-2-methylimidazo-[4,5-c]pyridylmethyl) benzenesulphonamide and (B) N-(S)-1-isobutyl-2-methoxyethyl 4-(1 H-2-methylimidazo[4,5-c]pyridylmethyl)benzenesulphonamide A suspension of potassium hydroxide (3.12 g, 56 mmol) and tris(2-(2-methoxyethoxy)ethyl)amine (4 drops) in dry acetonitrile (90 ml) under argon was stirred at room temperature for 10 min. 2-Methylimidazo[4,5-c]pyridine (3.12 g, 23 mmol) was added, the reaction mixture was heated at 80° C. for 40 min. and cooled to 40° C. A solution of N-(S)-1-isobutyl-2-methoxyethyl 4-bromomethylbenzenesulphonamide (8.55 g, 23 mmol) in dry acetonitrile (20 ml) was added and the reaction mixture stirred at 40° C. overnight and cooled to room temperature. Ethanol (100 ml) was added and the resulting slurry filtered through a short pad of celite. Column chromatography (silica: 5% methanol in DCM) gave N-(S)-1-isobutyl-2-methoxyethyl 4-(3H-2-methylimidazo[4,5-c]-pyridylmethyl) benzenesulphonamide (regioisomer A) which eluted first followed by N-(S)-1-isobutyl-2-methoxyethyl 4-(1H-2-methylimidazo [4,5-c]pyridylmethyl)benzenesulphonamide (regioisomer B).

Regioisomer (B): White crystalline solid (2% yield): m.p. 82° C.

Analysis Calculated For C$_{21}$H$_{28}$N$_4$O$_3$S.0.6H$_2$O

Requires C 59.02 H 6.89 N 13.11.
Found C 59.05 H 6.71 N 13.09.
i.r. (KBr) 1320, 1150 cm$^{-1}$.

delta$_H$ 9.04 (1 H, s), 8.37 (1 H, d, i 5.6 Hz), 7.83 (2 H, d, J 8.3 Hz) , 7.20–7.10 (3 H, m) , 5.80 (1 H, br d, J 8.5 Hz) , 5.40 (2 H, s) , 3.43–3.30 (1 H, m), 3.20 (1 H, dd, J 9.5, 3.7 Hz), 3.14 (1 H, dd, i 9.5, 4.3 Hz), 3.14 (3H, s), 2.59 (3H, s), 1.60–1.42 (1 H, m) 1.40–1.20 (2 H, m), 0.79 (3H, d, J 6.6 Hz), 0.69 (3H, d, J 6.4 Hz).

EXAMPLES 20–32

The compounds of Examples 20–32 were prepared by the method of Example 19 starting from the appropriate amino alcohol and alkyl, alkenyl or alkoxyalkyl halide.

20. (A) N-(S)-1-Isobutyl-2-ethoxyethyl 4-(3H-2-methylimidazo-[4,5-c]pyridylmethyl)benzenesulphonamide and (B) 1-N-(S)-1-isobutyl-2-ethoxyethyl 4-(1 H-2-methylimidazo[4,5-c]pyridylmethyl)benzenesulphonamide

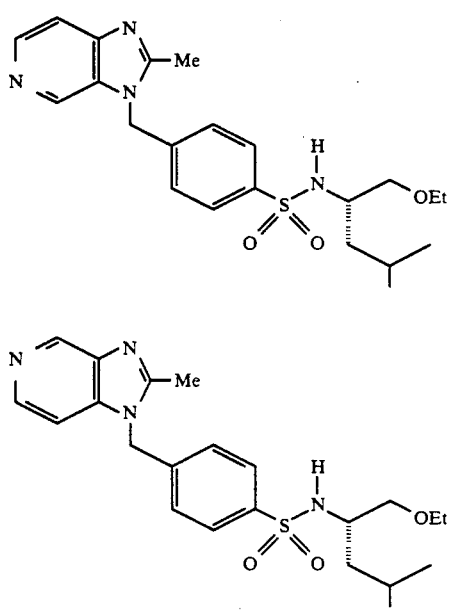

A

B

Regioisomer (A) : White crystalline solid (5% yield for last step after chromatography (silica: 5% methanol in DCM) and crystallisation from ethyl acetate): m.p. 137°–140° C.

i.r. (CDCl₃) 3690, 3380, 2960, 1600, 1335, 1155 cm⁻¹.

delta$_H$ 8.62 (1 H, s), 8.44 (1 H, d, J 5.6 Hz), 7.85 (2 H, d, i 8.4 Hz), 7. 65 (1 H, d, i 5.2 Hz), 7. 19 (2 H, d, J 8.3 Hz), 5. 47 (2 H, s), 4.99 (1 H, d, J 8.5 Hz), 3.42–3.12 (4H, m), 2.62 (3H, s), 1.61–1.20 (4H, m), 1.01 (3H, t, J 7.0 Hz), 0.80 (3H, d, J 6.5 Hz), 0.72 (3H, d, J 6.5 Hz).

delta$_C$ 154.98, 147.94, 142.43, 141.85, 139.51, 132.19, 128.03, 126.74, 114.19, 71.81, 66.57, 52.11, 47.11, 41.77, 24.35, 22.75, 21.94, 14.84, 13.95.

Regioisomer (B): White crystalline solid from ethyl acetate (5% yield): m.p. 162°–165° C.

i.r. (CDCl₃) 3690, 3380, 2960, 1605, 1335, 1155 cm⁻¹.

delta$_H$ 9.03 (1 H, s), 8.36 (1 H, d, J 5.5 Hz), 7.83 (2 H, d, J 8.4 Hz), 7.15–7.11 (3H, m), 5.47 (2 H, s), 5.18 (1 H, d, J 8.5 Hz), 3.42–3.12 (4H, m), 2.62 (3H, s), 1.61–1.20 (4H, m), 1.01 (3H, t, i 7.0 Hz), 0.80 (3H, d, J 6.5 Hz), 0.72 (3H, d, J 6.5 Hz).

delta$_C$ 153.28, 142.11, 142.05, 141.80, 140.17, 139.85, 139.48, 127.96, 126.67, 104.61, 71.90, 66.55, 52.10, 46.86, 41.72, 24.34, 22.78, 21.94, 14.86, 13.92.

21. (A) N-(S)-1-Isobutyl-2-allyloxyethyl 4-(3H-2-methylimidazo-(4,5-c]pyridylmethyl)benzenesulphonamide and (B) 1-N-(S)-1-isobutyl-2-allyloxyethyl 4-(1 H-2-methylimidazo[4,5-c]pyridylmethyl)benzenesulphonamide

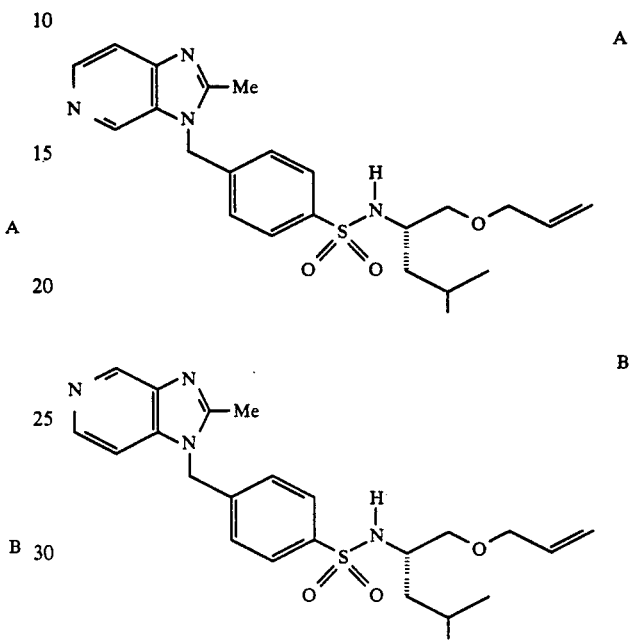

Regioisomer (A) White crystalline solid (3% yield for last step after chromatography (silica: 5% methanol in DCM)): m.p. 132° C.

Analysis Calculated for C₂₃H₃₀N₄O₃S

Requires C 62.41 H 6.84 N 12.67.
Found C 62.25 H 6.83 N 12.30.
i.r. (CHCl₃) 1330, 1145 cm⁻¹.

delta$_H$ 8.55 (1 H, s), 8.29 (1 H, d, J 5.5 Hz), 7.66 (2 H, d, J 8.2 Hz), 7.51 (1 H, d, J 5.6 Hz), 7.04 (2 H, d, J 8.0 Hz), 6.51 (1 H, br s), 5.66–5.48 (1 H, m), 5.36 (2 H, s), 5.06–4.88 (2 H, m), 3.72–3.52 (2 H, m), 3.40–3.26 (1 H, m), 3.20–3.03 (2 H, m), 2.50 (3H, s), 1.53–1.37 (1 H, m), 1.35–1.10 (2 H, m), 0.64 (3H, d, J 6.5 Hz), 0.58 (3H, d, J 6.4 Hz)

Regioisomer (B): White Crystalline solid (3% yield): m.p. 172° C.

Analysis Calculated for C₂₃H₃₀N₄O₃S

Requires C 62.41 H 6.84 N 12.67.
Found C 62.25 H 6.85 N 12.56.
i.r. (CHCl₃) 1335, 1155 cm⁻¹.

delta$_H$ 8.94 (1 H, s), 8.28 (1 H, d, J 5.5 Hz), 7.73 (2 H, d, J 8.2 Hz) 7.14–7.00 (3H, m), 6.12 (1 H, br s), 5.71–5.52 (1 H, m), 5.33 (2 H, s), 5.10–4.93 (2 H, m), 3.73–3.62 (2 H, m), 3.35 (1 H, br s), 3.28–3.10 (2 H, m), 2.51 (3H, s), 1.56–1.38 (1 H, m), 1.37–1.14 (2 H, m), 0.69 (3H, d, i 6.4 Hz), 0.61 (3H, d, J 6.4 Hz).

22. (A) N-(S)-1-Isobutyl-2-n-butoxyethyl 4-(3H-2-methylimidazo-(4,5-c]pyridylmethyl) benzenesulphonamide and (B) 1-N-(S)-1-isobutyl-2-n-butoxyethyl 4-(1H-2-methylimidazo[4,5-c]pyridylmethyl)benzenesulphonamide

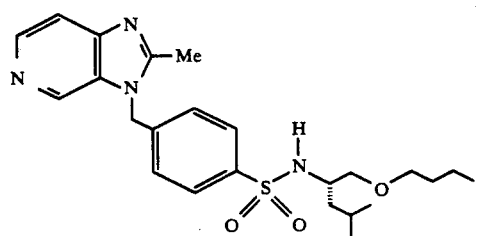

A

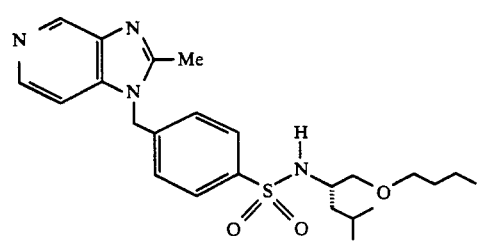

B

Regioisomer (A) : White crystalline solid (6% yield for last step after chromatography (silica: 8% methanol in DCM)): m.p. 92° C.

Analysis Calculated for $C_{24}H_{34}N_4O_3S$

Requires C 62.36 H 7.50 N 12.12 S 6.94.

Found C 62.32 H 7.42 N 11.99 S 7.04.

i.r. (CDCl$_3$) 2210, 1605, 1400, 1330, 1150 cm$^{-1}$.

delta$_H$ 8.61 (1 H, s), 8.42 (1 H, d, J 5.5 Hz), 7.81 (2 H, d, i 8.4 Hz), 7.62 (1 H, d, J 5.5 Hz), 7.16 (2 H, d, J 8.2 Hz), 5.45 (2 H, s), 5.33 (1 H, d, J 8.0 Hz), 3.44–3.28 (1 H, m,), 3.27–3.04 (4H, m), 2.59 (3H, s), 1.60–1.12 (7H, m), 0.82 (3H, t, J 8.0 Hz), 0.77 (3H, d, J 6.5 Hz), 0.69 (3H, d, J 6.4 Hz).

Regioisomer (B): White crystalline solid (5% yield): m.p. 155° C.

Analysis Calculated for $C_{24}H_{34}N_4O_3S$

Requires C 62.36 H 7.50 N 12.12 S 6.94.

Found C 62.60 H 7.41 N 12.13 S 7.10.

(CDCl$_3$) 2210, 1610, 1330, 1150 cm$^{-1}$.

delta$_H$ 9.02 (1 H, s), 8.86 (1 H, d, J 5.5 Hz), 7.83 (2 H, d, J 8.3 Hz), 7.19 (3H, m), 5.39 (2 H, s), 5.18 (1 H, d, J 8.5), 3.44–3.03 (5H, m), 2.58 (3H, s), 1.60–1.12 (7H, m), 0.84 (3H, t, J 7.2 Hz), 0.78 (3H, d, J 6.5 Hz), 0.70 (3H, d, J 6.4 Hz).

23. (A) N-(S)-1-isobutyl-2-n-pentoxyethyl 4-(3H-2-methylimidazo-[4,5-c]pridylmethyl) benzenesulphonamide and (B) N-(S)-1-isobutyl-2-n-pentoxyethyl 4-(1H-2-methylimidazo[4,5-c]pyridylmethyl)benzenesulphonamide

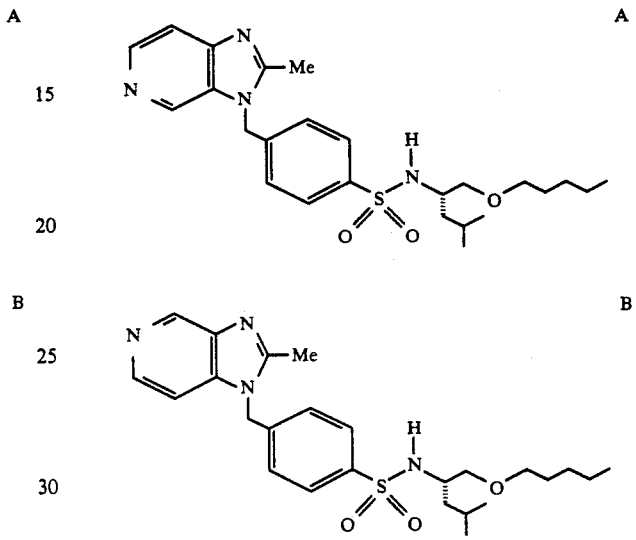

Regioisomer (A) : White crystalline Solid (4% yield for last step after chromatography (silica: 6% methanol in DCM) and crystallisation from ethyl acetate) m.p. 143° C.

Analysis Calculated for $C_{25}H_{36}N_4O_3S \cdot 0.2H_2O$

Requires C 63.05 H 7.70 N 11.76.

Found C 62.96 H 7.58 N 11.58.

i.r. (KBr) 2395, 1510, 1420, 1285, 920 cm$^{-1}$.

delta$_H$ 8.61 (1 H, s), 8.41 (1 H, d, J 5.5 Hz), 7.81 (2 H, d, J 8.3 Hz), 7.62 (1 H, d, J 5.1 Hz), 7.15 (2 H, d, J 8.4 Hz), 5.44 (2 H, s), 5.34 (1 H, d, J 8.5 Hz), 3.35 (1 H, m), 3.16–3.08 (4H, m), 2.59 (3H, s), 1.58–1.10 (9 H, m), 0.91–0.62 (9 H, m).

Regioisomer (B): White crystalline solid from ethyl acetate (4% yield): m.p. 115° C.

Analysis Calculated for $C_{25}H_{36}N_4O_3S$

Requires C 63.53 H 7.68 N 11.86.

Found C 63.22 H 7.61 N 12.01.

i.r. (KBr) 2395, 1420, 1185 cm$^{-1}$.

delta$_H$ 9.02 (1 H, s), 8.36 (1 H, d, i 5.4 Hz), 7.83 (2 H, d, J 8.3 Hz), 7.14 (3H, m), 5.39 (2 H, s), 5.15 (1 H, d, J 8.6 Hz) 3.25 (1 H, m), 3.19 (4H, m), 2.58 (3H, s), 1.55–1.13 (9H, m), 0.86 (3H, t, J 6.7 Hz), 0.78 (3H, d, J 6.5 Hz), 0.71 (3H, d, J 6.5 Hz).

24. (A) N-(S)-1-Isobutyl-2-ethoxymethoxyethyl 4-(3H-2-methylimidazo[4,5-c]pyridylmethyl) benzenesulphonamide and (B) N-(S)-1-isobutyl-2-ethoxymethoxyethyl 4-(1 H-2-methylimidazo[4,5-c]pyridylmethyl)benzenesulphonamide

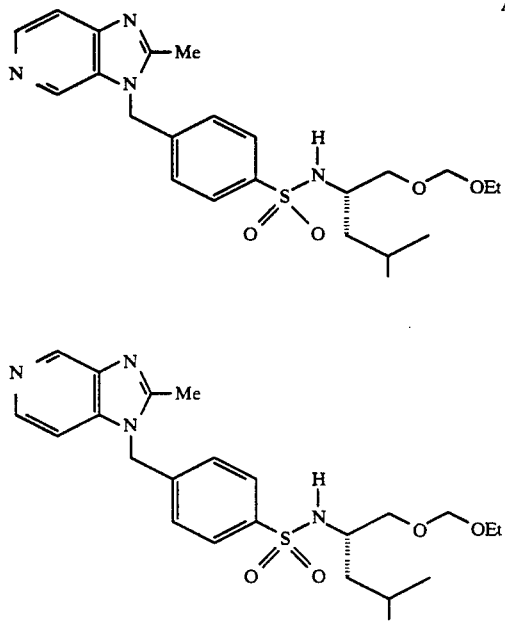

Regioisomer (A) : White solid (23% yield for last step after chromatography (silica: 5% methanol in DCM)):

delta$_H$ 8.62 (1 H, s), 8.44 (1 H, d, i 5.6 Hz), 7.83 (2 H, d, J 8.3 Hz), 7.64 (1 H, d, J 5.0 Hz), 7.17 (2 H, d, J 8.5 Hz), 5.46 (2 H, s), 5.20 (1 H, d, J 8.4 Hz), 4.49 (1 H, d, J 6.6 Hz), 4.45 (1 H, d, J 6.6 Hz), 3.48 (2 H, q, J 7.2 Hz), 3.49–3.37 (3H, m), 2.61 (3H, s), 1.60–1.46 (1 H, m), 1.37–1.22 (2 H, m), 1.15 (3H, t, J 7.2 Hz), 0.79 (3H, d, J 6.5 Hz), 0.70 (3H, d, J 6.5 Hz).

Regioisomer (B): White solid (23% yield):

Analysis Calculated for C$_{23}$H$_{32}$N$_4$O$_4$S

Requires C 59.97 H 7.01 N 12.17.

Found C 59.88 H 7.01 N 12.08.

delta$_H$ 9-00 (1 H, s), 8.34 (1 H, d, J 5.6 Hz), 7.79 (2 H, d, J 8.3 Hz), 7.14–7.03 (3H, m), 5.59 (1 H, d, J 8.4 Hz), 5.37 (2 H, s), 4.46 (1 H, d, i 6.8 Hz), 4.41 (1 H, d, J 6.7 Hz), 3.45 (2 H, q, J 7.1 Hz), 3.48–3.23 (3H, m), 2.56 (3H, s), 1.59–1.44 (1 H, m), 1.36–1.20 (2 H, m), 1.12 (3H, t, J 7.2 Hz), 0.76 (3H, d, J 6.6 Hz), 0.67 (3H, d, J 6.5 Hz).

25. (A) N-(S)-1-Isobutyl-2-(2-methoxyethoxy)ethyl 4-(3H-2-methylimidazo (4,5-c]pyridylmethyl) benzenesulphonamide and (B) N-(S)-1-isobutyl-2-(2-methoxyethoxy)ethyl 4-(1 H-2-methylimidazo[4,5-c]pyridylmethyl)benzenesulphonamide

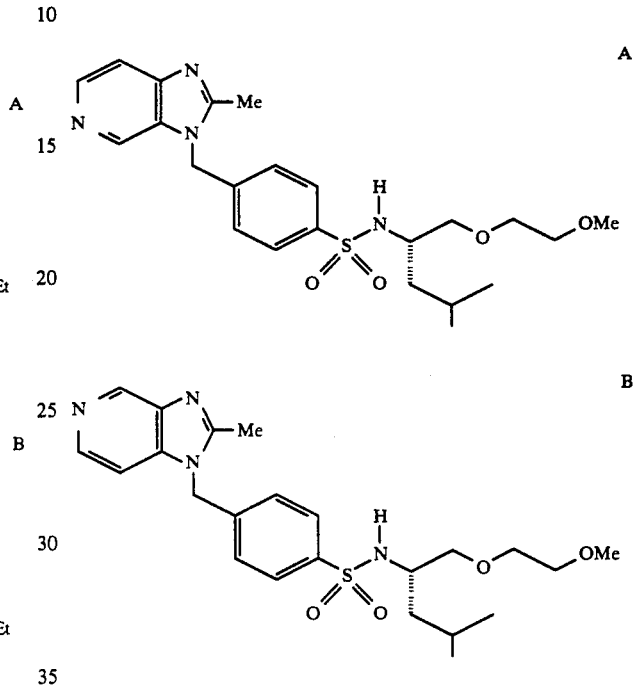

Regioisomer (A) White crystalline solid (4% yield for last step after chromatography (silica: 5% methanol in DCM)): m.p. 103° C.

Analysis Calculated for C$_{23}$H$_{32}$N$_4$O$_4$S

Requires C 59.97 H 7.01 N 12.17.

Found C 60.06 H 7.03 N 12.03.

i.r. (KBr) 1325, 1150 cm$^{-1}$.

delta$_H$ 8.63 (1 H, s), 8.46 (1 H, d, i 5.6 Hz), 7.87 (2 H, d, J 8.3 Hz) , 7. 66 (1 H, d, J 5. 6 Hz) , 7.20 (2 H, d, J 8.3 Hz) , 5. 48 (2 H, s) , 5.26 (1 H, d, J 8.0 Hz), 3.55–3.30 (7H, m), 3.34 (3H, s), 2.63 (3H, s), 1.61–1.45 (2 H, m), 1.35–1.20 (1 H, m), 0.81 (3H, d, J 6.6 Hz), 0.73 (3H, d, J 6.4 Hz)

Regioisomer (B) : white crystalline solid from ethyl acetate (3% yield) : m.p. 140° C.

Analysis Calculated for C$_{23}$H$_{32}$N$_4$O$_4$S

Requires C 59.97 H 7.01 N 12.17.

Found C 59.83 H 7.00 N 11.98.

i.r. (KBr) 1360, 1150 cm$^{-1}$.

delta$_H$ 9.06 (1 H, s), 8.39 (1 H, d, J 5.6 Hz), 7.87 (2 H, d, J 8.3 Hz), 7.20–7.10 (3H, m), 5.41 (2 H, s), 5.25 (1 H, d, J 8.0 Hz), 3.55–3.30 (7H, m), 3.42 (3H, s), 2.61 (3H, s), 1.60–1.20 (3H, m), 0.80 (3H, d, J 6.5 Hz), 0.72 (3H, d, J 6.4 Hz).

26. (A) N-(S)-1-Isobutyl-2-decyloxyethyl 4-(3H-2-methylimidazo-(4,5-c]pyridylmethyl) benzenesulphonamide and (B) N-(S)-1-isobutyl-2-decyloxyethyl 4-(1 H-2-methylimidazo[4,5-c]pyridylmethyl)benzenesulphonamide

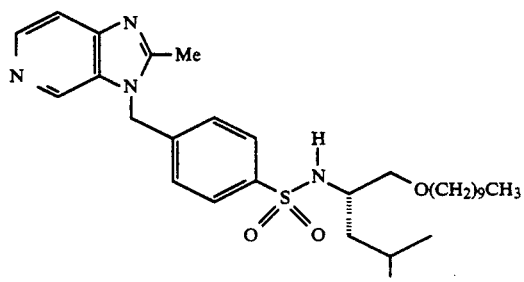
A

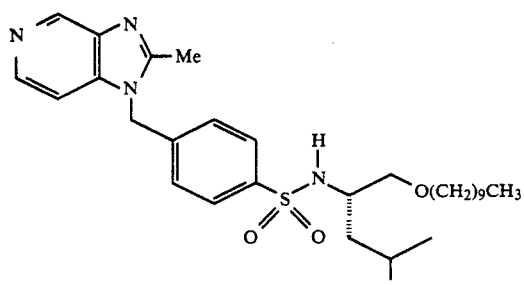
B

Regioisomers (A) and (B) were separated by chromatography (silica:5% methanol in DCM):

Regioisomer (B): Colourless oil (2% yield for last step):

delta$_H$ 8.89 (1 H, br s), 8.46 (1 H, br s), 7.85 (2 H, d, J 8.3 Hz), 7.77-7.72 (1 H, m), 7.18 (2 H, d, J 8.3 Hz), 5.53 (2 H, s), 5.02 (1 H, d, J 8.5 Hz), 3.47-3.32 (2 H, m), 3.31-3.12 (6H, m), 2.66 (3H, s), 1.55-1.14 (16 H, m), 0.88 (3H, t, i 7.0 Hz), 0.80 (3H, d, J 6.5 Hz) , 0. 72 (3H, d, J 6. 4 Hz)

27. (A) N-(R)-1-Isobutyl-2-ethoxyethyl 4-(3H-2-methylimidazo-[4,5-c]pyridylmethyl) benzenesulphonamide and (B) N-(R)-1-isobutyl-2-ethoxyethyl 4-(1 H-2-methylimidazo(4,5-c]pyridylmethyl)benzenesulphonamide

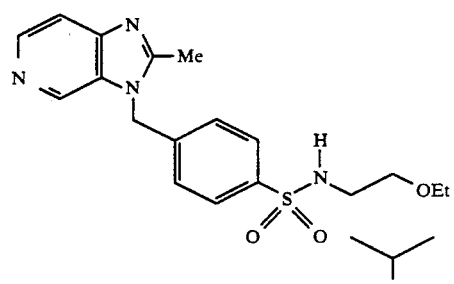
A

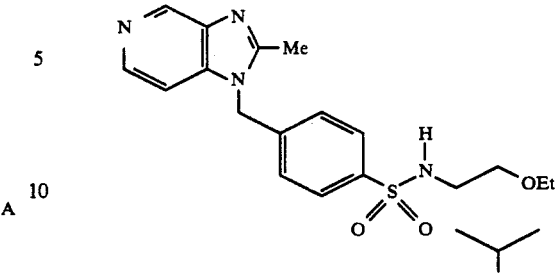
B

Regioisomer (A): White crystalline solid (10% yield for last step after chromatography (silica: 5% methanol in DCM)): m.p. 143°-145° C.

Analysis Calculated for $C_{22}H_{30}N_4O_3S$

Requires C 61.37 H 7.02 N 13.01.

Found C 61.06 H 7.00 N 12.73.

i.r. (CDCl$_3$) 3680, 3380, 2960, 1600, 1400, 1155 cm$^{-1}$.

delta$_H$ 8.62 (1 H, s), 8.44 (1 H, d, J 5.6 Hz), 7.85 (2 H, d, J 8.4 Hz), 7.65 (1 H, d, J 5.2 Hz), 7.19 (2 H, d, J 8.3 Hz), 5.47 (2 H, s), 4.99 (1 H, d, J 8.5 Hz), 3.42-3.12 (4H, m), 2.62 (3H, S), 1.61-1.20 (4H, m), 1.01 (3H, t, i 7.0 Hz), 0.80 (3H, d, i 6.5 Hz), 0.72 (3H, d, J 6.5 Hz).

Regioisomer (B) : White crystalline solid (18% yield) m.p. 175°-177° C.

Analysis Calculated for $C_{22}H_{30}N_4O_3S.0.2H_2O$

Requires C 60.86 H 7.06 N 12.90.

Found C 60.77 H 7.00 N 12.72.

i.r. (CDCl$_3$) 3690, 3380, 2960, 1610, 1330, 1155 cm$^{-1}$.

delta$_H$ 9.03 (1 H, s), 8.36 (1 H, d, J 5.5 Hz), 7.83 (2 H, d, J 8.4 Hz), 7.15-7.11 (3H, m), 5.47 (2 H, s), 5.18 (1 H, d, J 8.5 Hz), 3.42-3.12 (4H, m), 2.62 (3H, s), 1.61-1.20 (4H, m), 1.01 (3H, t, J 7.0 Hz), 0.80 (3H, d, J 6.5 Hz), 0.72 (3H, d, J 6.5 Hz).

28. (A) N-(R)-1-Isobutyl-2-allyloxyethyl 4-(3H-2-methylimidazo-(4,5-c]pyridylmethyl) benzenesulphonamide and (B) N-(R)-1-isobutyl-2-allyloxyethyl 4-(1 H-2-methylimidazo(4,5-c]pyridylmethyl)benzenesulphonamide

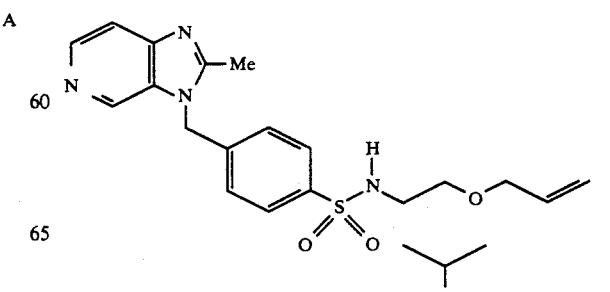
A

-continued

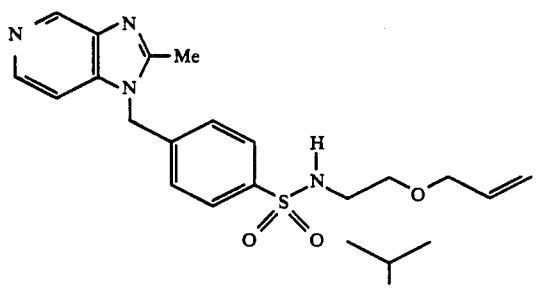

B

Regioisomer (A) White crystalline solid (3% yield for last step after chromatography (silica: 5% methanol in DCM)): m.p. 129° C.

Analysis Calculated for C₂₃H₃₀N₄O₃S

Requires C 62.42 H 6.83 N 12.66 S 7.24.
Found C 62.53 H 6.76 N 12.65 S 7.12.
i.r. (CHCl₃) 2210, 1600 cm⁻¹.
delta$_H$ 8.61 (1 H, s), 8.40 (1 H, d, J 5.6 Hz), 7.79 (2 H, d, J 8.4 Hz), 7.61 (1 H, d, J 5.8 Hz), 7.14 (2 H, d, J 8.4 Hz), 5.74–5.58 (2 H, m), 5.43 (2 H, s), 5.10–5.00 (2 H, m), 3.81–3.70 (2 H, m), 3.41–3.32 (1 H, m), 3.26–3.12 (2 H, m), 2.59 (3H, s), 1.55–1.30 (3H, m), 0.75 (3H, d, i 6.5 Hz), 0.67 (3H, d, J 6.4 Hz)

Regioisomer (B): White crystalline solid (5% yield): m.p. 171° C.

Analysis Calculated for C₂₃H₃₀N₄O₃S.1.2H₂O

Requires C 59.51 H 7.04 N 12.07 S 6.91.
Found C 59.52 H 6.69 N 12.05 S 6.88.
i.r. (CHCl₃) 2210, 1610, 1330 cm⁻¹.
delta$_H$ 9.03, (1 H, s), 8.37 (1 H, d, J 5.6 Hz), 7.83 (2 H, d, J 8.4 Hz), 7.14 (3H, d, J 8.3 Hz), 5.79–5.63 (1 H, m), 5.40 (2 H, s), 5.20–5.05 (3H, m), 3.76 (2 H, d, J 5.6 Hz), 3.46–3.33 (1 H, m), 3.30–3.17 (2 H, m), 2.59 (3H, s) 1.56–1.21 (3H, m), 0.79 (3H, d, J 6.5 Hz), 0.70 (3H, d, J 6.5 Hz)

29. (A) N-1-n-Propyl-2-ethoxyethyl 4-(3H-2-methylimidazo[4,5-c]-pyridylmethyl) benzenesulphonamide and (B) N-1-n-Propyl-2-ethoxyethyl 4-(1 H-2-methylimidazo(4,5-c]pyridylmethyl)benzenesulphonamide

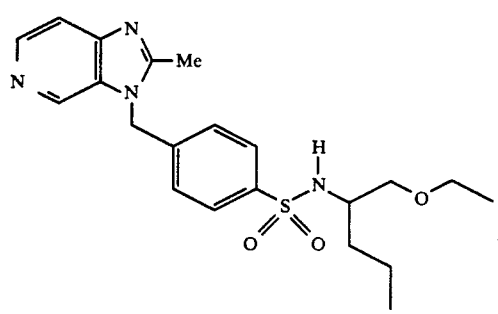

A

-continued

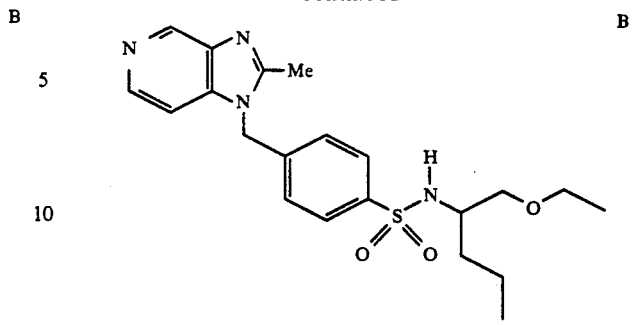

B

Regioisomer (A) White crystalline solid (5% yield for last step after chromatography (silica: 5% methanol in DCM)):

Analysis Calculated for C₂₁H₂₈N₄O₃S.0.3H₂O

Requires C 59.78 H 6.83 N 13.28.
Found C 59.89 H 6.80 N 13.21.
i.r. (CDCl₃) 1330, 1155 cm⁻¹.
delta$_H$ 8.61 (1 H, s), 8.40 (1 H, d, J 5.8 Hz), 7.79 (2 H, d, i 8.3 Hz), 7.61 (1 H, d, J 5.9 Hz), 7.14 (2 H, d, J 8.4 Hz), 5.55 (1 H, m), 5.44 (2 H, s), 3.34–3.10 (5H, m), 2.59 (3H, s), 1.50–1.36 (2 H, m), 1.30–1.08 (2 H, m), 0.98 (3H, t, J 7.0 Hz), 0.74 (3H, t, 3 7.2 Hz).

Regioisomer (B): White crystalline solid (5% yield): m.p. 170° C. (dec.)

Analysis Calculated for C₂₁H₂₈N₄O₃S.0.3H₂O

Requires C 59.78 H 6.83 N 13.28.
Found C 59.86 H 6.76 N 13.28.
i.r. (CDCl₃) 1330, 1155 cm⁻¹.
delta$_H$ 8-95 (1 H, s), 8.29 (1 H, d, J 6.0 Hz), 7.74 (2 H, d, J 8.3 Hz), 7.13–7.03 (3H, m), 5.94 (1 H, d, J 8.0 Hz), 5.35 (2 H, s,), 3.34–3.08 (5H, m), 2.53 (3H, s), 1.49–1.36 (2 H, m), 1.27–1.01 (2 H, m), 0.94 (3H, t, J 6.9 Hz), 0.70 (3H, t, J 7.2 Hz).

30. (A) N-(S)-1-sec-Butyl-2-ethoxyethyl 4-(3H-2-methylimidazo-(4,5-c]pyridylmethyl) benzenesulphonamide and (B) N-(S)-1-sec-butyl-2-ethoxyethyl 4-(1 H-2-methylimidazo[4,5-c]pyridylmethyl)benzenesulphonamide

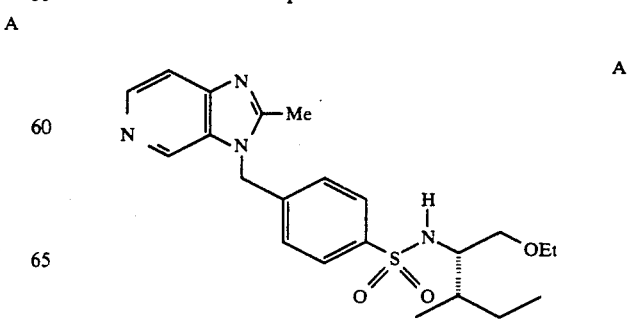

A

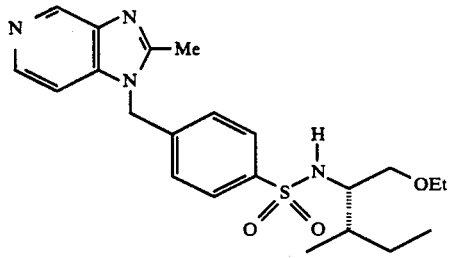

B

Regioisomer (A) : White crystalline solid (5% yield for last step after chromatography (silica: 5% methanol in DCM)): m.p. 142° C.

Analysis Calculated for C$_{22}$H$_{30}$N$_4$O$_3$S

Requires C 61.37 H 7.02 N 13.01.
Found C 61.11 H 6.94 N 12.66.
i.r. (KBr) 1330, 1155 cm$^{-1}$.
delta$_H$ 8.59 (1 H, s), 8.38 (1 H, d, i 5.5 Hz), 7.76 (2 H, d, J 8.3 Hz), 7.59 (1 H, d, J 6.1 Hz), 7.12 (2 H, d, J 8.2 Hz), 5.62–5.50 (1 H, m), 5.42 (2 H, s), 3.30–3.00 (5H, m), 2.58 (3H, s),,1.70–1.50k, (1 H, m) , 1. 45–1.32 (1 H, m) , 1.10–0. 95 (1 H, m) , 0. 90 (3H, t J 7. 0 Hz) , 0.80–0.68 (6 H, m)

Regioisomer (B) : White crystalline solid from ethyl acetate (5% yield) : m.p. 148° C.

Analysis Calculated for C$_{22}$H$_{30}$N$_4$O$_3$S

Requires C 61.37 H 7.02 N 13.01.
Found C 61.24 H 7.03 N 12.90.
i.r. (KBr) 1315, 1150 cm$^{-1}$.
delta$_H$ 9–00 (1 H, s), 8.34 (1 H, d, J 5.5 Hz), 7.80 (2 H, d, J 8.3 Hz), 7.15–7.05 (3H, m), 5.39 (2 H, s), 5.38–5.30 (1 H, m), 3.32–3.05 (5H, m), 2.57 (3H, s), 1.70–1.55 (1 H, m), 1.49–1.38 (1 H, m), 1.06–0.95 (1 H, m), 0.95 (3H, t, J 7.0 Hz), 0.80–0.74 (6H, m).

31. (A) N-(S)-1-Benzyl-2-ethoxyethyl 4-(3H-2-methylimidazo[4,5-c]pyridylmethyl) benzenesulphonamide and (B) N-(S)-1-benzyl-2-ethoxyethyl 4-(1 H-2-methylimidazo[4,5-c]pyridylmethyl)benzenesulphonamide

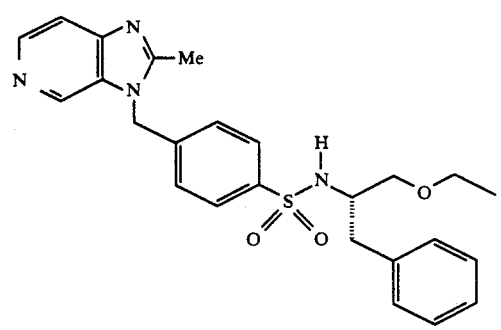

A

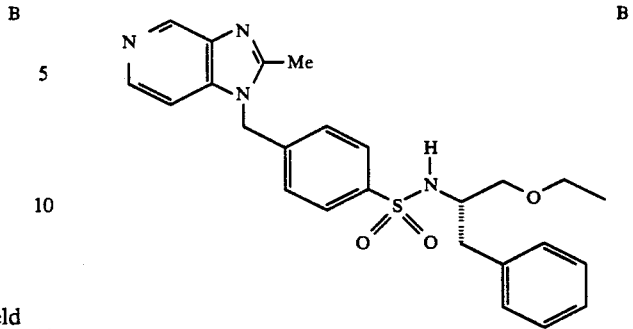

B

Regioisomer (A) White foam (5% yield for last step after chromatography (silica: 5% methanol in DCM)):

Analysis Calculated for C$_{25}$H$_{28}$N$_4$O$_3$S

Requires C 64.63 H 6.07 N 11.92.
Found C 64.58 H 6.13 N 11.87.
i.r. (CDCl$_3$) 3700, 3380, 2980, 2220, 1610, 1400, 1260, 1155 cm$^{-1}$.
delta$_H$ 8.59 (1 H, s), 8.37 (1 H, d, J 5.5 Hz), 7.66–7.59 (3H, m), 7.09–6.95 (7H, m), 6.20 (1 H, d, J 8.0 Hz), 5.36 (2 H, s), 3.58–3.42(1 H, m), 3.29–3.11 (4H, m), 2.84–2.69 (2 H, m), 2.55 (3H, S), 0.98 (3H, t, J 7.0 Hz).

Regioisomer (B): White foam (4% yield):

Analysis Calculated for C$_{25}$H$_{28}$N$_4$O$_3$S.0.5H$_2$O

Requires C 63.40 H 6.17 N 11.83.
Found C 63.37 H 5.97 N 11.81.
i.r. (CDCl$_3$) 3690, 3380, 2980, 2220, 1610, 1520, 1335, 1155 cm$^{-1}$.
delta$_H$ 9–00 (1 H, s), 8.34 (1 H, d, J 5.5 Hz), 7.66 (2 H, d, J 8.3 Hz), 7.15–6.98 (8H, m), 5.76 (1 H, d, i 8.0 Hz), 5.34 (2 H, s), 3.52–3.46 (1 H, m), 3.33–3.14 (4H, m), 2.84–2.71 (2 H, m), 2.55 (3H, s), 1.04 (3H, t, J 6.8 Hz).

32. (A) N-1-Allyl-2-ethoxyethyl 4-(3H-2-methylimidazo[4,5-c]-pyridylmethyl) benzenesulphonamide and (B) N-1-allyl-2-ethoxyethyl 4-(1 H-2-methylimidazo[4,5-c]pyridylmethyl)benzenesulphonamide

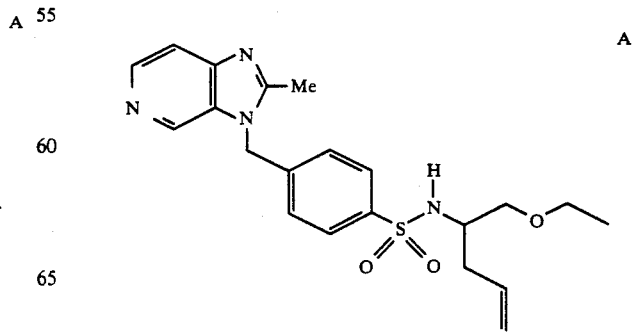

A

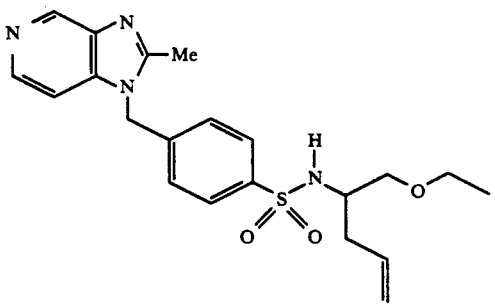

Regioisomer (A) Yellow foam (6% yield for last step after chromatography (silica: 5% methanol in DCM)):
i.r. (CDCl$_3$) 3680, 3380, 2980, 2880, 2220, 1610, 1510, 1400, 1340, 1155 cm$^{-1}$.

delta$_H$ 8.59 (1 H, s), 8.37 (1 H, d, J 5.2 Hz), 7.76 (2 H, d, J 8.2 Hz), 7.59 (1 H, d, J 5.3 Hz), 7.12 (2 H, d, J 8.2 Hz), 5.78 (1 H, br s), 5.53–5.44 (1 H, m), 5.42 (2 H, s), 4.95–4.87 (2 H, M), 3.34–3.12 (5H, m), 2.57 (3H, s), 2.27–2.16 (2 H, m), 0.95 (3H, t, J 7.0 Hz).

delta$_C$ 153.86, 146.47, 140.67, 140.12, 138.14, 132.14, 131.58,, 130.85, 126.46, 125.37, 116.77, 112.66, 69.59, 65.00, 51.78, 45.66, 35.31, 13.46,–12.52.

Regioisomer (B): Yellow foam (3% yield):
i.r. (CDCl$_3$) 3700, 3380, 2980, 2220, 1610, 1340, 1160 cm$^{-1}$.

delta$_H$ 8.99 (1 H, s) , 8.33 (1 H, s) , 7.78 (2 H, d, i 8. 0 Hz) , 7.12–7.08 (3H, m), 5.66 (1 H, br s), 5.63–5.44 (1 H, m), 5.37 (2 H, s), 4.96–4.89 (2 H, m), 3.36–3.15 (5H, m), 2.56 (3H, s), 2.24–2.18 (2 H, m), 0.99 (3H, t, J 6.9 Hz).

delta$_C$ 152.08, 140.58, 140.42, 140.03, 138.81, 138.15, 132.07, 126.53, 125.28, 116.91, 103.35, 69.57, 65.08, 51.77, 45.44, 35.30, 13.49, 12.52.

EXAMPLE 33

1-N-(S)-1-Isobutyl-2-morpholinoethyl 4-(2-methylbenzimidazolylmethyl)benzenesulphonamide

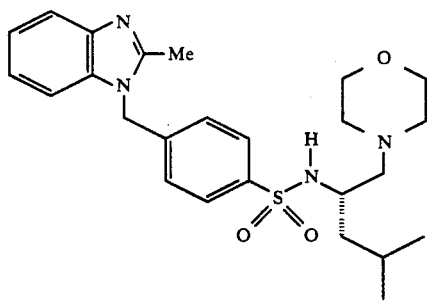

(a) N-tert-Butoxycarbonyl-1-bromo-2-amino-4-methylpentane

A stirred solution of N-tert-butoxycarbonyl-2-amino-pentan-1-ol (2.0 g, 9.2 mmol) in dry DCM (30 ml) at 0° C. was treated with tetrabromomethane (6.1 g, 18.4 mmol) followed by triphenylphosphine (4.84 g, 18.4 mmol). The clear reaction mixture immediately changed to yellow. After 30 min. the solvent was removed under reduced pressure and the residue was purified by column chromatography (flash silica gel; 0–40% ethyl acetate in hexane) to give N-tert-butoxycarbonyl-1-bromo-2-amino-4-methylpentane (1.76 g, 68%) as a colourless oil.

delta$_H$ 4.69 (1 H, br d, J 8.0 Hz), 3.83 (1 H, m), 3.55 (1 H, dd, J 10.2, 3.9 Hz), 3.42 (1 H, dd, J 10.1, 3.3 Hz), 1.61 (1 H, m), 1.48–1.33 (2 H, m), 1.40 (9H, s), 0.89 (6H, d, J 6.8 Hz).

(b) N-tert-Butoxycarbonyl-1-morpholino-2-(S)-amino-4-methylpentane

To a stirred mixture of N-tert-butoxycarbonyl-1-bromo-2-(S)-amino-4-methylpentane 1.76 g, 6.3 mmol) and triethylamine (0.96 ml, 6.9 mmol) in THF (50 ml) at room temperature was added morpholine (0. 60 ml, 6. 9 mmol) .The mixture was stirred overnight and the solvent removed under reduced pressure. The residue was partitioned between saturated aqueous ammonium chloride (50 ml) and ethyl acetate (2×100 ml). The crude N-tert-butoxycarbonyl-1-morpholino -2-(S)-amino-4-methylpentane was then used directly in the next step.

(c) 1-Morpholino-2-(S)-amino-4-methylpentane

Crude N-tert-butoxycarbonyl-1-morpholino-2- (S)-amino-4-methylpentane (6.3 mmol) was dissolved in DCM (50 ml) and treated with excess trifluoroacetic acid (0.48 ml) at 0° C. The mixture was allowed to warm up to room temperature and was stirred for 3 h. The mixture was concentrated to dryness to give 1-morpholino-2-(S)-amino-4-methylpentane trifluoroacetate salt which was used immediately.

(d) 1-N-(S)-1-Isobutyl-2-morpholinoethyl 4-(2-methylbenzimidazolylmethyl)benzenesulphonamide 1-N-(S)-1-isobutyl-2-morpholinoethyl 4-(2-methylbenzimidazolylmethyl) benzenesulphonamide was prepared by the method of Example 1 Strips (b) and (c) starting from crude 1-morpholino-2-(S)-amino-4-methylpentane trifluoroacetate salt and utilising an additional equivalent of triethylamine in the first step to form the sulphonamide.

Pale brown crystalline solid (8% yield for last step after chromatography (silica: 5% methanol in DCM)): m.p. 141° C.

i.r. (KBr) 1320, 1155 cm$^{-1}$.

delta$_H$ 7.90–7.70 (3H, m), 7.30–7.06 (6H, m), 5.40 (2 H, s), 3.52–3.30 (4H, m), 3.25–3.12 (1 H, m), 2.55 (3H, s), 2.35–2.05 (6H, m), 1.70–1.42 (2 H, m) , 1.36–1.20 (1 H, m) , 0.88–0.72 (6H, m)

EXAMPLE 34

(A) N-(S)-1-Isobutyl-2-morpholinoethyl 4-(3H-2-methylimidazo[4,5-c]pyridylmethyl) benzenesulphonamide and (B) N-(S)-1-isobutyl-2-morpholinoethyl 4-(1 H-2-methylimidazo[4,5-c]pyridylmethyl)benzenesulphonamide

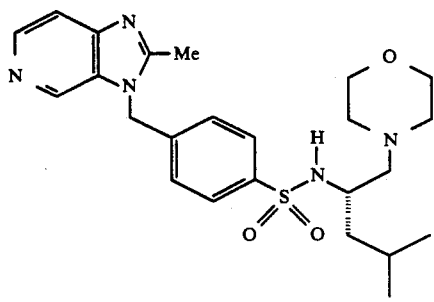

A

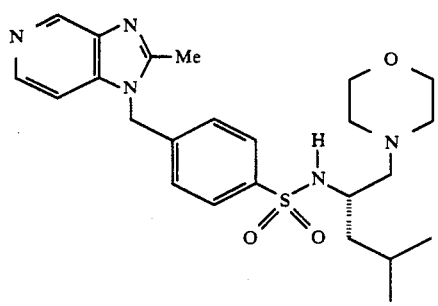

B (A) (A) 1-N-(S)-1-Isobutyl-2-morpholinoethyl 4-(3H-2-methylimidazo[4,5-c]pyridylmethyl) benzenesulphonamide and (B) 1-N-(S)-1-isobutyl-2-morpholinoethyl 4-(1 H-2-methylimidazo[4,5-c]pyridylmethyl)benzenesulphonamide were prepared by the method of Example 33 employing 2-methylimidazo[4,5-c]pyridine in lieu of 2-methylbenzimidazole in the final step.

Regioisomer (A) : Colourless oil (6% yield for last step after chromatography (silica: 5% methanol in DCM)):

$\delta_H$ 8.59 (1 H, br s), 8.45 (1 H, br d, J 5.0 Hz), 7.86 (2 H, d, i 8.3 Hz), 7.65 (1 H, d, J 5.0 Hz), 7.21 (2 H, d, J 8.3 Hz), 5.47 (2 H, s), 3.56–3.39 (4H, m), 3.30–3.15 (1 H, m), 2.63 (3H, s), 2.40–2.08 (6H, m), 2.00 (1 H, br s), 1.65–1.40 (2 H, m), 1.40–1.20 (1 H, m), 0.90–0.70 (6H, m).

Regioisomer (B): Pink crystalline solid (6% yield): m.p. 137° C. (dec.)

$\delta_H$ 9–05 (1 H, s), 8.38 (1 H, d, J 5.5 Hz), 7.85 (2 H, d, J 8.4 Hz), 7.15 (2 H, d, J 8.4 Hz), 7.11 (1 H, d, J 5.5 Hz), 5.40 (2 H, s), 3.55–3.40 (4H, m) , 3.30–3.15 (1 H, m) , 2.59 (3H, S) , 2.35–2.10 (6H, m) , 1.60–1.41 (2 H, m) , 1.35–1. 15 (1 H, M) , 0. 85–0. 70 (6H, m)

$\delta_C$ 154.91, 147.93, 142.53, 140.95, 139.75, 132.15, 129.39, 128.18, 127.27, 126.60, 114.25, 66.63, 61.75, 53.41, 48.95, 47.10, 45.28, 24.44, 22.96, 22.25.

EXAMPLE 35

(A) N-Methyl-N-(S)-1-isobutyl-2-ethoxyethyl 4-(3H-2-methylimidazo-[4,5-c]pyridylmethyl) benzenesulphonamide and (B) N-methyl-N-(S)-1-isobutyl-2-ethoxyethyl 4-(1 H-2-methylimidazo[4,5-c]pyridylmethyl)benzenesulphonamide

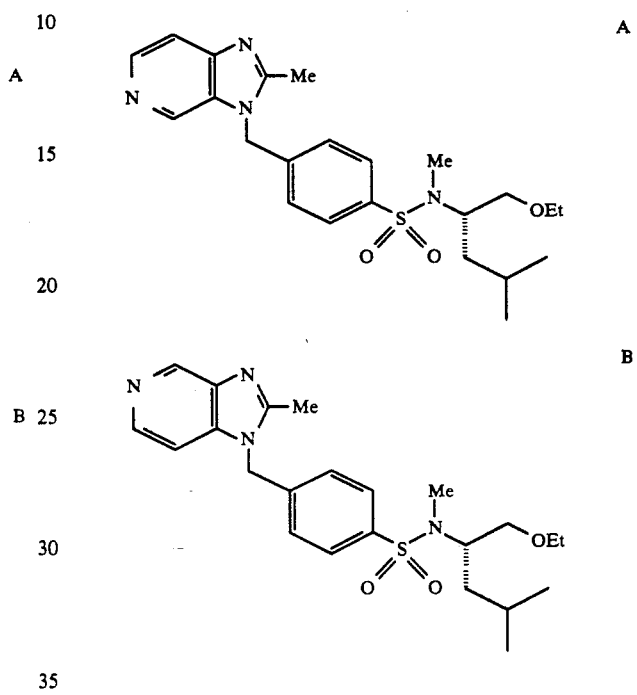

(a) N-Methyl-N-(S)-1-isobutyl-2-ethoxyethyl 4-bromomethylbenzenesulphonamide

Sodium hydride (60% dispersion in oil: 0.31 g, 7.9 mmol) was added to a stirred solution of N-(S)-1-isobutyl-2-ethoxyethyl 4-bromomethylbenzenesulphonamide (2.50 g, 6.6 mmol: prepared from L-leucinol following the procedure of Example 19 Steps (a) and (b) utilising ethyl iodide in lieu of methyl iodide) in dry THF (50 ml) at 0° C under argon. The solution was allowed to warm up to room temperature and was stirred for 1 h. Methyl iodide (0.82 ml, 13.2 mmol) was added dropwise and the mixture stirred overnight. The solvent was evaporated under reduced pressure and the organics extracted with ethyl acetate (100 ml) and washed with water (100 ml) and brine (100 ml). The organics were dried over anhydrous magnesium sulphate, filtered and evaporated to give N-methyl-N-(S)-1-isobutyl-2-ethoxyethyl 4-bromomethylbenzene-sulphonamide as a yellow oil (2.46 g, 95%).

$\delta_H$ 7.84 (2 H, d, J 8.3 Hz), 7.46 (2 H, d, J 8.3 Hz), 5.30 (2 H, s), 4.16 (1 H, m), 3.37–3.20 (4H, m), 2.71 (3H, s), 1.61 (1 H, m), 1.40–1.15 (2 H, m), 0.98 (3H, t, J 7.0 Hz), 0.93 (3H, d, J 6.5 Hz), 0.91 (3H, d, i 6.6 Hz).

(b) (A) N-Methyl-N-(S)-1-isobutyl-2-ethoxyethyl 4-(3H-2-methylimidazo[4,5-c]pyridylmethyl) benzenesulphonamide and (B) N-methyl-N-(S)-1-isobutyl-2-ethoxyethyl 4-(1 H-2-methylimidazo[4,5-c]-pyridylmethyl)benzenesulphonamide (A) N-Methyl-N-(S)-1-isobutyl-2-ethoxyethyl 4-(3H-2-methylimidazo(4,5-c]pyridylmethyl) benzenesulphonamide and (B) N-methyl-N-(S)-1-isobutyl-2-ethoxyethyl 4-(1 H-2-methylimidazo[4,5-c]-pyridylmethyl)-benzenesulphonamide were prepared by the procedure of Example 19 Step (c) employing N-methyl-N-(S)-1-isobutyl-2-ethoxyethyl 4-bromomethylbenzenesulphonamide in lieu of N-(S)-1-isobutyl-2-methoxyethyl 4-bromomethylbenzenesulphonamide.

Regioisomer (A): Orange oil (0.4 g, 2%).

i.r. (CDCl$_3$) 1330, 1150 cm$^{-1}$.

delta$_H$ 8.63 (1 H, s), 8.44 (1 H, d, J 5.5 Hz), 7.83 (2 H, d, J 8.3 Hz), 7.65 (1 H, d, J 5.5 Hz), 7.15 (2 H, d, J 8.3 Hz), 5.46 (2 H, s), 4.25–4.10 (1 H, m), 3.35–3.10 (4H, m), 2.69 (3H, s), 2.63 (3H, s), 1.70–1.50 (1 H, m), 1.40–1.10 (2 H, m), 0.97–0.83 (9H. m).

delta$_C$ 155.13, 147.99, 142.26, 140.73, 139.01, 133.02, 132.17, 128.55, 126.39, 114.19, 70.86, 66.23, 54.99, 47.13, 38.02, 28.34, 24.37, 23.21, 21.97, 14.83.

Regioisomer (B): Off white crystalline solid from DIPE/ethyl acetate (0.4 g, 2%): m.p. 99°–101° C.

i.r. (CDCl$_3$) 2960, 1330, 1150 cm$^{-1}$.

$[\alpha]_D^{20}$ −7.8 (c 1.9, CHCl$_3$).

delta$_H$ 9.00 (1 H, s), 8.33 (1 H, d, J 5.5 Hz), 7.77 (2 H, d, J 8.4 Hz), 7.15–7.05 (3 H, m), 5.36 (2 H, s), 4.20–4.05 (1 H, m), 3.30–3.10 (4 H, M), 2.66 (3 H, S), 2.57 (3 H, s), 1.60–1.45 (1 H, m), 1.36–1.07 (2 H, M), 0.90–0.80 (9 H, m).

delta$_C$ 153.22, 142.04, 141.95, 140.51, 140.10, 139.76, 139.05, 128.34, 126.30, 104.60, 70.74, 66.13, 54.89, 46.75, 37.92, 28.28, 24.28, 23.09, 21.90.

An alternative regioselective synthesis gives regioisomer (B) alone in an improved overall yield and involves the following steps.

(c) N-(S)-1-Isobutyl-2-ethoxyethyl 4-azidomethylbenzenesulphonamide

A solution of sodium azide (18.4 g, 0.287 mol) in water (120 ml) was added to a solution of the N-(S)-1-Isobutyl-2-ethoxyethyl 4-bromomethylbenzenesulphonamide (21.7 g, 57 mmol) in dichloromethane (120 ml). Benzyltriethylammonium chloride (2 g, 8.8 mmol) was added and the heterogenous reaction mixture stirred vigorously for 60 h. The organic portion was separated, washed thoroughly with water, dried over anhydrous magnesium sulphate, filtered and concentrated to a golden oil, which crystallised on standing. The resulting white solid was freeze dried overnight to yield N-(S)-1-isobutyl-2-ethoxyethyl 4-azidomethylbenzenesulphonamide (19.1 g, 98%).

delta$_H$ 7.91 (2 H, d, J 8.4 Hz), 7.46 (2 H, d, J 8.6 Hz), 4.86 (1 H, d, J 8.6 Hz), 4.44 (2 H, s), 3.45–3.13 (5H, m), 1.63–1.50 (1 H, m), 1.47–1.22 (2 H, m), 1.08 (3H, t, J 7.1 Hz), 0.84 (3H, d, J 6.6 Hz), 0.77 (3H, d, J 6.5 Hz) .

(d) N-Methyl-N-(S)-1-isobutyl-2-ethoxyethyl 4-azidomethylbenzenesulphonamide A 60% dispersion of sodium hydride in mineral oil (2.3,7 g, 59.3,, mmol) was added in portions to a solution of N-(S)-1-isobutyl-2-ethoxyethyl 4-azidomethylbenzenesulphonamide (19.1 g, 53.9 mmol) in THF (75 ml) at 0° C. After stirring for 20 min. iodomethane (6.7 ml, 0.107 mol) was added slowly, and the reaction allowed to warm to ambient temperature overnight. Saturated ammonium chloride solution (ca. 15 ml) was added and the THF removed under reduced pressure. The resulting residue was taken up in dichloromethane, washed with saturated hydrogen carbonate solution and water, dried over anhydrous magnesium sulphate, filtered and concentrated to give N-methyl-N-(S)-1-isobutyl-2-ethoxyethyl 4-azidomethylbenzenesulphonamide as an orange oil (19.4 g, 98%).

delta$_H$ 7.87 (2 H, d, J 8.4 Hz), 7.42 (2 H, d, J 8.3 Hz), 4.42 (2 H, s), 4.24–4.11 (1 H, m), 3.36–3.18 (4H, m), 2.73 (3H, s), 1.66–1.52 (1 H, m), 1.41–1.15 (2 H, m), 0.99 (3H, t, J 7.0 Hz), 0.93 (3H, d, J 6.5 Hz) , 0. 91 (3 H, d, J 6.6 Hz)

(e) N-Methyl-N-(S)-1-isobutyl-2-ethoxyethyl 4-aminomethylbenzenesulphonamide Triphenylphosphine (30.64 g, 0.116 mol) was added to a solution to N-methyl-N-(S)-1-isobutyl-2-ethoxyethyl 4-azidomethylbenzenesulphonamide (19.4 g, 58.5 mmol) in a mixture of THF and water (4:1, 125 ml), and the reaction mixture stirred overnight at ambient temperature. The THF was removed under reduced pressure, and the product extracted with ethyl acetate, dried over anhydrous magnesium sulphate, filtered and concentrated to an orange oil. This was purified by chromatography over silica (1:2 EtOAchexane; EtOAc; 10% MeOH-EtOAc) to give N-methyl-N-(S)-1-isobutyl-2-ethoxyethyl 4-aminomethylbenzenesulphonamide (12.2 g, 68%) as a yellow oil.

delta$_H$ 7.81 (2 H, d, J 8.3 Hz), 7.43 (2 H, d, J 8.3 Hz), 4.24–4.13 (1 H, m), 3.95 (2 H, s), 3.39–3.19 (4H, m), 2.70 (3H, s), 1.65–1.51 (1 H, m), 1.39–1.15 (2 H, m), 1.00 (3H, t, J 7.0 Hz), 0.92 (3H, d, i 6.4 Hz), 0.89 (3H, d, J 6.9 Hz).

(f) N-Methyl-N-(S)-1-isobutyl-2-ethoxyethyl 4-(N'-3-nitropyrid-4-yl) aminomethylbenzenesulphonamide 4-Chloro-3-nitropyridine (5.46 g, 34.5 mmol) was added to a stirred solution of N-methyl-N-(S)-1-isobutyl-2-ethoxyethyl 4-aminomethylbenzenesulphonamide (12.2 g, 34.5 mmol) and triethylamine (4.8 ml, 34.5 mmol) in chloroform (150 ml) at ambient temperature. The reaction mixture was stirred for 60 h, then washed with water, dried over anhydrous magnesium sulphate, filtered and the solvent removed under reduced pressure to leave an orange oil. This was purified by chromatography over silica (gradient elution 33% EtOAC-hexane ETOAC) to give N-methyl-N-(S)-1-isobutyl-2-ethoxyethyl 4-(N'-3-nitropyrid-4-yl)aminomethylbenzenesulphonamide (10.1 g, 60%) as a yellow amorphous solid.

delta$_H$ 9.25 (1 H, s), 8.62–8.57 (1 H, br m), 8.27 (1 H, d, J 5.9 Hz), 7.87 (2 H, d, J 8.4 Hz), 7.42 (2 H, d, J 8.3 Hz), 6.63 (1 H, d, J 6.2 Hz), 4.65 (2 H, d, J 5.9 Hz), 4.24–4.13 (1 H, m), 3.37–3.16 (4H, m), 2.72 (3H, s), 1.65–1.51 (1 H, m), 1.40–1.13 (2 H, m), 0.95 (3H, t, J 7. 0 Hz) , 0. 91 (3H, d, J 6. 4 Hz) , 0. 90 (3H, d, J 6. 6 Hz).

(g) N-Methyl-N-(S)-1-isobutyl-2-ethoxyethyl 4-(N'-3-aminopyrid-4-yl) aminomethylbenzenesulphonamide A solution of N-methyl-N-(S)-1-isobutyl-2-ethoxyethyl 4-(N'-3-nitropyrid-4-yl) aminomethylbenzenesulphonamide (10.1 g, 22.5 mmol) in ethanol (40 ml) was hydrogenated at 120 p.s.i. overnight in the presence of 10% palladium in charcoal (1.0 g). The catalyst was removed by filtration through GF/F filter paper, and the filtrate evaporated under reduced pressure to give N-methyl-N-(S)-1-isobutyl-2-ethoxyethyl 4-(N'-3-aminopyrid-4-yl)aminomethylbenzenesulphonamide (9.54 g, 90%) as a green oil.

delta$_H$ 7.84–7.80 (2 H, br m), 7.77 (2 H, d, J 8.3 Hz), 7.38 (2 H, d, J 8.2 Hz), 6.29 (1 H, d, J 5.3 Hz), 5.10 (1 H, m), 4.42 (2 H, d, J 5.2 Hz), 4.21–4.10 (1 H, m), 3.32–3.15

(6H, m), 2.70 (3H, s), 1.62–1.51 (1 H, m), 1.49–1.13 (2 H, m), 0.95 (3H, t, J 7.0 Hz), 0.89 (3H, d, J 6. 4 Hz) , 0 . 8 8 (3 H, d, J 6. 6 Hz) .

(h) N-Methyl-N-(S)-1-isobutyl-2-ethoxyethyl 4-(1 H-2-methylimidazo[4,5-c]pyridylmethyl) benzenesulphonamide N-Methyl-N-(S)-1-isobutyl-2-ethoxyethyl 4-(N'-3-aminopyrid-4-yl) aminomethylbenzenesulphonamide (9.54 g, 23 mmol) was refluxed overnight in acetic anhydride (90 ml). The reaction mixture was allowed to cool, then methanol added cautiously until effervescence ceased. The volatiles were removed under reduced pressure and the residue partitioned between saturated sodium hydrogen carbonate solution and ethyl acetate. The organic portion was washed with saturated aqueous sodium hydrogen carbonate, and water, dried over anhydrous sodium sulphate, filtered and concentrated to a brown oil. The residue was filtered through a pad of silica (3% methanol in DCM) to remove baseline material, and the product further purified by medium pressure liquid chromatography (silica: 3% methanol in DCM plus trace of triethylamine) to give a pale yellow oil (5.6 g, 55%), which solidified slowly on standing. Recrystallisation from ethyl acetate/DIPE gave N-methyl-N-(S)-1-isobutyl-2-ethoxyethyl 4-(1 H-2-methylimidazo[4,5-c]pyridylmethyl) benzenesulphonamide as a white crystalline solid identical to that obtained above in step (b).

EXAMPLES 36–40

The compounds of Examples 36–40 were prepared by the method of Example 35 Steps (a) and (b) starting from the appropriate 4-bromomethylbenzenesulphonamide derivative.

36. (A) N-Methyl-N-(S)-1-isobutyl-2-allyloxyethyl 4-(3H-2-methylimidazo[4,5-c]pyridylmethyl) benzenesulphonamide and (B) N-methyl-N-(S)-1-isobutyl-2-allyloxyethyl 4-(1 H-2-methylimidazo[4,5-c]pyridylmethyl)benzenesulphonamide

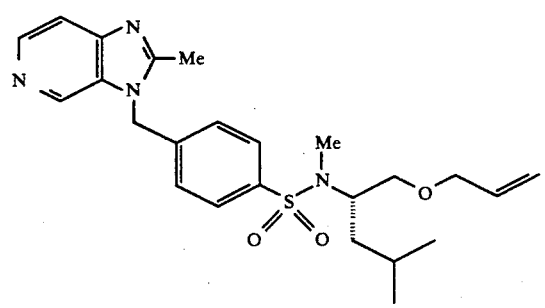

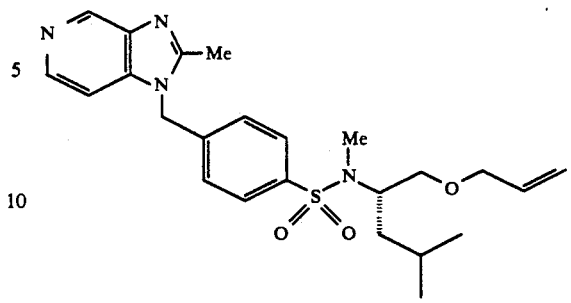

Regioisomer (A) Colourless oil (10% yield for last step after chromatography (silica: 6% methanol in DCM)):

Analysis Calculated for $C_{24}H_{32}N_4O_3S \cdot 0.6H_2O$

Requires C 61.67 H 7.16 N 11.99 S 6.86.
Found C 61.60 H 7.02 N 11.78 S 6.96.
i.r. $(CDCl_3)$ 2210, 1395, 1330, 1150 cm$^{-1}$.
$delta_H$ 8.38, (1 H, s), 8.18 (1 H, d, J 5.5 Hz), 7.52 (2H, d, J 8.3 Hz), 7.38 (1 H, d, J 6.0 Hz), 6.92 (2H, d, J 8.3 Hz), 5.24 (2H, s), 5.42–5.17 (1 H, m), 4.86–4.74 (2H, m), 3.98–3.88 (1 H, m), 3.53–3.37 (2H, m), 3.00 (2H, d, J 6.0 Hz), 2.45 (3H, s), 2.38 (3H, s), 1.41–1.23 (1 H, m), 1.15–0.84 (2H, m), 0.65 (3H, d, J 6.4 Hz), 0.64 (3H, d, J 6.6 Hz).

Regioisomer (B): Colourless oil (12% yield):
i.r. $(CDCl_3)$ 1330, 1130 cm$^{-1}$.
$delta_H$ 8.80 (1 H, s), 8.13 (1 H, d, J 5.6 Hz), 7.53 (2H, d, J 8.3 Hz), 6.98 (1 H, d, J 5.5 Hz), 6.91 (2H, d, J 8.3 Hz), 5.46–5.29 (1 H, m), 5.21 (2H, s), 4.93–4.78 (2H, m), 4.06–3.88 (1 H, m), 3.51 (1 H, dd, J 13.0, 5.4 Hz), 3.43 (1 H, dd, J 12.9, 5.8 Hz), 3.03 (2H, d, J 6.1 Hz), 2.48 (3H, s), 2.38 (3H, s), 1.43–1.28 (1 H, m), 1.20–0.86 (2H, m), 0.68 (3H, d, J 6.4 Hz), 0.67 (3H, d, J 6.6 Hz).
$delta_C$ 153.02, 141.49, 141.24, 139.69, 139.33, 138.98, 133.76, 127.74, 126.03, 116.49, 104.42, 71.15, 69.77, 54.49, 46.29, 37.34, 27.92, 23.85, 22.66, 21.46.

37. (A) N-Methyl-N-(S)-1-isobutyl-2-n-butoxyethyl 4-(3H-2-methylimidazo[4,5-c]pyridylmethyl) benzenesulphonamide and (B) N-methyl-N-(S)-1-isobutyl-2-n-butoxyethyl 4-(1 H-2-methylimidazo[4,5-c]pyridylmethyl)benzenesulphonamide

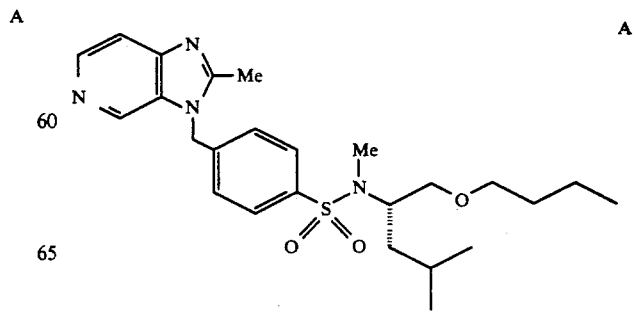

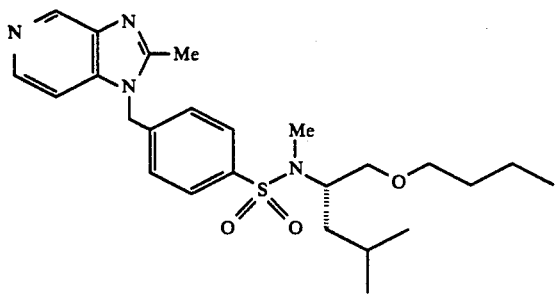

Regioisomer (A): Colourless oil (13% yield for last step after chromatography (silica: 4% methanol in DCM)):

Analysis Calculated for $C_{25}H_{34}N_4O_3S.0.9H_2O$

Requires C 61.42 H 7,79 N 11.46.
Found C 61.54 H 7.49 N 11.34.
i.r. (CDCl$_3$) 1330, 1150 cm$^{-1}$.
delta$_H$ 8.62 (1 H, s), 8.45 (1 H, d, J 5.5 Hz), 7.84 (2H, d, J 8.4 Hz), 7.65 (1 H, d, J 5.7 Hz), 7.15 (2H, d, J 8.3 Hz), 5.46 (2H, s,), 4.23–4.11 (1 H, m), 3.30–3.14 (4H, m), 2.70 (3H, s), 2.62 (3H, S), 1.64–1.45 (1 H, m), 1.40–1.12 (6H, m), 0.90 (3H, d, J 6.4 Hz), 0.88 (3 H, d, J 6.7 Hz), 0.83 (3H, t, J 7.0 Hz)

Regioisomer (B): Colourless oil (16% yield);
i.r. (CDCl$_3$) 1330, 1150 cm$^{-1}$.
delta$_H$ 9.03 (1 H, s), 8.35 (1 H, d, J 5.5 Hz) 7.80 (2H, d, J 8.3 Hz), 7.15–7.06 (3H, m), 5.37 (2H, s), 4.20–4.04 (1 H, m), 3.30–3.07 (4H, m), 2.68 (3H, s), 2.58 (3H, s), 1.62–1.44 (1 H, m), 1.40–1.10 (6H, m), 0.87 (3H, d, J 6.4 Hz), 0.86 (3H, d, J 6.6 Hz), 0.81 (3H, t, J 7.2 Hz).
delta$_C$ 153.10, 141.61, 141.40, 139.99, 139.86, 139.46, 139.04, 127.84, 126.16, 104.48, 70.84, 70.39, 54.89, 46.44, 37.59, 31.01, 28.20, 24.00, 22.75, 21.66, 18.75, 13.58.

38. (A) N-Methyl-N-(S)-1-isobutyl-2-n-pentoxyethyl 4-(3H-2-methylimidazo[4,5-c]pyridylmethyl) benzenesulphonamide and (B) N-methyl-N-(S)-1-isobutyl-2-n-pentoxyethyl 4-(1 H-2-methylimidazo-(4,5-c]pyridylmethyl)benzenesulphonamide

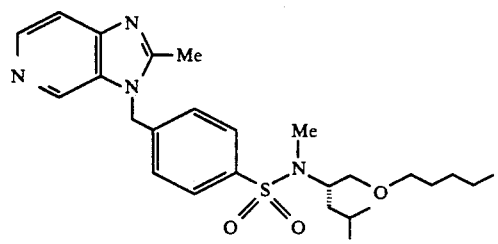

A

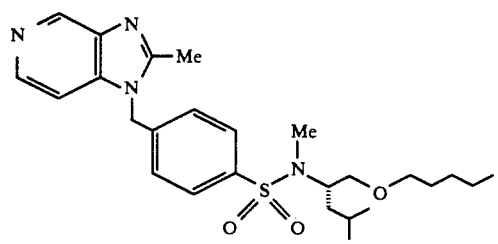

B

Regioisomer (A): Colourless oil (3% yield for last step after chromatography (silica: 6% methanol in DCM)):

Analysis Calculated for $C_{26}H_{38}N_4O_3S.0.4H_2O$

Requires C 63.23 H 7.92 N 11.34.
Found C 63.24 H 7.83 N 11.39.
i.r. (KBr) 2215, 1330, 1150 cm$^{-1}$.
delta$_H$ 8.61 (1 H, s), 8.42 (1 H, d, J 5.5 Hz), 7.80 (2H, d, J 8.4 Hz), 7.63 (1 H, d, J 5.5 Hz), 7.13 (2H, d, J 8.4 Hz), 5.44 (2H, s), 4.20–4.09 (1 H, m), 3.25–3.10 (4H, m), 2.67 (3H, s), 2.60 (3H, s), 1.60–1.45 (1 H, m), 1.40–1.10 (8H, m), 0.90–0.80 (9H, m).

Regioisomer (B): Colourless oil (6% yield).

Analysis Calculated for $C_{26}H_{38}N_4O_3S.1.0H_2O$

Requires C 61.88 H 7.99 N 11.10.
Found C 61.91 H 7.68 N 11.08.
i.r. (KBr) 2395, 1330, 1150 cm$^{-1}$.
delta$_H$ 9.02 (1 H, s), 8.35 (1 H, d, J 5.4 Hz), 7.74 (2H, d, J 8.2 Hz), 7.13–7.06 (3H, m), 5.37 (2H, s), 4.20–4 .07 (1 H, m), 3.28–3.06 (4 H, m), 2.68 (3H, s), 2.58 (3H, s), 1.60–1.43 (1 H, m), 1.40–1.10 (8 H, m), 0.90–0.80 (9H, m).

39. (A) N-Methyl-N-(R)-1-isobutyl-2-allyloxyethyl 4-(3H-2-methylimidazo[4,5-c]pyridylmethyl) benzenesulphonamide and (B) N-methyl-N-(R)-1-isobutyl-2-allyloxyethyl 4-(1 H-2-methylimidazo[4,5-c]pyridylmethyl)benzenesulphonamide

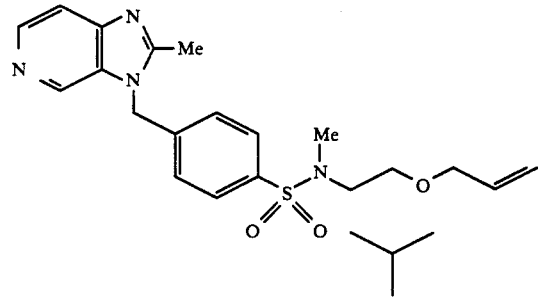

A

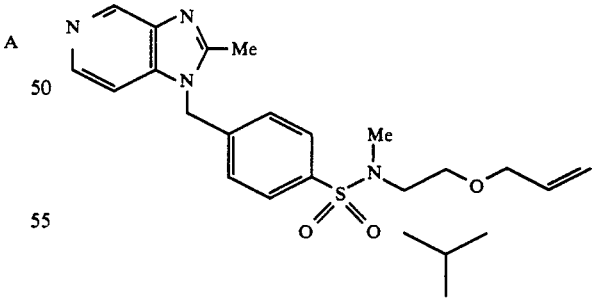

B

Regioisomer (A): Pale yellow crystalline solid (2% yield for last step after chromatography (silica: 6% methanol in DCM) m.p. 115° C.
i.r. (CDCl$_3$) 2205, 1610, 1330 cm$^{-1}$.
delta$_H$ 8.38, (1 H, s), 8.18 (1 H, d, J 5.5 Hz), 7.52 (2H, d, J 8.3 Hz), 7.38 (1 H, d, J 6.0 Hz), 6.92 (2H, d, J.8.3 Hz), 5.24 (2H, s) 5.42–5.17 (1 H, m), 4.86–4.74 (2H, m), 3.98–3.88 (1 H, m), 3.53–3.37 (2H, m), 3.00 (2H, d, J 6.0 Hz), 2.45 (3H, s), 2.38 (3H, s), 1.41–1.23 (1 H, m), 1.15–0.84 (2H, m), 0.65 (3H, d, J 6.4 Hz), 0.64 (3H, d, J 6.6 Hz).

delta$_C$ 154.82, 147.47, 141.89, 139.91, 139.08, 133.90, 132.69, 132.09, 127.96, 126.21, 116.61, 113.63, 71.31, 69.98, 54.62, 46.73, 37.52, 28.08, 24.00, 22.81, 21.59, 13.64.

Regioisomer (B): Yellow oil (2% yield):

Analysis Calculated for $C_{24}H_{32}N_4O_3S.0.9H_2O$

Requires C 61.07 H 7.02 N 11.74.
Found C 60.97 H 7.21 N 11.85.
i.r. (CDCl$_3$) 2210, 1610, 1590, 1330 cm$^{-1}$.

delta$_H$ 8.80 (1 H, s), 8.13 (1 H, d, J 5.6 Hz), 7.53 (2H, d, J 8.3 Hz), 6.98 (1 H, d, J 5.5 Hz), 6.91 (2H, d, J 8.3 Hz), 5.4 6–5.29 (1 H, m), 5.21 (2H, s), 4.93–4.78 (2H, m), 4.06–3.88 (1 H, m), 3.51 (1 H, dd, J 13.0, 5.4 Hz), 3.43 (1 H, dd, J 12.9, 5.8 Hz), 3.03 (2H, d, J6.1 Hz), 2.48 (3H, S), 2.38 (3H, s), 1.43–1.28 (1 H, m), 1.20–0.86 (2H, m), 0.68 (3H, d, J 6.4 Hz), 0.67 (3H, d, J 6.6 Hz).

40. (A) N-Methyl-N-(S)-1-sec-butyl-2-methoxyethyl 4-(3H-2-methyl-imidazo[4,5-c]pyridylmethyl) benzenesulphonamide and (B) N-methyl-N-(S)-1-sec-butyl-2-methoxyethyl 4-(1 H-2-methylimidazo[4,5-c]-pyridylmethyl)benzenesulphonamide

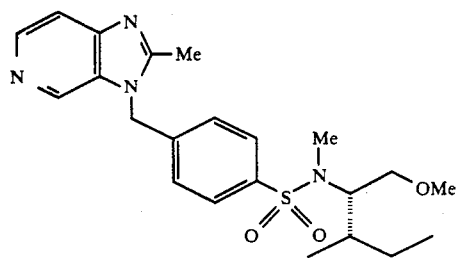

A

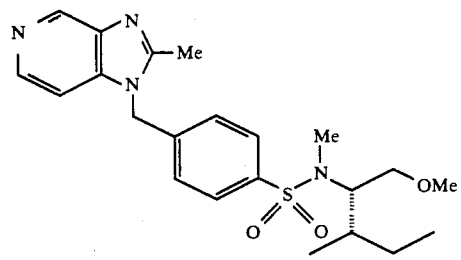

B

Regioisomer (A) Pale yellow oil (3% yield for last step after chromatography (silica: 5% methanol in DCM)):

Analysis Calculated for $C_{22}H_{30}N_4O_3S.0.9H_2O$

Requires C 59.14 H 7.17 N 12.54.
Found C 59.26 H 6.82 N 12.50.
i.r. (CDCl$_3$) 1605, 1330, 1150 cm$^{-1}$.

delta$_H$ 8.56 (1 H, s), 8.38 (1 H, d, J 5.5 Hz), 7.71 (2H, d, J 8.3 Hz), 7.58 (1 H, d, J 5.4 Hz), 7.10 (2H, d, J 8.3 Hz), 5.41 (2H, s), 3.76–3.64 (1 H, m), 3.26–3.19 (2H, m), 2.90 (3H, s), 2.64 (3H, s), 2.58 (3H, s), 1.60–1.40 (2H, m), 1.07–0.89 (1 H, m), 0.87–0.76 (6H, m).

Regioisomer (B): Pale yellow oil (3% yield):
i.r. (CDCl$_3$) 1605, 1330, 1150 cm$^{-1}$.
delta$_H$ 8.99 (1 H, s) 8.32 (1 H, d, J 5.6 Hz), 7.73 (2H, d, J 8.3 Hz), 7.15–7.08 (3H, m), 5.37 (2H, s), 3.78–3.65 (1 H, m), 3.30–3.23 (2H, m), 2.94 (3H, s), 2.67 (3H, s), 2.57 (3H, s), 1.60–1.39 (2H, m), 1.04–0.89 (1 H, m), 0.88–0.78 (6H, m).

EXAMPLE 41

N-Methyl-N-(S)-1-isobutyl-2-ethoxyethyl 4-(1 H-2-methylbenzimidazoylmethyl)benzenesulphonamide

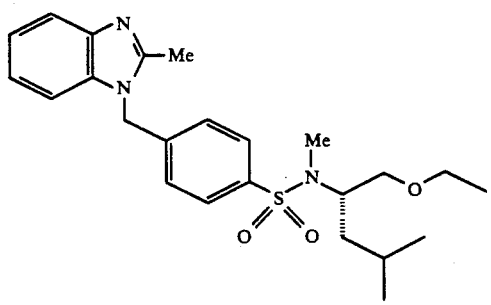

N-Methyl-N-(S)-1-isobutyl-2-ethoxyethyl 4-(1 H-2-methylbenzimidazoylmethyl) benzenesulphonamide was prepared by the method of Example 1 Step (c) employing N-methyl-N-(S)-1-isobutyl-2-ethoxyethyl 4-bromomethylbenzenesulphonamide in lieu of N-1-methylhexyl 4-bromomethylbenzenesulphonamide.

Colourless oil (32% yield after chromatography (silica: 4% methanol in DCM):

Analysis Calculated for $C_{24}H_{33}N_3O_3S.0.5H_2O$

Requires C 63.79 H 7.48 N 9.20.
Found C 63.69 H 7.57 N 9.28.
i.r. (CDCl$_3$) 3040, 1540, 1340, 1150 cm$^{-1}$.

delta$_H$ 7.80 (2H, br d, J 8.5 Hz), 7.75 (1 H, dd, J 6.6, 1.1 Hz), 7.30–7.17 (3H, m), 7.14 (2H, br d, J 8.5 Hz), 5.38 (2H, s), 4.21–4.10 (1 H,.m), 3.33–3.11 (4H, m), 2.70 (3H, s), 2.58 (3H, s), 1.65–1.48 (1 H, m), 1.38–1.12 (2H, m), 0.91 (3H, t, J 7.1 Hz), 0.90 (3H, d, J 6.4,,Hz), 0.89 (3H, d, J 6.5 Hz).

delta$_C$ 151.36, 142.60, 140.17, 140.05, 135.00, 128.21, 126.33, 122.40, 122.26, 119.26, 109.05, 70.67, 66.20, 54.86, 46.57, 37.96, 24.34, 23.14, 21.93, 14.63.

EXAMPLE 42

(A) N-Methyl-N-(S)-1-isobutyl-2-ethoxyethyl 4-(1 H-2-methyl-5-fluorobenzimidazoylmethyl) benzenesulphonamide and (B) N-methyl-N-(S)-1-isobutyl-2-ethoxyethyl 4-(1 H-2-methyl-6-fluorobenzimidazoylmethyl)benzenesulphonamide

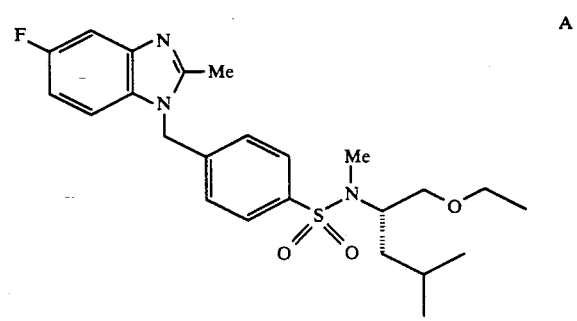

A

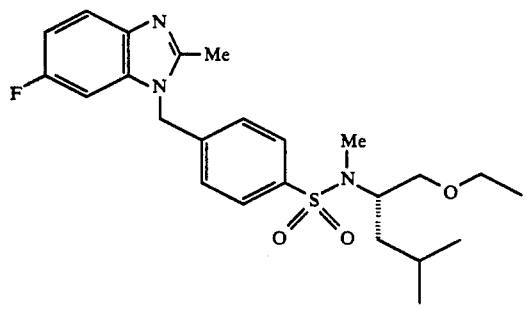

(a) 2-Methyl-5-fluorobenzimidazole

Ethyl acetimidate hydrochloride (37.1 g, 0.3 mol) was added to a stirred suspension of 4-fluoro-orthophenylenediamine (12.6 g, 0.1 mol) in ethanol (150 ml) at 0° C. The mixture was allowed to warm up to room temperature and stirred overnight. The solvent was removed under reduced pressure and the residue extracted into ethyl acetate (100 ml), washed with water (3×100 ml), dried over anhydrous magnesium sulphate, filtered and evaporated. Crystallisation from ethyl acetate gave 2-methyl-5-fluorobenzimidazole (7.7 g, 51%) as a brown crystalline solid.

m.p. 177°-178° C.

delta$_H$ 7.46 (1 H, dd, J 8.8, 4.7 Hz), 7.22 (1 H, dd, J 8.9, 2.4 Hz), 6.98 (1 H, ddd, J 9.7, 8.9, 2.4 Hz), 2.65 (3H, s).

(b) N-Methyl-N-(S)-1-isobutyl-2-ethoxyethyl 4-(1 H-2-methyl-5-fluorobenzimidazoylmethyl) benzenesulphonamide and N-methyl-N-(S)-1-isobutyl-2-ethoxyethyl 4-(1 H-2-methyl-6-fluorobenzimidazoylmethyl)benzenesulphonamide N-Methyl-N-(S)-1-isobutyl-2-ethoxyethyl 4-(1 H-2-methyl-5-fluorobenzimidazoylmethyl) benzenesulphonamide (A) and N-methyl-N-(S)-1-isobutyl-2-ethoxyethyl 4-(1 H-2-methyl-6-fluorobenzimidazoylmethyl)-benzenesulphonamide (B) were prepared by the method of Example 1 Step (c) employing 2-methyl-5-fluorobenzimidazole in lieu of 2-methylbenzimidazole and N-methyl-N-(S)-1-isobutyl-2-ethoxyethyl 4-bromomethyl-benzenesulphonamide in lieu of N-1-methylhexyl 4-bromomethylbenzenesulphonamide in the final step.

Regioisomers (A) and (B) were obtained as a mixture.

Yellow oil (35% yield for last step after chromatography (silica:4% methanol in DCM):

Analysis Calculated for $C_{24}H_{32}FN_3O_3S$

Requires C 62.45 H 6.99 N 9.10.
Found C 62.29 H 7.00 N 9.23.

i.r. (CDCl$_3$) 2960, 1400, 1340, 1150 cm$^{-1}$.

delta$_H$ 7.80 (2H, d, J 8.3 Hz), 7.64 (0.6H, dd, J 8.8, 4.8 Hz), 7.40 (0.4H, dd, J 9.3, 2.4 Hz), 7.11 (2H, d, J 8. 1 Hz),7.06 (0.4H, dd, J 8.8, 4.5 Hz), 6.96 (0.4H, m), 6.93 (0.6H, dd, J 9.0, 2.4 Hz), 6.83 (0.6H, dd, J 8.5, 2.4 Hz), 5.36 (0.8 H, s), 5.33 (1.2 H, s), 4.20-4.10 (1 H, m), 3.32-3.12 (4H, m), 2.69 (3H, s), 2.57 (3H, s), 1.62-1.51 (1 H, m), 1.38-1.11 (2H, m), 0.89 (3H, d, J 6.4 Hz), 0.89 (3H, t, J 6.9 Hz), 0.88 (3H, d, J 6.6 Hz).

EXAMPLE 43

N-Allyl-N-(S)-1-isobutyl-2-ethoxyethyl 4-(1 H-2-methylbenzimidazoylmethyl)benzenesulphonamide

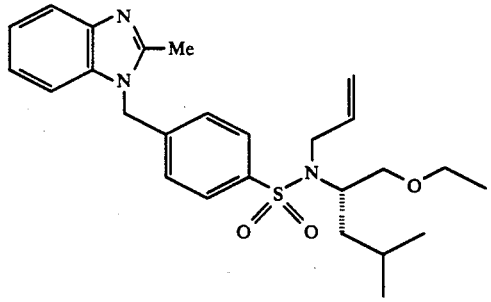

N-Allyl-N-(S)-1-isobutyl-2-ethoxyethyl 4-(1 H-2-methylbenzimidazoylmethyl) benzenesulphonamide was prepared by the method of Example 35 Steps (a) and (b) employing allyl bromide in lieu of methyl iodide in Step (a) and 2-methylbenzimidazole in lieu of 2-methylimidazo (4,5-c]pyridine in Step (b).

Colourless oil (80% yield for last step after chromatography (silica: 5% methanol in DCM):

i.r. (CDCl$_3$) 2210, 1330, 1150 cm$^{-1}$.

delta$_H$ 7.69-7.62 (3H, m), 7.27-6.97 (5H, m), 5.95-5.75 (1 H, m), 5.20 (2H, s), 5.17-4.92 (2H, m), 3.95 (1 H, m), 3.70 (2H, d, J 6.2 Hz), 3.25-3.04 (4H, m), 2.43 (3H, s), 1.52-1.05 (3H, m), 0.83 (3H, t, J 7.0 Hz), 0.76 (6H, d, J 6.5 Hz).

delta$_C$ 151.32, 142.30, 140.70, 140.02, 135.73, 134.85, 127.95, 126.10, 122.12, 121.88, 118.83, 116.63, 108.92, 71.00, 65.83, 55.84, 46.35, 46.22, 39.09, 24.02, 22.54, 21.81, 14.59, 13.52.

EXAMPLE 44

(A) N-Ethyl-N-1-allyl-2-ethoxyethyl 4-(3H-2-methylimidazo(4,5-c]-pyridylmethyl) benzenesulphonamide and (B) N-ethyl-N-1-allyl-2-ethoxyethyl 4-(1 H-2-methylimidazo[4,5-c]pyridylmethyl)benzenesulphonamide

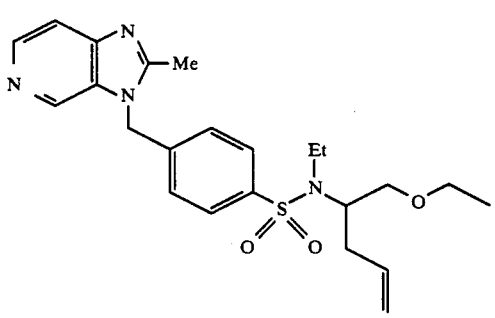

-continued

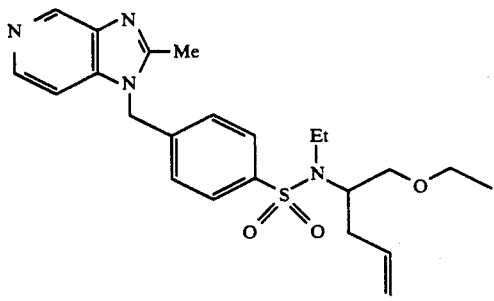

B (A) N-Ethyl-N-1-allyl-2-ethoxyethyl 4-(3H-2-methylimidazo[4,5-c]-pyridylmethyl) benzenesulphonamide and (B) N-ethyl-N-1-allyl-2-ethoxyethyl 4-(1 H-2-methylimidazo[4,5-c]pyridylmethyl)benzenesulphonaimide were prepared by the method of Example 19 Steps (b) and (c) starting from N-ethyl D,L-allyl glycinol ethyl ether.

Regioisomer (A): Yellow oil (5% yield for last step after chromatography (silica: 5% methanol in DCM)):
  i.r. (CDCl₃) 3670, 2980, 2210, 1605, 1330, 1150 cm⁻¹.
  delta_H 8.59 (1 H, s), 8.41 (1 H, d, J 5.5 Hz), 7.80 (2H, d, J 8.3 Hz), 7.62 (1 H, d, J-5.4 Hz), 7.12 (2H, d, J 8.2 Hz), 5.62–5.50 (1 H, m), 5.43 (2H, s), 5.01–4.89 (2H, m), 3.96–3.90 (1 H, m), 3.41–3.11 (5H, m), 2.60 (3H, S), 2.38–2.17 (3H, m), 1.15 (3H, t, J 7.1 Hz), 0.94 (3H, t, J 7.0 Hz).
  delta_C 153.62, 146.48, 140.99, 140.37, 137.74, 133.01, 131.61, 130.88, 126.93, 125.06, 116.09, 112.70, 69.56, 64.89, 56.48, 47.70, 37.85, 34.01, 15.13, 13.49, 12.56.

Regioisomer (B): Yellow oil (7% yield):
  i.r. (CDCl₃) 3680, 2980, 2220, 1610, 1330, 1150 cm⁻¹.
  delta_H 8.98 (1 H, s), 8.30 (1 H, d, J 5.6 Hz), 7.75 (2H, d, J 8.3 Hz), 7.11–7.04 (3H, m), 5.58–5.47 (1 H, m), 5.34 (2H, s), 4.98–4.85 (2H, m), 3.91–3.87 (1 H, m), 3.34–3.08 (5H, m), 2.54 (3H, s), 2.35–2.15 (3H, m), 1.13 (3H, t, J 7.1 Hz), 0.92 (3H, t, J 7.0 Hz).
  delta_C 151.95, 140.64, 140.52, 140.22, 138.78, 138.40, 137.79, 132.98, 126.61, 125.03, 116.06, 103.29, 69.52, 64.86, 56.44, 45.42, 37.81, 33.94, 15.12, 13.49, 12.51.

EXAMPLE 45

N-Isobutoxycarbonyl-N-(S)-1-isobutyl-2-ethoxyethyl 4-(1 H-2-methylbenzimidazoylmethyl)benzenesulphonamide

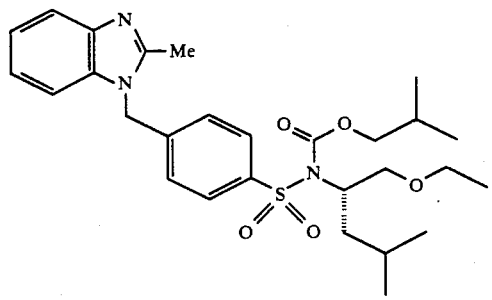

(a) N-Isobutoxycarbonyl-N-(S)-1-isobutyl-2-ethoxyethyl 4-bromomethylbenzenesulphonamide A solution of potassium bis(trimethylsilyl)amide (0.5M in THF, 1 ml, 0.5 mmol) was added to a stirred solution of N-(S)-1-isobutyl-2-ethoxyethyl 4-bromomethylbenzenesulphonamide (0.20 g, 0.53 mmol) in dry THF (40 ml) at room temperature under argon. The reaction mixture was cooled to 0° C. and isobutyl chloroformate (0.07 ml, 0.54 mmol) was added. The mixture was allowed to warm to room temperature and was stirred overnight. The solvent was removed under reduced pressure and the residue taken up in ethyl acetate (80 ml) and aqueous ammonium chloride (40 ml) added. The organic layer was separated, washed with brine (40 ml), dried over anhydrous sodium sulphate, filtered and concentrated under reduced pressure. The residue was purified by chromatography (silica: 15% ethyl acetate in hexane) to give N-isobutoxycarbonyl-N-(S)-1-isobutyl-2-ethoxyethyl 4-bromo-methylbenzenesulphonamide (100 mg, 40%) as a colourless oil.

delta_H 8.07 (2H, m), 7.47 (2H, m), 4.84 (1 H, m), 4.59 (0.8H, s), 4.47 (1.2H, s), 3.95–3.75 (3H, m), 3.60–3.34 (3H, m), 1.98–1.63 (3H, m), 1.41 (1 H, m), 1.14 (3H, t, J 7.0 Hz), 1.00 (3H, d, J 6.4 Hz), 0.96 (3H, d, J 6.7 Hz), 0.80–0.74 (6H, m).

(b) N-Isobutoxycarbonyl-N-(S)-1-isobutyl-2-ethoxyethyl 4-(1 H-2-methylbenzimidazoylmethyl) benzenesulphonamide N-Isobutoxycarbonyl-N-(S)-1-isobutyl-2-ethoxyethyl 4-(1 H-2-methylbenzimidazoylmethyl) benzenesulphonamide was prepared by the method of Example 35 Step (b) starting from N-isobutoxycarbonyl-N-(S)-1-isobutyl-2-ethoxyethyl 4-bromomethylbenzenesulphonamide and 2-methylbenzimidazole.

Colourless oil (61% yield for last step after chromatography (silica: 5% methanol in DCM):
  i.r. (CDCl₃) 2220, 1720, 1350, 1115 cm⁻¹.
  delta_H 8.01 (1 H, d, J 8.4 Hz), 7.73 (1 H, d, J 7.3 Hz), 7.28–7.08 (5H, m), 5.35 (2H, s), 4.80 (1 H, m), 3.88–3.73 (3H, m), 3.51–3.31 (3H, m), 2.54 (3H, s), 1.93–1.63 (3H, m), 1.45–1.33 (1 H, m), 1.04 (3H, t, J 7.0 Hz), 0.98 (3H, d, J 6.5 Hz), 0.94 (3H, d, J 6.7 Hz), 0.75 (3H, d, J 6.8 Hz), 0.73 (3H, d, J 6.6 Hz).
  delta_C 152.03, 151.48, 142.49, 141.08, 140.29, 135.03, 129.38, 125.90, 122.49, 122.30, 119.21, 109.02, 73.09, 71.80, 70.55, 66.20, 57.44, 46.54, 39.65, 27.51, 24.99, 23.03, 22.16, 18.75, 15.02, 13.77.

EXAMPLE 46

(A) N-Isobutoxycarbonyl-N-(S)-1-isobutyl-2-ethoxyethyl 4-(3H-2-methylimidazo[4,5-c]pyridylmethyl) benzenesulphonamide and (B) N-isobutoxycarbonyl-N-(S)-1-isobutyl-2-ethoxyethyl 4-(1 H-2-methylimidazo[4,5-c]pyridylmethyl) benzenesulphonamide

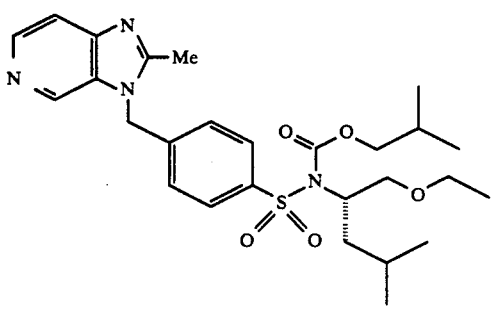

A

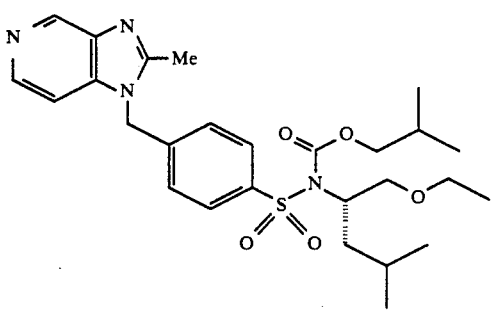

B (A) N-Isobutoxycarbonyl-N-(S)-1-isobutyl-2-ethoxyethyl 4-(3H-2-methylimidazo[4,5-c]pyridylmethyl) benzenesulphonamide and (B) N-isobutoxycarbonyl-N-(S)-1-isobutyl-2-ethoxyethyl 4-(1 H-2-methylimidazo[4,5-c]pyridylmethyl) benzenesulphonamide were prepared by the method of Example 45 employing 2-methylimidazo[4,5-c]pyridine in lieu of 2-methylbenzimidazole.

Regioisomer (A) : Pale yellow oil (12% yield for last step after chromatography (silica: 4% methanol in DCM)):

i.r. (CDCl$_3$) 2210, 1720, 1610, 1395, 1170 cm$^{-1}$.

delta$_H$ 8.43 (1 H, s), 8.26 (1 H, d, J 5.5 Hz), 7.86 (2H, d, J 8.5 Hz), 7.46 (1 H, d, J 5.9 Hz), 6.99 (2H, d, J 8.4 Hz), 5.31 (2H, s), 4.69-4.59 (1 H, m), 3.72-3.58 (3H, m), 3.38-3.13 (3H, m), 2.44 (3H, s), 1.78-1.49 (3H, m), 1.30-1.19 (1 H, m), 1.12-0.73 (9H, m), 0.60 (3H, d, J 6.6 Hz), 0.58 (3H, d, J 6.7 Hz).

delta$_C$ 154.70, 151.60, 147.44, 141.86, 140.14, 140.04, 132.57, 131.97, 129.18, 125.71, 113.59, 72.77, 70.13, 65.83, 57.16, 46.61, 39.27, 27.14, 24.60, 22.70, 21.78, 18.37, 14.64, 13.49.

Regioisomer (B): White foam (16% yield):
i.r. (CDCl$_3$) 2210, 1720, 1610, 1345, 1135 cm$^{-1}$.

delta$_H$ 8.76 (1 H, s), 8.08 (1 H, d, J 4.8 Hz), 7.76 (2H, d, J 8.4 Hz), 6.94-6.86 (3H, m), 5.18 (2H, s), 4.62-4.51 (1 H, m), 3.64-3.51 (3H, m), 3.31-3.05 (3H, m), 2.33 (3H, s), 1.71-1.41 (3H, m), 1.22-1.11 (1 H, m), 0.81-0.69 (9H, m), 0.52 (3H, d, J 6.7 Hz), 0.50 (3H, d, J 6. 6 Hz)

delta$_C$ 152.94, 151.44, 141.34, 141.08, 139.99, 139.81, 139.61, 139.26, 128.93, 125.55, 104.35, 72.59, 69.92, 65.70, 65.63, 57.01, 46.19, 39.08, 26.97, 24.43, 22.56, 21.62, 18.24, 14.51, 13.29.

EXAMPLE 47

N-Benzyloxycarbonyl-N-(S)-1-isobutyl-2-ethoxyethyl 4-(1 H-2-methylbenzimidazoylmethyl)benzenesulphonamide

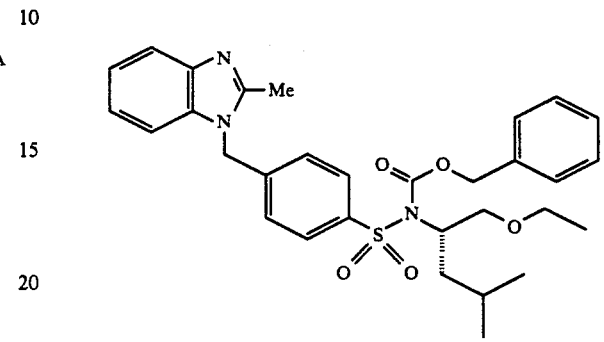

N-Benzyloxycarbonyl-N-(S)-1-isobutyl-2-ethoxyethyl 4-(1 H-2-methylbenzimidazoylmethyl) benzenesulphonamide was prepared by the method of Example 45 Step (a) followed by the method of Example 35 Step (b) starting from benzyl chloroformate in lieu of isobutyl chloroformate and employing 2-methylbenzimidazole in lieu of 2-methylimidazo [4,5-c]pyridine in the final step.

Colourless oil (21% yield for last step after chromatography (silica: 4% methanol in DCM)):

i.r. (CDCl$_3$) 2105, 1725, 1605, 1400, 1330, 1150 cm$^{-1}$.

delta$_H$ 7.71-7.62 (3H, m), 7.28-7.08 (8H, m), 6.99 (2H,,,.d, J 8.3 Hz), 5.21 (2H, s), 4.38 (1 H, d, J 15.7 Hz), 4.19 (1 H, d, J 15.7 Hz), 4.00 (1 H, m), 3.24-3.02 (4H, m), 2.47 (3H, s), 1.48-1.32 (1 H, M), 1.16-0.86 (2H, M), 0.82 (3H, t, J 6.9 Hz), 0.72 (3H, d, J 6.4 Hz), 0.59 (3H, d, J 6.6 Hz).

delta$_C$ 151.29, 142.36, 140.74, 139.95, 137.54, 134.85, 128.01, 127.90, 127.81, 127.11, 126.08, 122.14, 121.91, 118.88, 108.92, 70.81, 65.77, 56.22, 47.77, 46.19, 39.24, 23.97, 22.41, 21.77, 14.61, 13.55.

EXAMPLE 48

(A) N-Ethoxycarbonyl-N-(S)-1-isobutyl-2-ethoxyethyl 4-(3H-2-methylimidazo [4,5-c]pyridylmethyl)benzenesulphonamide and (B) N-ethoxycarbonyl-N-(S)-1-isobutyl-2-ethoxyethyl 4-(1 H-2-methylimidazo(4,5-c]pyridylmethyl) benzenesulphonamide

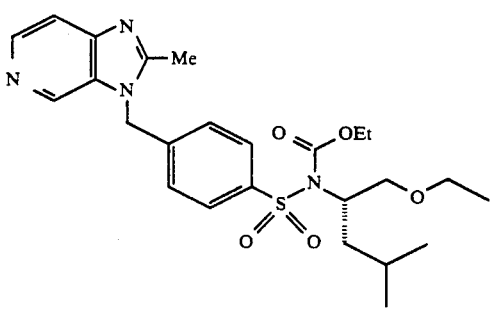

A

-continued

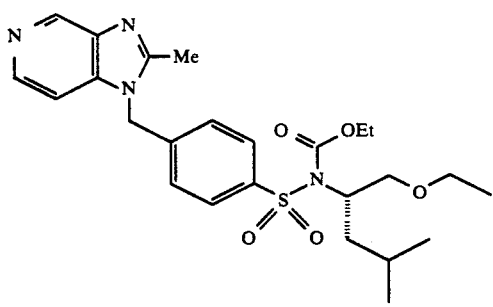

(A) N-Ethoxycarbonyl-N-(S)-1-isobutyl-2-ethoxyethyl 4-(3H-2-methylimidazo[4,5-c]pyridylmethyl)benzenesulphonamide and (B) N-ethoxycarbonyl-N-(S)-1-isobutyl-2-ethoxyethyl 4-(1 H-2-methylimidazo[4,5-c]pyridylmethyl) benzenesulphonamide were prepared by the method of Example 45 Step (a) followed by the method of Example 35 Step (b) starting from ethyl chloroformate in lieu of isobutyl chloroformate.

Regioisomer (A) : White foam (6% yield for last step after chromatography (silica: 7% methanol in DCM)):

i.r. (CDCl$_3$) 2220, 1725, 1605, 1350, 1170 cm$^{-1}$.

delta$_H$ 8.52 (1 H, s), 8.35 (1 H, d, J 5.5 Hz), 7.96 (2 H, d, J 8.4, Hz), 7.56 (1 H, d, J 5. 5 Hz), 7.08 (2H, d, J 8.3 Hz), 5. 40 (2H, s), 4.72 (1 H, br s), 4.08-3.94 (2H, m), 3.76 (1 H, t, J 9.8 Hz), 3.47-3.22 (3H, m), 2.54 (3H, s), 1.85-1.73 (1 H, m), 1.68-1.52 (1 H, m), 1.37-1.25 (1 H, m), 1.03-0.87 (12H, m).

delta$_C$ 154.88, 151.61, 147.68, 142.17, 140.33, 140.14, 132.98, 132.13, 129.63, 125.80, 113.87, 70.42, 62.79, 57.34, 46.88, 39.40, 24.82, 22.92, 21.94, 14.86, 13.74, 13.65.

Regioisomer (B): Colourless oil (10% yield for last step):

i.r. (CDCl$_3$) 2120, 1725, 1615, 1350, 1170 cm$^{-1}$.

delta$_H$ 8.85 (1 H, s), 8.17 (1 H, d, J 5.5 Hz), 7.84 (2H, d, J 7.9 Hz), 7.01-6.95 (3H, m), 5.25 (2H, s), 4.69-4.57 (1 H, m), 3.92 (2H, q, J 7.0 Hz), 3.67 (1 H, t, J 9.8 Hz), 3.39-3.13 (3H, m), 2.42 (3H, s), 1.77-1.65 (1 H, m), 1.57-1.47 (1 H, m), 1.29-1.17 (1 H, m), 0.95-0.78 (12H, m).

delta$_C$ 153.06, 151.41, 141.60, 141.39, 140.08, 139.93, 139.78, 139.43, 129.33, 125.62, 104.45, 70.18, 65.82, 62.57, 57.05, 46.41, 39.19, 24.60, 22.73, 21.75, 14.68, 13.50.

EXAMPLE 49

N-Acetyl-N-(S)-1-isobutyl-2-ethoxyethyl 4-(1 H-2-methylimidazo-[4,5-c]pyridylmethyl)benzenesulphonamide

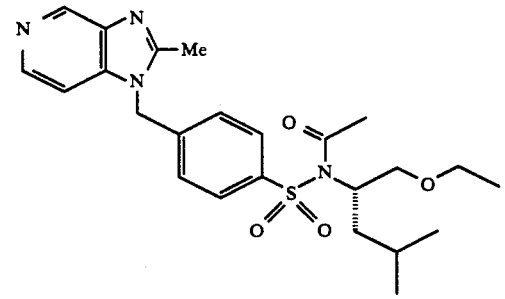

A solution of potassium bis(trimethylsilyl)amide in THF (0.5M, 0.23 ml, 0.12 mmol) was added to a stirred solution of N-(S)-1-isobutyl-2-ethoxyethyl 4-(1 H-2-methylimidazo[4,5-c]pyridylmethyl)benzenesulphonamide (50 mg, 0.12 mmol) in dry THF (10 ml) under argon at 0° C. Acetyl chloride (0.025 ml, 0.35 mmol) was added and the mixture stirred for 10 min. The solvent was removed under reduced pressure, the residue was taken up in ethyl acetate (20 ml) and washed with brine (20 ml), dried over anhydrous sodium sulphate, filtered and evaporated. Chromatography (silica: 5% methanol in DCM) of the residue gave N-acetyl-N-(S)-1-isobutyl-2-ethoxyethyl 4-(1 H-2-methylimidazo[4,5-c]pyridylmethyl) benzenesulphonamide (20 mg, 36%) as a pale yellow oil.

i.r. (CHCl$_3$) 2220, 1690, 1350, 1140 cm$^{-1}$.

delta$_H$ 9.06 (1 H, br s), 8.41 (1 H, br s), 8.06 (2H, d, J 8.4 Hz), 7.19-7.10 (3H, m), 5.43 (2H, s), 4.00-3.93 (1 H, m), 3.51-3.38 (4H, m), 2.61 (3H, s), 2.21 (3H, s), 1.93-1.81 (1 H, m), 1.76-1.58 (2H, m), 1. 0 4 (3H, t, J 7. 0 Hz), 0. 95 (6H, d, J 6. 2 Hz)

EXAMPLES 50-51

The compounds of Examples 50-51 were prepared by the method of Example 35 Steps (c)-(h) employing the appropriate carboxylic anhydride in lieu of acetic anhydride in the last step.

50. N-Methyl-N-(S)-1-isobutyl-2-ethoxyethyl 4-(1 H-2-ethylimidazo-[4,5-c]pyridylmethyl)benzenesulphonamide

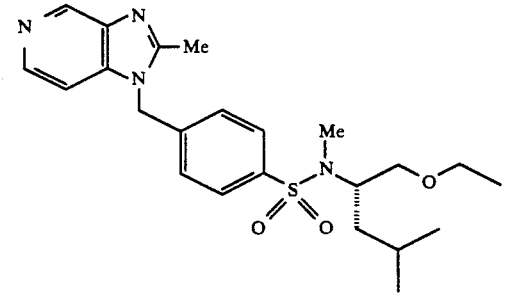

White crystalline solid (29% yield for last step after chromatography (silica: 5% methanol in DCM)): m.p. 108°-112° C.

i.r. (CDCl$_3$) 2960, 1605, 1330, 1145 cm$^{-1}$.

delta$_H$ 8.97 (1 H, br s), 8.25 (1 H, br s), 7. 67 (2H d, J 8.2 Hz), 7.07 (1 H, br s), 7.00 (2H, d, J 8.1 Hz), 5.31 (2H, s), 4.04 (1 H, m), 3.19-3.04 (4H, m), 2.81-2.72 (2H, q, J 7.5 Hz), 2.59 (3H, s), 1.47 (1 H, m), 1.37-1.31 (3 H, t, J 7.5 Hz), 1.27-1.04(2H, m), 0.80-0.75 (9H, m).

delta$_C$ 157.63, 141.76, 140.20, 140.04, 139.20, 126.08, 126.14, 104.62, 70.55, 65.97, 54.77, 46.28, 37.76, 24.13, 22.93, 21.75, 20.64, 11.01.

51. N-Methyl-N-(S)-1-isobutyl-2-ethoxyethyl 4-(1 H-2-n-pentylimidazo

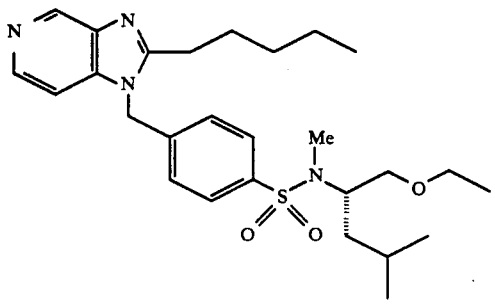

White crystalline solid (55% yield for last step after chromatography (silica: 6% methanol in chloroform) and crystallisation from ethyl acetate/DIPE): m.p. 81°-82° C.

i.r. (DCM) 2920-2850, 1605, 1110 cm$^{-1}$.

delta$_H$ 8.90 (1 H, s), 8.18 (1 H, d, J 5.5 Hz), 7.61 (2H, d, J 8.3 Hz), 7.00 (1 H, d, J 5.5 Hz), 6.96 (2H, d, J 8.4 Hz), 5.28 (2H, s), 4.05-3.95 (1 H, m), 3.16-2.96 (4H, m), 2.69 (2H, t, J 7.6 Hz), 2.54 (3H, s), 1.78-1.66 (2H, m), 1.48-1.31 (1 H, m), 1.30-0.97 (6H, m), 0.76-0.70 (12H, m).

delta$_C$ 156.84, 141.36, 140.01, 139.89, 139.52, 139.17, 127.93, 126.02, 104.65, 70.42, 65.85, 54.65, 46.24, 37.65, 31.11, 28.01, 27.04, 26.53, 24.03, 22.84, 21.94, 21.63, 14.52.

EXAMPLE 52

(A) N-Methyl-N-(S)-1-isobutyl-2-t-butyldiphenylsilyloxyethyl 4-(3H-2-methylimidazo [4,5-c]pyridylmethyl)benzenesulphonamide and (B) N-methyl-N-(S)-1-isobutyl-2-t-butyldiphenylsilyloxyethyl 4-(1 H-2-methylimidazo (4,5-c]pyridylmethyl)benzenesulphonamide

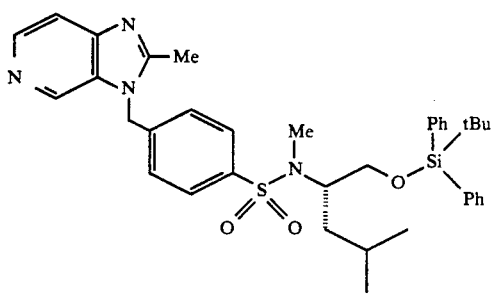

A

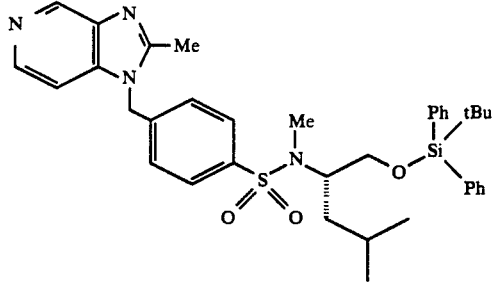

B (a) N-(S)-1-Isobutyl-2-ethan-1-ol 4-bromomethylbenzenesulphonamide

N-(S)-1-Isobutyl-2-ethan-1-ol 4-bromomethylbenzenesulphonamide was prepared by the method of Example 1 Step (b) employing L-leucinol in lieu of 2-aminoheptane and 1.5 equivalents of triethylamine.

Colourless oil: (37% yield after chromatography(silica: 50% ethyl acetate in hexane).

delta$_H$ 7.91 (2H, d, J 8.3 Hz), 7.53 (2H, d, J 8.4 Hz), 5.31 (1 H, d, J 7.7 Hz), 4.62 (2H, s), 3.62-3.44 (2H, m), 3.36-3.27 (1 H, m), 2.60 (1 H, br s), 1.45-1.37 (1 H, m), 1.25 (2H, t, J 7.2 Hz), 0.76 (3H, d, J 6. 5 Hz), 0. 62 (3H, d, J 6. 4 Hz)

(b) N-(S)-1-Isobutyl-2-t-butyldiphenylsilyloxyethyl 4-(3H-2-methylimidazo[4,5-c]pyridylmethyl) benzenesulphonamide 2-t-Butyldiphenylsilyl chloride (12.3 ml, 47.1 mmol) and 4-dimethylaminopyridine (50 mg) were added to a solution of N-(S)-1-isobutyl -2-ethan-1-ol 4-bromomethylbenzenesulphonamide and diisopropylethylamine (37.3 ml, 0.21 mol) in dry DMF and the mixture stared at room temperature under argon overnight. Ethyl acetate was added and the mixture washed with aqueous ammonium chloride and brine. The combined aqueous washings were extracted with ethyl acetate and the combined organics dried over anhydrous sodium sulphate, filtered and concentrated to give N-(S)-1-isobutyl-2-t-butyldiphenylsilyloxyethyl 4-(3H-2-methylimidazo[4,5-c]pyridylmethyl) benzenesulphonamide which was used directly in the next step.

delta$_H$ 8.05-7.31 (14H, m), 4.89 (1 H, d, J 10.0 Hz), 4.58 (2H, s), 3.51-3.42 (2H, m), 3.40-3.23 (1 H, m), 1.78-1.69 (1 H, m), 1.55-1.32 (2H, m), 1.02 (9H, s), 0.77 (3H, d, J 6.6 Hz), 0.72 (3H, d, J 6.5 Hz)

(c) (A) N-Methyl-N-(S)-1-isobutyl-2-t-butyldiphenylsilyloxyethyl 4-(3H-2-methylimidazo(4,5-c]pyridylmethyl)benzenesulphonamide and (B) N-methyl-N-(S)-1-isobutyl-2-t-butyldiphenylsilyloxyethyl 4-(1 H-2-methylimidazo[4,5-c]pyridylmethyl)benzenesulphonamide (A) N-Methyl-N-(.S)-1-isobutyl-2-t-butyldiphenylsilyloxyethyl 4-(3H-2-methylimidazo(4,5-c]pyridylmethyl)benzenesulphonamide and (B) N-methyl-N-(S)-1-isobutyl-2-t-butyldiphenylsilyloxyethyl 4-(1H -2-methylimidazo[4,5-c]pyridylmethyl)benzenesulphonamide were prepared by the method of Example 35 Steps (a) and (b) starting from N-(S)-1-isobutyl-2-t-butyldiphenylsilyloxyethyl 4-(3H-2-methylimidazo [4,5-c]pyridylmethyl)benzenesulphonamide.

Regioisomers (A) and (B) were separated by chromatography (silica: 5% methanol in DCM).

Regioisomer (B): Yellow oil (5% yield for last step): i.r. (CDCl$_3$) 2930, 2860, 2250, 1610, 1585, 1335 cm$^{-1}$.

delta$_H$ 9.03 (1 H, s), 8.32 (1 H, d, J 5.6 Hz), 7.68 (2H, d, J 8.3 Hz), 7.58–7.50 (4H, m), 7.42–7.28 (6H, m), 7.03 (1 H, d, J 5.4 Hz), 6.94 (2H, d, J 8.0 Hz), 5.29 (2H, s), 4.11–4.07 (1 H, m), 3.59–3.45 (2H, m), 2.70 (3H, s), 2.49 (3H, s), 1.45–1.23 (3H, M), 0.99 (9H, s), 0.82 (3H, d, J 5.0 Hz), 0.80 (3H, d, J 5.8 Hz).

delta$_C$ 153.41, 142.02, 141.86, 140.40, 140.22, 139.81, 139.17, 5.38, 135.32, 133.22, 129.66, 127.92, 127.60, 126.45, 104.55, 64.64, 56.43, 46.61, 46.02, 37.43, 29.06, 26.66, 24.27, 22.92, 22.03, 13.79, 11.10.

EXAMPLE 53

(A) N-1-Isobutylpentyl 4-(3H-2-methylimidazo[4,5-c]pyridylmethyl)benzenesulphonamide and (B) N-1-Isobutylpentyl 4-(1 H-2-methylimidazo [4,5-c]pyridylmethyl)benzenesulphonamide

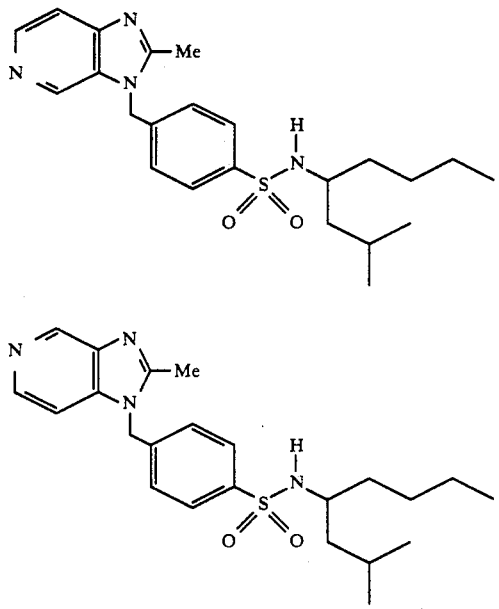

(a) 2-Methyloctan-4-ol

A solution of isovaleraldehyde (5.0 g, 58 mmol) in dry THF (15 ml) was added to a stirred 2M THF solution of n-butylmagnesium chloride (30 ml, 60 mmol) at 0° C. under argon. The mixture was allowed to warm up to room temperature and was stirred overnight. The reaction was quenched by the addition of aqueous ammonium chloride (50 ml) and extracted with diethyl ether (200 ml). The organic extracts were dried over anhydrous potassium carbonate, filtered and concentrated to give 2-methyloctan-4-ol (6.4 g, 77%) as a clear oil.

delta$_H$ 3.68–3.57 (1 H, m), 1.81–1.70 (2H, m), 1.42–1.15 (8H, m), 0.94–0.86 (9H, m).

(b) 2-Methyloctan-4-one

A solution of oxalyl chloride (4.2 ml, 49 mmol) in dry DCM (200 ml) was cooled to −78° C. under argon. Dimethylsulphoxide (6.9 ml, 98 mmol) was added slowly and the mixture stirred for 5 min. 2-Methyloctan-4-ol (6.4 g, 44 mmol) was added and the mixture stirred for 20 min. Triethylamine (30.7 ml, 0.22 mol) was added and after 5 min. the mixture was allowed to warm up to room temperature. Water (100 ml) was added, the organic layer separated and the aqueous layer extracted with DCM. The combined organic extracts were dried over anhydrous magnesium sulphate, filtered and concentrated to give 2-methyloctan-4-one (5.0 g, 79%) as a waxy oil.

delta$_H$ 2.30 (2H, t, J 7.4 Hz), 2.20 (2H, d, J 6.8 Hz), 2.13–2.00 (1 H, m), 1.53–1.41 (2H, m), 1.30 –1.15 (2H, m), 0.89–0.79 (9H, m)

(c) 2-Methyl-4-aminooctane

A mixture of 2-methyloctan-4-one (6.3 g, 44 mmol), sodium cyanoborohydride (3.0 g, 48 mmol), ammonium acetate (33.9 g, 0.44 mol) and 3Å molecular sieves in dry methanol (50 ml) was stirred overnight at room temperature under argon. The solvent was removed under reduced pressure and the residue taken up in chloroform (100 ml), filtered through a pad of celite and concentrated to give 2-methyl-4-aminooctane (1.6 g, 25%) as a yellow oil.

delta$_H$ 6.22 (2H, br s), 3.04 (1 H, m), 1.83–1.22 (9H, m), 0.96–0.84 (9 H, m).

(d) (A) N-1-Isobutylpentyl 4-(3H-2-methylimidazo[4,5-c]pyridylmethyl) benzenesulphonamide and (B) N-1-Isobutylpentyl 4-(1 H-2-methylimidazo [4,5-c]pyridylmethyl)benzenesulphonamide (A) N-1-Isobutylpentyl 4-(3H-2-methylimidazo[4,5-c]pyridylmethyl)benzenesulphonamide and (B) N-1-Isobutylpentyl 4-(1 H-2-methylimidazo [4,5-c]pyridylmethyl)benzenesulphonamide were prepared by the method of Example 1 Step (b) followed by the method of Example 17 starting from 2-methyl-4-aminooctane in lieu of 2-aminoheptane and employing 3:1 DMF/THF as solvent in the final coupling step.

Regioisomer (A) : Off white crystalline solid (9% yield for last step after chromatography (silica: 5–8% methanol in DCM) m.p. 166°–167° C.

i.r. (CDCl$_3$) 2960, 1610, 1330, 1150 cm$^{-1}$.

delta$_H$ 8.65 (1 H, br s), 8.42 (1 H, br s), 7.80 (2H, d, J 8.2 Hz), 7.64 (1 H, br s), 7.16 (2H, d, J 8.2 Hz), 5.45 (2H, s) 5.19 (1 H, d, J 8.5 Hz), 3.27–3.17 (1 H, m), 2.59 (3H, s), 1.52–1.44 (1 H, m), 1.41–1.22 (2H, m), 1.19–1.08 (6H, m), 0.74–0.69 (6H, m), 0.65 (3H, d, J 6.5 Hz).

delta$_C$ 155.10, 147.89, 142.16, 142.02, 139.39, 133.04, 132.21, 127.87, 126.74, 114.13, 52.45, 47.04, 44.61, 35.18, 27.12, 24.38, 22.69, 22.31, 22.03, 13.80.

Regioisomer (B): Off white crystalline solid (7% yield): m.p. 199°–200° C.

i.r. (CDCl$_3$) 2960, 1330, 1150 cm$^{-1}$.

delta$_H$ 9–01 (1 H, s), 8.36 (1 H, br s), 7.80 (2H, d, J 8.2 Hz), 7.13–7.10 (3H, m), 5.39 (2H, s), 5.13 (1 H, d, J 7.9 Hz), 3.27–3.19 (1 H, m), 2.57 (3H, s), 1.50–1.42 (1 H, m), 1.35–1.22 (2H, m), 1.19–1.09 (6H, m), 0.74–0.71 (6H, m), 0.66 (3H, d, J 6.5 Hz).

delta$_C$ 153.63, 142.02, 141.65, 141.49, 140.39, 139.29, 127.87, 126.65, 104.77, 52.49, 46.86, 44.64, 35.18, 27.13, 24.38, 22.69, 22.34, 22.09, 13.82.

EXAMPLE 54

(A) N-Benzyl-N-1-isobutylpentyl 4-(3H-2-methylimidazo(4,5-c]-pyridylmethyl) benzenesulphonamide and (B) N-benzyl-N-1-isobutylpentyl 4-(1 H-2-methylimidazo[4,5-c]pyridylmethyl)benzenesulphonamide

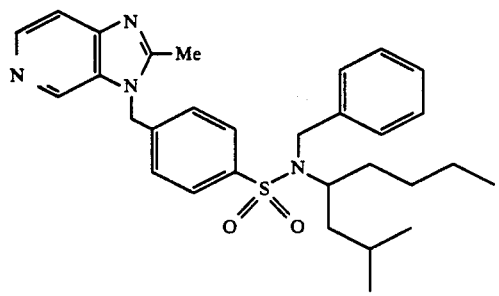

A

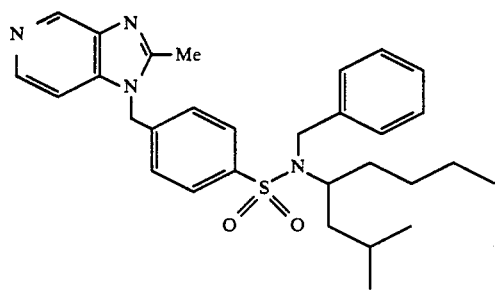

B (a) N-Benzyl-2-methyl-4-aminooctane

Benzylamine (3.1 ml, 28 mmol) was added to a stirred mixture of 2-methyloctan-4-one (4.0 g, 28 mmol) and 3A molecular sieves in dry, methanol (40 ml) under argon. The mixture was stirred at room temperature overnight. Sodium cyanoborohydride (1.77 g, 28 mmol) was added and the mixture stirred overnight. Stirring was stopped and the solution was decanted, from the molecular sieves, into saturated aqueous ammonium chloride. The mixture was filtered, concentrated, ethyl acetate added and the mixture washed with water. The organics were dried over anhydrous magnesium sulphate, filtered and concentrated to give a yellow oil. Chromatography (silica: 1% triethylamine and 10% ethylacetate in hexane) gave N-benzyl -2-methyl-4-aminooctane (3.0 g, 46%) as a yellow oil.

delta$_H$ 7.40–7.23 (5 H, m), 3.82 (1 H, AB, J 18.1 Hz), 3.79 (1 H, AB, J 18.1 Hz), 2.63 (1 H, m), 1.73 (1 H, m), 1.55–1.19 (9H, m), 1.02–0.87 (9 H, m).

(b) (A) N-Benzyl-N-1-isobutylpentyl 4-(3H-2-methylimidazo[4,5-c]-pyridylmethyl) benzenesulphonamide and (B) N-benzyl-N-1-isobutylpentyl 4-(1 H-2-methylimidazo[4,5-c]pyridylmethyl)benzenesulphonamide (A) N-Benzyl-N-1-isobutylpentyl 4-(3H-2-methylimidazo[4,5-c]-pyridylmethyl) benzenesulphonamide and (B) N-binzyl-N-1-isobutylpentyl 4-(1 H-2-methylimidazo[4,5-c]pyridylmethyl)benzenesulphonamide were prepared by the method of Example 1 Step (b) followed by the method of Example 17 starting from N-benzyl-2-methyl-4-aminooctane in lieu of 2-aminoheptane and employing 3:1 DMF/THF as solvent in the final coupling step.

Regioisomer (A) : Off white crystalline solid (4% yield for last step after chromatography (silica: 5–7% methanol in DCM)):

delta$_H$ 8.71 (1 H, s), 8.46 (1 H, d, J 5.3 Hz), 7.73 (2H, d, J 8.3 Hz), 7.69 (1 H, d, J 6.2 Hz), 7.36–7.20 (5H, m), 7.14 (2H, d, J 8.2 Hz), 5.47 (2H, s), 4.37 (1 H, d, J 15.6 Hz), 4.20 (1 H, d, J 15.6 Hz), 3.77–3.72 (1 H, m), 2.63 (3H, s), 1.47–1.36 (1 H, m), 1.27–1.13 (1 H, m), 1.08–0.87 (7H, m), 0.75 (3H, d, J 6.4 Hz), 0.69 (3H, t, J 6.9 Hz), 0.55 (3H, d, J 6.6 Hz).

delta$_C$ 155.73, 148.32, 141.79, 141.50, 139.11, 137.73, 133.00, 131.64, 128.39, 128.27, 128.09, 127.46, 126.67, 114.33, 57.49, 47.44, 47.11, 42.41, 32.62, 28.92, 24.36, 22.43, 22.31, 22.16, 13.76.

Regioisomer (B): Off white crystalline solid (4% yield):

delta$_H$ 9.06 (1 H, br s), 8.40 (1 H, br s), 7.73 (2H, d, J 8.3 Hz), 7.36–7.21 (5H, m), 7.15–7.10 (3H, m), 5.39 (2H, s), 4.38 (1 H, d, J 15.6 Hz), 4.21 (1 H, d, J 15.6 Hz), 3.76–3.70 (1 H, m), 2.60 (3H, s), 1.47–1.37 (1 H, m), 1.27–1.22 (1 H, m), 1.13–0.97 (7H, m), 0.75 (3H, d, J 6.4 Hz), 0.70 (3H, t, J 7.0 Hz), 0.56 (3H, d, J 6.7 Hz).

delta$_C$ 153.27, 142.08, 141.70, 141.16, 139.27, 137.78, 128.40, 128.28, 128.07, 127.49, 126.59, 104.61, 57.44, 47.47, 46.79, 42.41, 32.81, 28.92, 24.38, 22.44, 22.34, 22.22, 13.80.

EXAMPLE 55

(A) N-Ethyl-N-(S)-1-isobutyl-2-ethoxyethyl 3-chloro-4-(3H-2-methylimidazo [4,5-c]pyridylmethyl)benzenesulphonamide and (B) N-ethyl-N-(S)-1-isobutyl-2-ethoxyethyl 3-chloro-4-(1 H-2-methylimidazo [4,5-c]pyridylmethyl)benzenesulphonamide

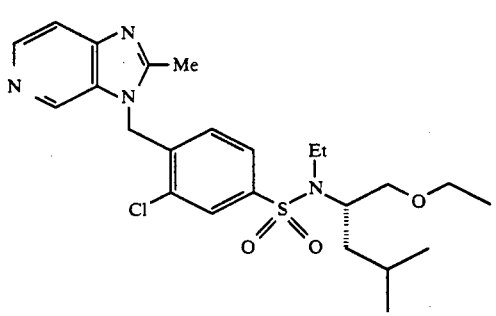

A

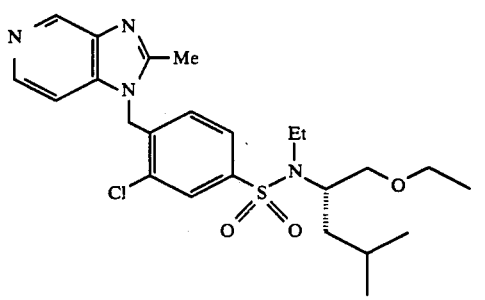

B (a) 3-Chloro-4-Bromomethylphenylsulphonyl Chloride

N-Bromosuccinimide (13.76 g, 76 mmol) was added to a stirred solution of 3-chloro-4-toluenesulphonyl chloride (12 g, 76 mmol) in CCl$_4$ (120 ml) under argon.

After one hour benzoyl peroxide (0.92 g, 3.8 mmol) was added and the reaction mixture refluxed overnight. The mixture was allowed to cool, the resulting white precipitate filtered off and the filtrate evaporated to a yellow oil. Purification of the residue by chromatography over silica gel (3% ethyl acetate in hexane) afforded 3-chloro-4-bromomethylphenylsulphonyl chloride (3.3 g, 14 %) as a colourless ol.

delta$_H$ 8.30-7.05 (3H, m), 4.62 (2H, s).

(b) N-Ethyl-N-(S)-1-isobutyl-2-ethoxyethyl 3-chloro-4-bromomethylbenzenesulphonamide N-Ethyl-N-(S)-1-isobutyl-2-ethoxyethyl 3-chloro-4-bromomethylbenzenesulphonamide was prepared following the procedure of Example 1 Step (b) utilizing 3-chloro-4-bromomethylphenylsulphonyl chloride in lieu of 4-bromomethylphenylsulphonyl chloride and N-ethyl L-leucinol ethyl ether in lieu of 2-aminoheptane.

Colourless oil (6% yield after purification by chromatography (silica: 3% ethyl acetate in hexane):

delta$_H$ 7.96-7.38 (3H, m), 4.70 (2H, s), 4.03 (1 H, m), 3.41-3.15 (6H, m), 1.80-1.55 (1 H, m), 1.35 (2H, m), 1.37-0.87 (6H, m), 0.90 (3H, d, J 6.1 Hz), 0.89 (3H, d, J 6.7 Hz).

(c) (A) N-Ethyl-N-(S)-1-isobutyl-2-ethoxyethyl 3-chloro-4-(3H-2-methylimidazo [4,5-c]pyridylmethyl)benzenesulphonamide and (B) N-ethyl-N-(S)-1-isobutyl-2-ethoxyethyl 3-chloro-4-(1 H-2-methylimidazo [4,5-c]pyridylmethyl)benzenesulphonamide (A) N-Ethyl-N-(S)-1-isobutyl-2-ethoxyethyl 3-chloro-4-(3H-2-methylimidazo [4,5-c]pyridylmethyl)benzenesulphonamide and (B) N-ethyl-N-(S)-1-isobutyl-2-ethoxyethyl 3-chloro-4-(1 H-2-methylimidazo [4,5-c]pyridylmethyl)benzenesulphonamide were prepared by the method of Example 17 utilizing N-Ethyl-N-(S)-1-isobutyl-2-ethoxyethyl 3-chloro-4-bromomethylbenzenesulphonamide in lieu of N-1,2-diphenylethyl 4-bromomethylbenzenesulphonamide and 3:1 THF/DMF as solvent.

Regioisomer (A): Colourless oil (1% yield after chromatography (silica: 5% methanol in DCM)):

delta$_H$ 8.40 (1 H, br s), 8.01 (1 H, d, J 1.5 Hz), 7.83 (1 H, br s), 7.72-7.65 (2H, m), 6.61 (1 H, d, J 8.5 Hz), 5.61 (2H, s), 4.06 (1 H, m), 3.36-3.13 (6H, m), 2.65 (3H, s), 1.63 (1 H, m), 1.50-1.36 (2H, m), 1.18 (3H, t, J 7.1 Hz), 1.01-0.86 (9H, m).

Regioisomer (B): Colourless oil (1% yield):
i.r. (CDCl$_3$) 2980, 1335, 1150 cm$^{-1}$.

delta$_H$ 9.10 (1 H, br s), 8.42 (1 H, br s), 8.00(1 H, d, J 1.8 Hz), 7.62 (1 H, dd, J 8.2, 1.8 Hz), 7.13 (1 H, s), 6.51 (1 H, d, J 8.2 Hz), 5.44 (2H, s), 4.08-3.97 (1 H, m), 3.38-3.14 (6H, m), 2.59 (3H, s), 1.65-1.52 (1 H, m), 1.42-1.22 (2H, m), 1.17 (3H, t, J 7.1 Hz), 0.93 (3H, t, J 7.0 Hz), 0.88 (6H, d, J 6.3 Hz).

delta$_C$ 153.78, 143.24, 141.75, 140.33, 136.16, 132.62, 129.12, 126.71, 126.61, 71.21, 66.26, 56.50, 44.98, 40.00, 38.77, 24.53, 22.85, 22.31, 16.55, 14.88.

COMPARATIVE EXAMPLE

N-Cyclohexyl-N-methyl 4-(1 H-imidazo[4,5-c]pyridylmethyl)benzamide

This compound is not within the scope of the invention: It has been included here as a comparative example. This compound was described in EP-A-0260613.

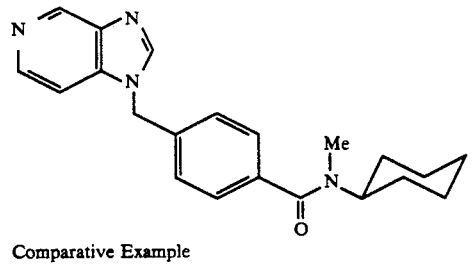

Comparative Example (a) N-Cyclohexyl-N-methyl 4-methylbenzamide

To an ice cold stirred solution of N-methylcylohexylamine (20 ml, 0.15 mol) and triethylamine (22 ml) in dry THF (100 ml) under argon was slowly added p-toluoyl chloride (20 ml, 0. 15 mol) . A white precipitate formed. The ice bath was removed and the mixture stirred at ambient temperature for 24 h. Ice cold 2M, hydrochloric acid (100 ml) was added and the organic layer separated. The aqueous layer was extracted with ethyl acetate (3×100 ml). The combined organics were washed with brine (3×100 ml), dried over anhydrous sodium sulphate, filtered and evaporated to give the crude amide, which was crystalised from hexane to give N-cyclohexyl-N-methyl 4-methylbenzamide (30.9 g, 87%) as a white crystalline solid.

m.p. 70°-71° C.
i.r. (nujol) 2920, 1640 cm$^{-1}$.

delta$_H$ 7.26 (2H, d, J 8.0 Hz), 7.18 (2H, d, J 8.3 Hz), 4.50, 3.50 (1 H, 2br m), 3.08-2.68 (3H, br m), 2.37 (3H, s), 1.93-0.93 (10H, br m).

(b) N-Cyclohexyl.-N-methyl 4-bromomethylbenzamide

Utilising the procedure described in Example 1 (a) employing N-cyclohexyl-N-methyl 4-methylbenzamide in lieu of p-toluene-sulphonyl chloride and tetrachloromethane as solvent yielded crude N-cyclohexyl-N-methyl 4-bromomethylbenzamide (67%) as an orange waxy solid.

i.r. (CH$_2$Cl$_2$) 2935, 1720 cm$^{-1}$.

delta$_H$ 7.46 (2H, d, J 8.1 Hz), 7.34 (2H, d, J 8.1 Hz), 4.51 (2H, s), 3.78, 3.50 (1 H, 2br m), 2.97 (3H, br s), 1.89-0.98 (10H, br m).

(c) N-Cyclohexyl-N-methyl 4-(1 H-imidazo[4,5-c]pyridylmethyl)benzamide

Sodium bis(trimethylsilyl)amide (22 ml of 1 M solution in THF) was added to a stirred solution of imidazo[4,5-c]pyridine (2.60 g, 0.02 mol) in dry THF (200 ml) under argon. A fine white precipitate formed. After 90 min. the mixture was treated with N-cyclohexyl-N-methyl 4-bromomethylbenzamide (6.20 g, 0.02 mol) dissolved in dry THF (50 ml). The mixture was allowed to warm to ambient temperature and stirred overnight. Methanol (1 ml) was added, followed by water and the product extracted using ethyl acetate (3×150 ml) The combined organic layers were washed,, with water (2×100 ml), dried over anhydrous potassium carbonate and the solvent removed to give the crude product. Flash chromatography (flash silica: 10% methanol in ethyl acetate) followed by repeated fractional crystallisation (6 times from ethyl acetate/DIPE) gave the desired regioisomer N-cyclohexyl-N-methyl 4-(1 H-imidazo[4,5-c]pyridylmethyl)benzamide (0.39 g, 5%) as an off white crystalline solid.

m.p. 121°-123° C.

Analysis Calculated for $C_{21}H_{24}N_4O_0.6H_2O$
Requires C 70.21 H 7.07 N 15.60.
Found C 70.08 H 6.91 N 15.37.
i.r. (KBr) 3080, 2930, 1615 cm$^{-1}$.
delta$_H$ 9.17 (1 H, s), 8.42 (1 H, d, J 5.6 Hz), 8.03 (1 H, s), 7 37 (2 H, d, J 7.8 Hz), 7.27–7.19 (3H, m), 5.42 (2H, s), 4.50, 3.37 (1 H, 2br m), 2.96, 2.76 (3H, 2br s), 2.05–1.02 (10H, br m).

PHARMACOLOGY EXAMPLE 1

The inhibition of 3H-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 Mm NaCl, 10 Mm Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a-band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5 mm MgCl$_2$, 2 Mm EDTA, pH 7.0), snap frozen in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step wa,,j repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Tri-buffered solutions of the selected antagonist of predetermined concentrations. Eacti of these solutions contained $^3$H-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10 mM Tris, 5mM MgCl$_2$, pH 7.0, 0.25% BSA) to make the final volume 1 ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

$$\%\text{Inhibition} = [(\text{TB-TBA})/\text{SB}] \times 100$$

where the specific binding SB = TB−NSB

Table 1 lists results from this assay for inhibition of $^3$H-PAF receptor binding for illustrative examples of the compounds of this invention. Also presented in Table 1 is the result for a comparative example (N-cyclohexyl-N-methyl 4-(1 H-imidazo[4,5-c]pyridylmethyl) benzamide. This compound (a PAF antagonist described in EP-A-0260613) is not within the scope of the invention.

TABLE 1

Results for inhibition of $^3$H-PAF receptor binding

| Example | Inhibition of $^3$H-PAF binding IC$_{50}$ nM |
|---|---|
| 1 | 300 |
| 6 | 50 |
| 8 | 40 |
| 17(B) | 8 |
| 19(B) | 0.065 |
| 20(B) | 0.015 |
| 35(B) | 0.06 |
| 46(B) | 1 |
| Comparative Example | 10,000 |

PHARMACOLOGY EXAMPLE 2

The activity of the compounds of general formula I is also demonstrated in vivo by their ability to reverse the hypotension caused by an infusion of PAF in rats. Male Sprague-Dawley rats (300–350 g) were anaesthetised with a mixture of sodium pentobarbitone, 22.5 mg/kg and thiopental 62.5 mg/kg. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

PAF, 100 ng/kg/min was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response (ED$_{50}$) calculated by straight line interpolation and the results are presented in Table 2. Also presented in Table 2 is the result for a comparative example (N-cyclohexyl-N-methyl 4-(1 H-imidazo[4,5-c]pyridylmethyl)benzamide. This compound (a PAF antagonist described in EP-A-0260613) is not within the scope of the invention.

TABLE 2

Results for inhibition of PAF-induced hypotension in the rat

| Example | ED$_{50}$ (μg/kg i.v.) |
| --- | --- |
| 17(B) | 3.1 |
| 18(B) | 0.7 |
| 20(B) | 0.7 |
| 50 | 0.8 |
| Comparative Example | 150 |

PHARMACOLOGY EXAMPLE 3

The inhibition of PAF induced bronchoconstriction was measured in anaesthetised artificially ventilated guinea-pigs (450–500 g) using a modified version of the Konzett-Rössler technique (Konzett M and Rössler R, *Naunym-Schmiedeb. Arch. Exp. Pathol. Pharmakol.*, 1940, 197, 71). Male Dunkin-Hartley guinea-pigs were anaesthetised with urethane, 1.6 g/kg. Through a midline neck incision, the trachea was cannulated and the animal ventilated with a constant tidal volume set between 5 and 15 ml, to give a tracheallinflation pressure of 15 mmhg at a rate of 40 per minute. A carotid artery was cannulated for the measurement of blood pressure and heart rate and both jugular veins were cannulated, one for the infusion of PAF and the other for the administration of test compounds. PAF, 40 ng/kg/min in saline with 0.25% bovine serum albumin, was infused i.v. to produce a 100% increase in tracheal inflation pressure, and bronchoconstrictor effects were determined. Test compounds were administered p.o. (10, mg/kg) 1, hour before the infusion of PAF was started whilst the animals were conscious. The percentage inhibition of PAF-induced bronchoconstriction (ED$_{50}$) was determined and the results are presented in Table 3.

TABLE 3

Results for inhibition of PAF-induced Bronchocontriction in the guinea pig

| Example | % Inhibition (10 mg/kg p.o.) |
| --- | --- |
| 20(B) | 94 |
| 35(B) | 60 |
| 37(B) | 90 |
| 40(B) | 61 |

We claim:

1. A process for preparing a compound of general formula I

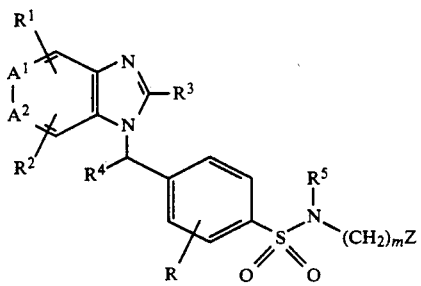

I wherein:

A$^1$ is =N—, =CH— or =CR$^1$—;
A$^2$ is =N—, =CH— or =CR$^2$—;
provided that one of A$^1$ and A$^2$ is a nitrogen atom and the other of A$^1$ and A$^2$ is other than a nitrogen atom;

R represents hydrogen, —C$_1$—C$_6$ alkyl, —C$_2$—C$_6$ alkenyl, —C$_2$—C$_6$ alkynyl, halogen or OC$_1$—C$_6$ alkyl;

R$^1$ and R$^2$ each independently represents hydrogen, —C$_1$—C$_6$ alkyl, —C$_2$—C$_6$ alkenyl, —C$_2$—C$_6$ alkynyl, halogen, —CN, —CO$_2$H, —CO$_2$C$_1$—C$_6$ alkyl, —COHN$_2$, —CHO, —CH$_2$OH, —CF$_3$, —OC$_1$—C$_6$ alkyl, —SC$_1$—C$_6$ alkyl, —SOC$_1$—C$_6$ alkyl, —SO$_2$C$_1$—C$_6$ alkyl, —NH$_2$, —NHCOMe or —NO$_2$, or R$^1$R$^2$ together with the carbon atoms to which they are attached form a fused phenyl ring;

R$^3$ represents hydrogen, —C$_1$—C$_6$ alkyl, —C$_2$—C$_6$ alkenyl, —C$_2$—C$_6$ alkynyl, —OC$_1$—C$_6$ alkyl, —SC$_1$—C$_6$ alkyl, —(C$_1$—C$_6$ alkyl)OC$_1$—C$_6$ alkyl, —(C$_1$—C$_6$ alkyl)SC$_1$—C$_6$ alkyl, —CF$_3$, —(C$_1$—C$_6$ alkyl)phenyl, —C$_3$—C$_8$ cycloalkyl, —C$_4$—C$_8$ cycloalkenyl, —(C$_1$—C$_6$ alkyl)C$_3$—C$_8$ cycloalkyl, —(C$_1$—C$_6$alkyl)C$_4$—C$_8$ cycloalkenyl or thiophenyl;

R$^4$ represents hydrogen, —C$_1$—C$_6$ alkyl, —C$_2$—C$_6$ alkenyl, —C$_2$—C$_6$ alkynyl, —CO$_2$C$_1$—C$_6$ alkyl, —SC$_1$—C$_6$ alkyl, —(C$_1$—C$_6$ alkyl)SC$_1$C$_6$ alkyl, —(C$_1$—C$_6$ alkyl)OC$_1$—C$_6$ alkyl, —(C$_1$—C$_6$ alkyl)phenyl or thiophenyl;

R$^5$ represents hydrogen, —C$_1$—C$_6$ alkyl, —C$_2$—C$_6$ alkenyl, —C$_2$—C$_6$ alkynyl, —COC$_1$—C$_6$ alkyl, —CO$_2$C$_1$—C$_6$ alkyl, —(CO$_2$C$_1$—C$_6$ alkyl)phenyl, —(C$_1$—C$_6$ alkyl)CO$_2$C$_1$—C$_6$ alkyl, —(C$_1$—C$_6$ alkyl)phenyl, —C$_3$—C$_8$ cycloalkyl, C$_4$—C$_8$ cycloalkenyl or phenyl optionally substituted by one or more substituents selected from —C$_1$—C$_6$ alkyl, —OC$_1$—C$_6$ alkyl, halogen, —CF$_3$, —CN;

m is an integer from 0 to 3;

z is either a —CR$^6$R$^7$R$^8$ or —CR$^6$=CR$^7$R$^8$ group;

wherein each of R$^6$, R$^7$, and R$^8$ independently represents hydrogen, halogen, —C$_1$—C$_{18}$ alkyl optionally substituted by one or more halogen atoms, —C$_2$—C$_{18}$ alkenyl, —C$_2$—C$_{18}$ alkynyl, —(C$_1$—C$_6$ alkyl)OC$_1$—C$_{18}$ alkyl, —(C$_1$—C$_6$ alkyl)SC$_1$—C$_{18}$ alkyl, —(C$_1$—C$_6$ alkyl)O(C$_1$—C$_6$ alkyl)OC$_1$—C$_6$ alkyl, —(C$_1$—C$_6$ alkyl)S(C$_1$—C$_6$ alkyl)OC$_1$—C$_6$ alkyl, —(C$_1$—C$_6$ alkyl)O(C$_1$—C$_6$ alkyl)SC$_1$—C$_6$ alkyl, —(C$_1$—C$_6$ alkyl)S(C$_1$—C$_6$ alkyl)SC$_1$—C$_6$ alkyl), —C$_1$—C$_6$ alkyl)OC$_2$—C$_6$ alkenyl, —C$_3$—C$_8$ cycloalkyl, —C$_4$—C$_8$ cycloalkenyl, —(C$_1$—C$_6$ alkyl)C$_3$—C$_8$ cycloalkyl, —(C$_1$—C$_6$ alkyl)-C$_4$—C$_8$ cycloalkenyl, —(C$_1$—C$_6$ alkyl)OC$_3$—C$_8$ cycloalkyl, —(C$_1$—C$_6$ alkyl)OC$_4$—C$_8$ cycloalkenyl, —(C$_1$—C$_6$ alkyl)SC$_3$—C$_8$ cycloalkyl, —(C$_1$—C$_6$ alkyl)SC$_4$—C$_8$ cycloalkenyl, —(C$_1$—C$_6$ alkyl)N(C$_1$—C$_6$ alkyl)$_2$, —(C$_1$—C$_6$ alkyl)morpholino, —(C$_1$—C$_6$ alkyl)OCH$_2$Ph, —CH$_2$OSi(C$_1$—C$_6$ alkyl)$_3$, —CH$_2$OSiPh$_2$C$_1$—C$_6$ alkyl or a group —D wherein D represents a group;

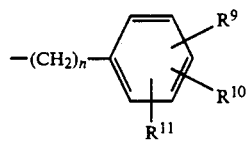

wherein n is an integer from 0 to 3, and each of R$^9$, R$^{10}$ and R$^{11}$ is independently hydrogen, —C$_1$—C$_6$ alkyl, —OC$_1$—C$_6$ alkyl, —SC$_1$—C$_6$ alkyl, —N(C$_1$—C$_6$ alkyl)$_2$, —C$_2$—C$_6$ alkenyl, —C$_2$—C$_6$ alkynyl, —OCH$_2$Ph, halogen, —CN, —CF$_3$, —CO$_2$H, —CO$_2$ C$_1$—C$_6$ alkyl, —CONH$_2$, —CONHC$_1$—C$_6$ alkyl, —CONH($C_1$—$C_6$ alkyl)$_2$, —CHO, —CH$_2$OH, —NH$_2$, —NHCO$C_1$—$C_6$ alkyl, —SO$C_1$—$C_6$ alkyl, or —SO$_2C_1$—$C_6$ alkyl;

or a pharmaceutically or veterinarily acceptable acid addition salt or hydrate thereof;

the process comprising:

treating a substituted diamino compound of general formula IV

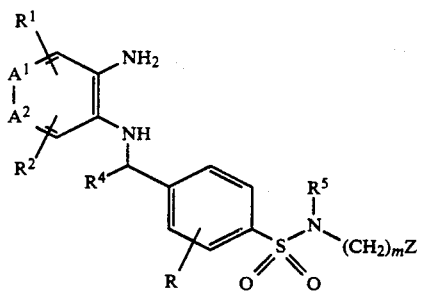

wherein $A^1$, $A^2$, R, $R^1$, $R^2$, $R^4$, $R^5$, m and z are as defined in general formula I, with a carboxylic acid of general formula V $R^3CO_2H$  V wherein $R^3$ is as defined in general formula I.

* * * * *